(12) United States Patent
Reddy et al.

(10) Patent No.: US 11,534,602 B2
(45) Date of Patent: Dec. 27, 2022

(54) IMPLANTATION OF AN ACTIVE MEDICAL DEVICE USING THE INTERNAL THORACIC VASCULATURE

(71) Applicant: CARDIAC PACEMAKERS, INC., St. Paul, MN (US)

(72) Inventors: G. Shantanu Reddy, Minneapolis, MN (US); James O. Gilkerson, Stillwater, MN (US); Andrew L. De Kock, Ham Lake, MN (US); James K. Cawthra, Jr., Ramsey, MN (US); Eric Hammill, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 183 days.

(21) Appl. No.: 16/776,207

(22) Filed: Jan. 29, 2020

(65) Prior Publication Data

US 2020/0246610 A1    Aug. 6, 2020

Related U.S. Application Data

(63) Continuation of application No. 15/667,167, filed on Aug. 2, 2017, now Pat. No. 10,576,267.

(Continued)

(51) Int. Cl.
*A61N 1/05* (2006.01)
*A61N 1/39* (2006.01)
(Continued)

(52) U.S. Cl.
CPC .............. *A61N 1/05* (2013.01); *A61B 5/686* (2013.01); *A61N 1/056* (2013.01); *A61N 1/362* (2013.01); *A61N 1/365* (2013.01); *A61N 1/3621* (2013.01); *A61N 1/36521* (2013.01); *A61N 1/3702* (2013.01); *A61N 1/3956* (2013.01);
(Continued)

(58) Field of Classification Search
None
See application file for complete search history.

(56) References Cited

U.S. PATENT DOCUMENTS 5,331,966 A   7/1994  Bennett et al.
6,219,582 B1  4/2001  Hofstad et al.
(Continued)

FOREIGN PATENT DOCUMENTS

WO   2016148928 A1   9/2016
WO   2016149262 A1   9/2016

OTHER PUBLICATIONS

International Search Report and Written Opinion dated Sep. 29, 2017 for International Application No. PCT/US2017/045109.
(Continued)

*Primary Examiner* — Erica S Lee
(74) *Attorney, Agent, or Firm* — Seager, Tufte & Wickhem LLP

(57) ABSTRACT

Implantable devices and systems include one or more leads adapted to be emplaced in the internal thoracic vein (ITV) of a patient. The lead may include features to adapt the lead for such placement. An associated device for use with the lead may include operational circuitry adapted for use with a lead having an electrode for sensing and/or therapy purposes coupled thereto. Methods for implantation and use of such devices and systems are disclosed as well.

12 Claims, 33 Drawing Sheets

Related U.S. Application Data

(60) Provisional application No. 62/437,693, filed on Dec. 22, 2016, provisional application No. 62/401,338, filed on Sep. 29, 2016, provisional application No. 62/371,343, filed on Aug. 5, 2016.

(51) Int. Cl.
| | | |
|---|---|---|
| *A61N 1/365* | (2006.01) | |
| *A61B 5/00* | (2006.01) | |
| *A61N 1/362* | (2006.01) | |
| *A61N 1/37* | (2006.01) | |
| *A61B 5/363* | (2021.01) | |
| *A61N 1/375* | (2006.01) | |
| *A61N 1/372* | (2006.01) | |

(52) U.S. Cl.
CPC ....... *A61N 1/3962* (2013.01); *A61N 1/39622* (2017.08); *A61B 5/363* (2021.01); *A61N 1/0563* (2013.01); *A61N 1/3756* (2013.01); *A61N 1/37288* (2013.01); *A61N 1/37512* (2017.08)

(56) References Cited

U.S. PATENT DOCUMENTS

| | | | |
|---|---|---|---|
| 6,647,292 | B1 | 11/2003 | Bardy et al. |
| 6,721,597 | B1 | 4/2004 | Bardy et al. |
| 7,149,575 | B2 | 12/2006 | Ostroff et al. |
| 7,655,014 | B2 | 2/2010 | Ko et al. |
| 7,783,340 | B2 | 8/2010 | Sanghera et al. |
| 7,818,068 | B2 | 10/2010 | Meadows et al. |
| 7,962,222 | B2 | 6/2011 | He et al. |
| 8,005,543 | B2 | 8/2011 | Libbus et al. |
| 8,157,813 | B2 | 4/2012 | Ko et al. |
| 8,386,048 | B2 | 2/2013 | McClure et al. |
| 8,483,843 | B2 | 7/2013 | Sanghera et al. |
| 8,543,216 | B2 | 9/2013 | Carbunaru et al. |
| 2005/0043765 | A1* | 2/2005 | Williams .............. A61N 1/057 607/9 |
| 2007/0213813 | A1 | 9/2007 | Von Segesser et al. |
| 2008/0071339 | A1 | 3/2008 | Stalker et al. |
| 2010/0114195 | A1 | 5/2010 | Burnes et al. |
| 2010/0191043 | A1 | 7/2010 | Chin |
| 2012/0029335 | A1 | 2/2012 | Sudam et al. |
| 2014/0100637 | A1* | 4/2014 | Zhang ................. A61N 1/3718 607/62 |
| 2014/0107719 | A1 | 4/2014 | Bornzin et al. |
| 2014/0114371 | A1 | 4/2014 | Westlund et al. |
| 2014/0330326 | A1 | 11/2014 | Thompson-Nauman et al. |
| 2015/0025612 | A1 | 1/2015 | Haasl et al. |
| 2015/0051610 | A1 | 2/2015 | Schmidt et al. |
| 2015/0196756 | A1 | 7/2015 | Stahmann et al. |
| 2015/0196757 | A1 | 7/2015 | Stahmann et al. |
| 2015/0196758 | A1 | 7/2015 | Stahmann et al. |
| 2015/0196769 | A1 | 7/2015 | Stahmann et al. |
| 2015/0224320 | A1 | 8/2015 | Stahmann |
| 2015/0290467 | A1* | 10/2015 | Ludwig ................ A61N 1/3931 607/4 |
| 2015/0297902 | A1 | 10/2015 | Stahmann et al. |
| 2015/0352358 | A1 | 12/2015 | Atwater |
| 2015/0360036 | A1 | 12/2015 | Kane et al. |
| 2016/0038742 | A1 | 2/2016 | Stahmann et al. |
| 2016/0059007 | A1 | 3/2016 | Koop |
| 2016/0059022 | A1 | 3/2016 | Stahmann et al. |
| 2016/0059024 | A1 | 3/2016 | Stahmann et al. |
| 2016/0059025 | A1 | 3/2016 | Stahmann et al. |
| 2016/0089539 | A1 | 3/2016 | Gilkerson et al. |
| 2016/0228712 | A1 | 8/2016 | Koop |
| 2016/0256692 | A1 | 9/2016 | Baru |
| 2017/0021159 | A1 | 1/2017 | Reddy et al. |
| 2018/0036527 | A1 | 2/2018 | Reddy et al. |
| 2018/0036547 | A1 | 2/2018 | Reddy |
| 2018/0133462 | A1 | 5/2018 | Reddy et al. |
| 2018/0133463 | A1 | 5/2018 | Reddy |
| 2018/0133494 | A1 | 5/2018 | Reddy |
| 2018/0178019 | A1 | 6/2018 | Reddy et al. |
| 2018/0193060 | A1 | 7/2018 | Reddy et al. |

OTHER PUBLICATIONS

Moeinipour et al., "A Rare Central Venous Catheter Malposition: A Case Report," Anesth Pain Med., 4(1): 1-3, Feb. 5, 2014.

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

* cited by examiner

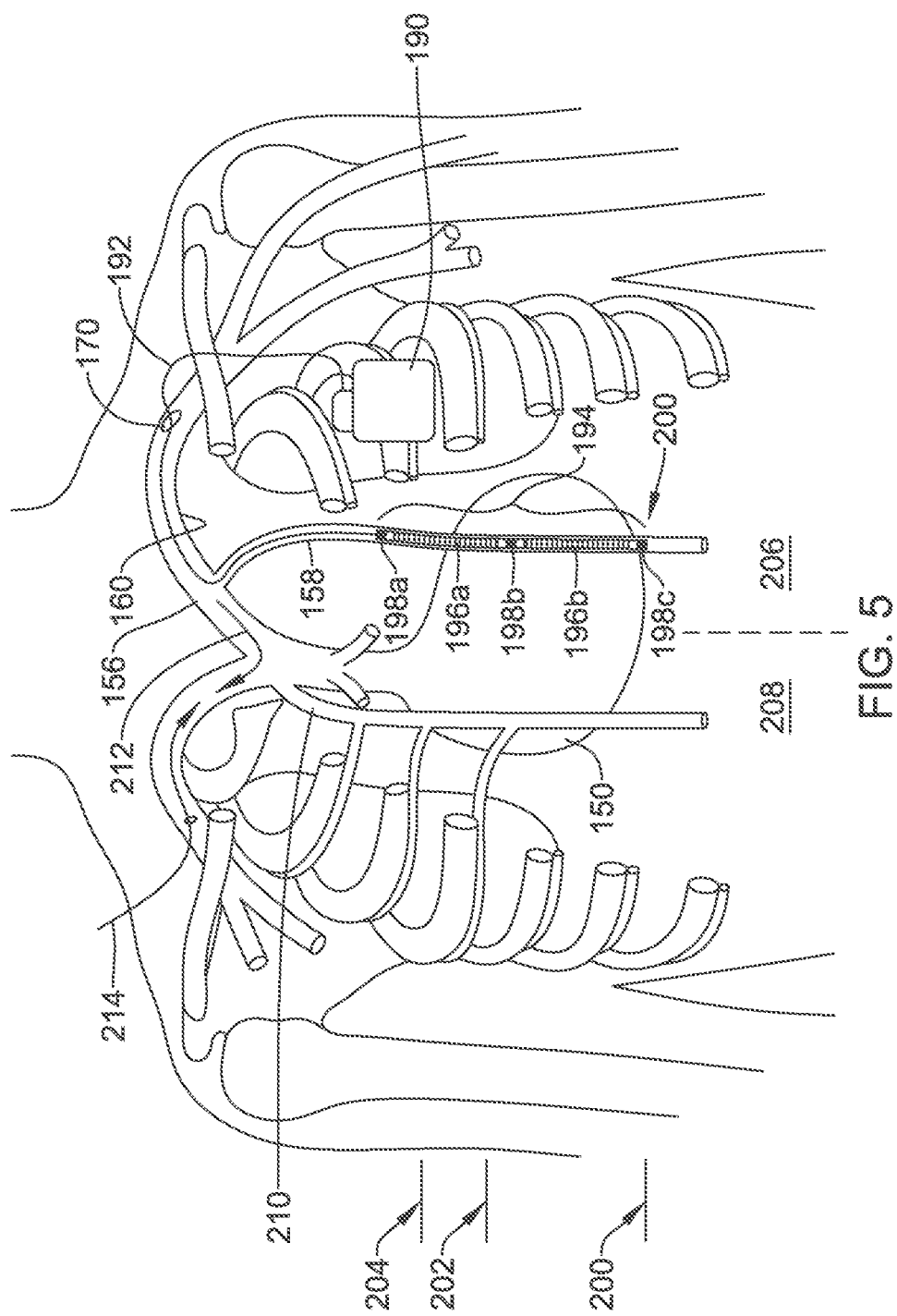

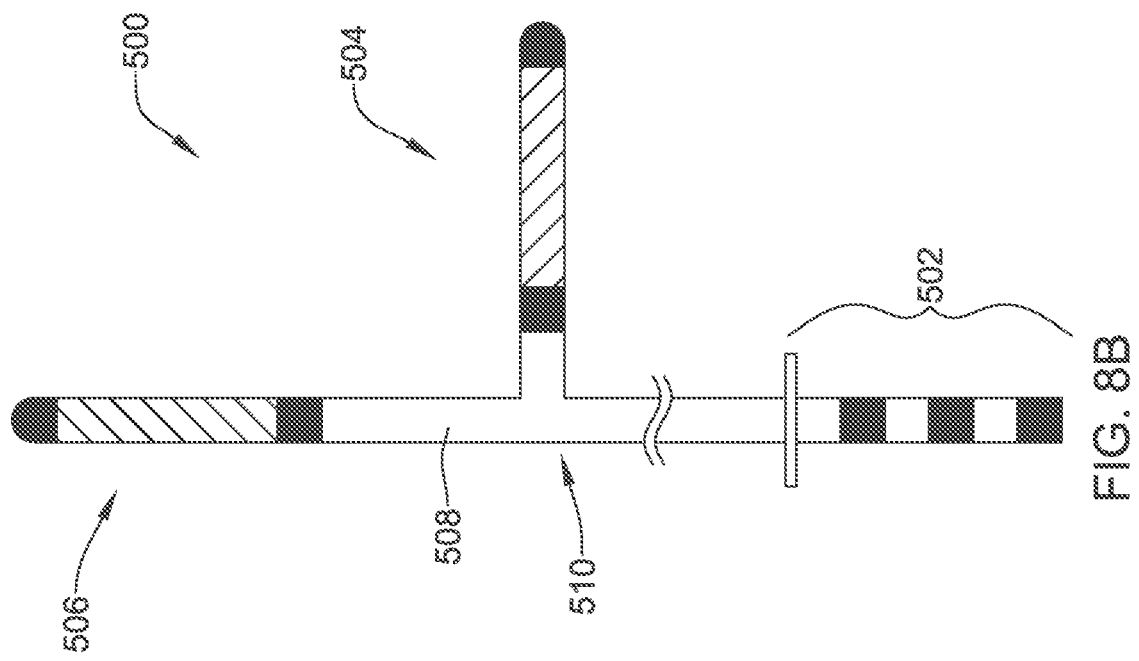

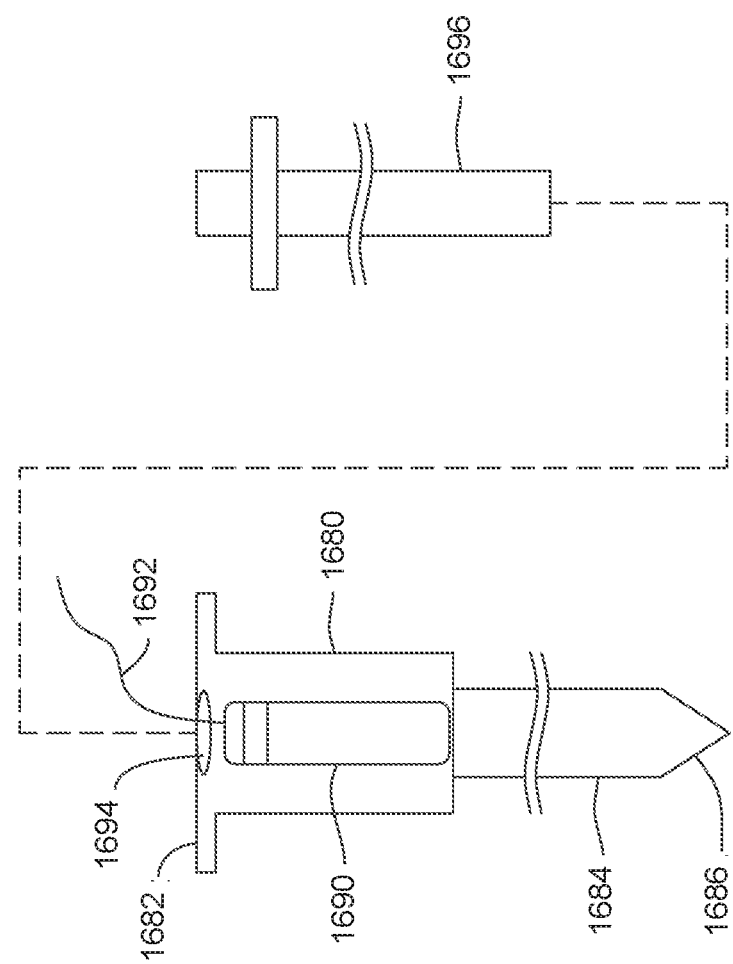

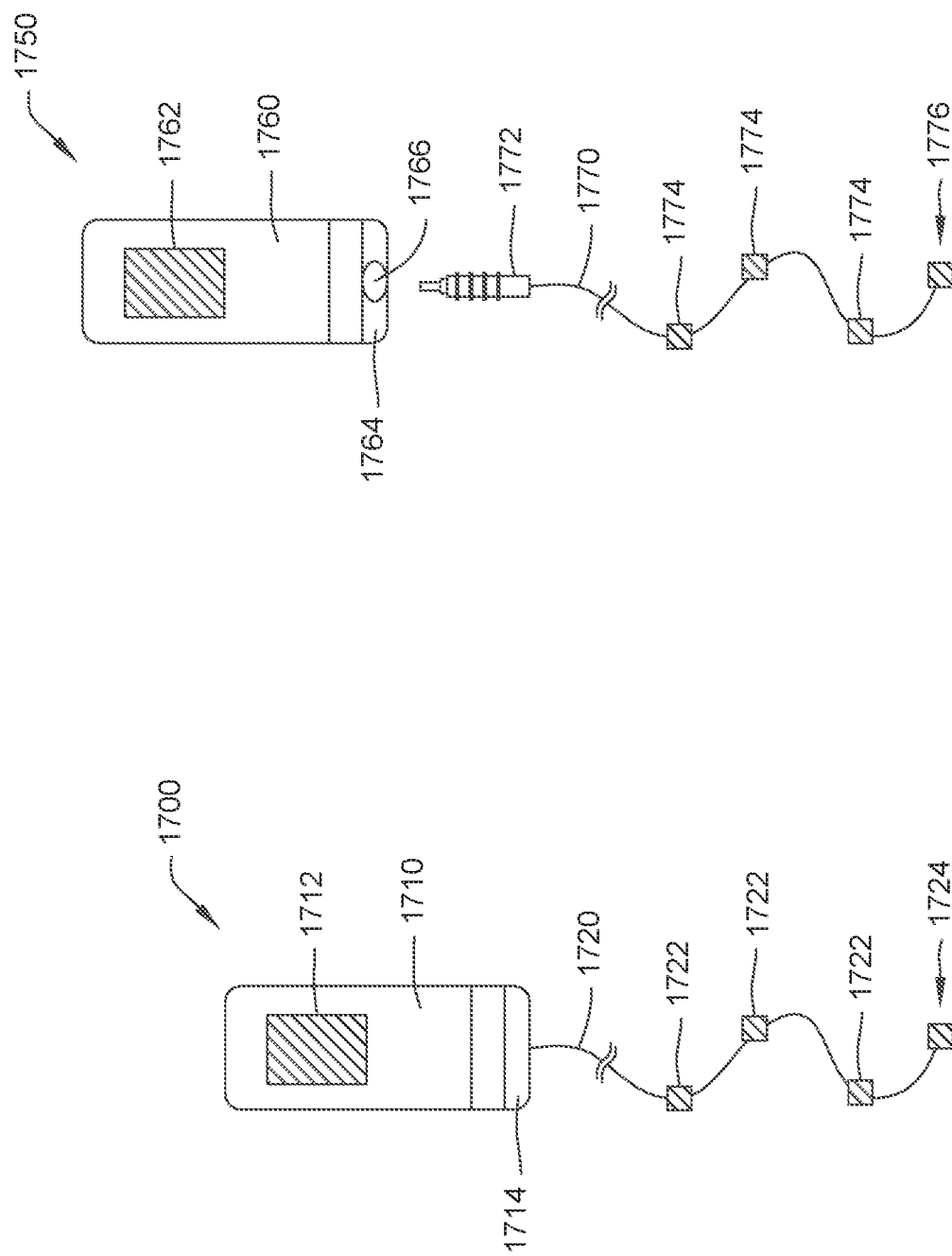

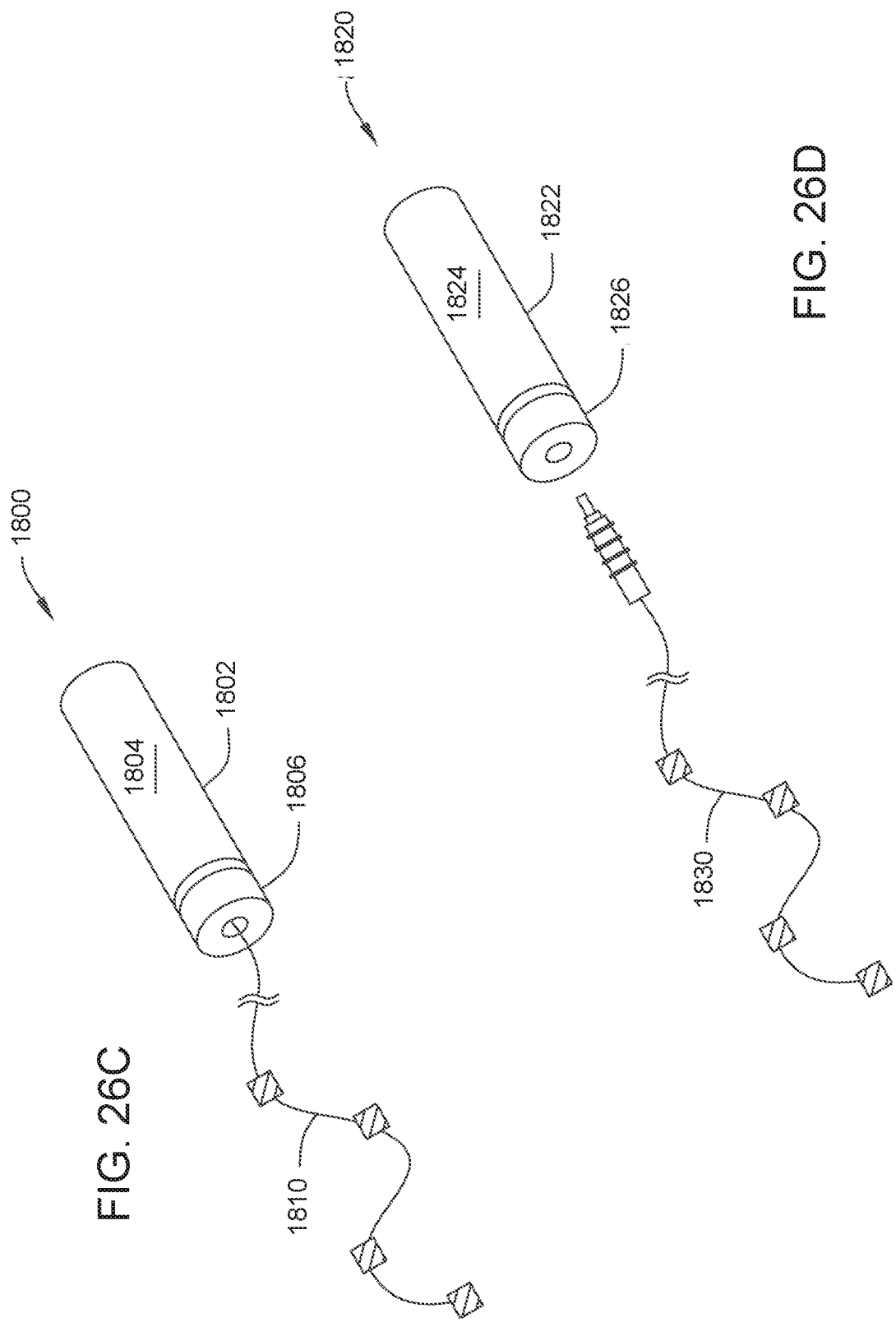

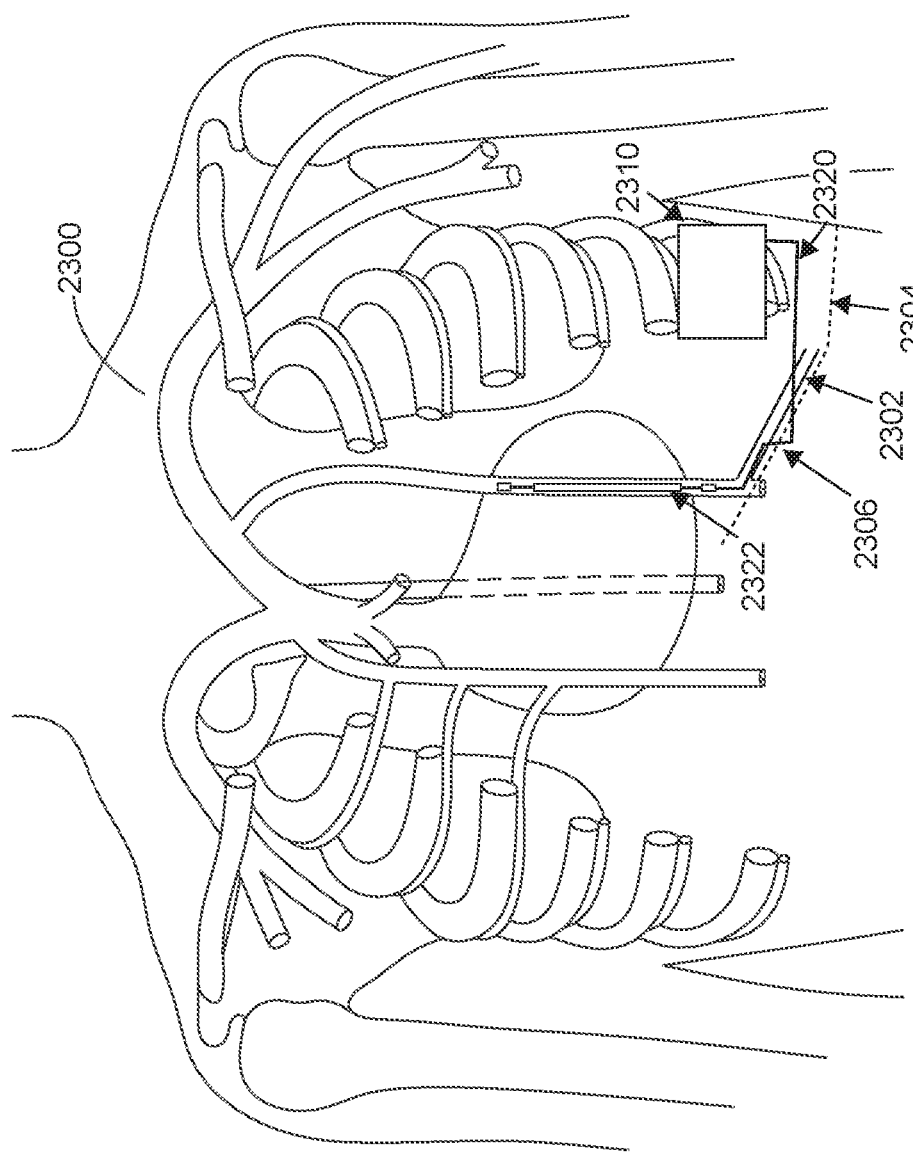

IMPLANTATION OF AN ACTIVE MEDICAL DEVICE USING THE INTERNAL THORACIC VASCULATURE

CROSS REFERENCE TO RELATED APPLICATIONS

The present application is a continuation of U.S. patent application Ser. No. 15/667,167, filed Aug. 2, 2017 and titled IMPLANTATION OF AN ACTIVE MEDICAL DEVICE USING THE INTERNAL THORACIC VASCULATURE, now U.S. Pat. No. 10,576,267, which claims the benefit of and priority to U.S. Provisional Patent App. Ser. No. 62/371,343, filed Aug. 5, 2016 and titled IMPLANTATION OF AN ACTIVE MEDICAL DEVICE USING THE INTERNAL THORACIC VASCULATURE; U.S. Provisional Patent App. Ser. No. 62/401,338, filed Sep. 29, 2016 and titled PACEMAKERS FOR IMPLANT IN THE INTERNAL THORACIC VASCULATURE WITH COMMUNICATION TO OTHER IMPLANTABLE DEVICES; and U.S. Provisional Patent App. Ser. No. 62/437,693, filed Dec. 22, 2016 and titled AZYGOS, INTERNAL THORACIC, AND/OR INTERCOSTAL VEIN IMPLANTATION AND USE OF MEDICAL DEVICES, the disclosures of which are incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart cause the lead to flex with each heartbeat. The advent of subcutaneous defibrillators allows avoidance of these lead failure issues, with leads implanted beneath the skin and over the ribcage of the patient and not subjected to the repeated flexing.

However, subcutaneous defibrillators require higher energy for defibrillation, causing the pulse generators for such systems to be larger than their transvenous predecessors, and both bradycardia pacing and anti-tachycardia pacing to avoid high voltage shock for certain conditions, is of limited utility as such pacing subcutaneously can be very uncomfortable for the patient. This has led to interest in further alternative locations for implantable defibrillators, and other medical devices such as the implantable pacemaker.

OVERVIEW

The present inventors have recognized, among other things, that a problem to be solved is the need for additional alternatives to existing implant techniques and locations for therapy and sensing apparatuses in the thorax of a patient. The internal thoracic vein (ITV), as well as the intercostal veins, the superior epigastric vein, and the azygos, hemiazygos, and accessory hemiazygos veins may each offer new and useful alternative locations as described further below. The ITV may be accessed by several avenues explained and discussed below. Electrodes and/or leads in the ITV may be used for various purposes including, for example, to deliver therapy such as pacing (such as bradycardia pacing or anti-tachyarrhythmia pacing) or defibrillation, or to sense cardiac activity from in the ITV in order to assist with rhythm analysis by a second device and/or to confirm or optimize operation of a second or more implantable device(s).

A first non-limiting example takes the form of a method of implanting a lead for use in a cardiac stimulus system in a patient, the lead having at least one electrode thereon; the method comprising inserting the lead into the internal thoracic vein (ITV) to a desired location relative to the heart of a patient.

Additionally or alternatively a second non-limiting example takes the form of a method as in the first non-limiting example further comprising establishing access to a brachiocephalic vein of the patient and advancing a distal portion of the lead through the ostium of the ITV from the brachiocephalic vein.

Additionally or alternatively a third non-limiting example takes the form of a method as in the second non-limiting example wherein the step of establishing access to the brachiocephalic vein comprises inserting an introducer sheath into one of the axillary, jugular, cephalic or subclavian veins of the patient and advancing at least the lead through the introducer sheath, into the brachiocephalic vein, and then through the ostium of the ITV.

Additionally or alternatively a fourth non-limiting example takes the form of a method as in either of the second or third non-limiting examples, further comprising advancing a guidewire to and into the ostium of the ITV.

Additionally or alternatively a fifth non-limiting example takes the form of a method as in any of the second to fourth non-limiting examples, further comprising advancing a guide catheter to and into the ostium of the ITV.

Additionally or alternatively a sixth non-limiting example takes the form of a method as in the first non-limiting example further comprising establishing access to the ITV through an intercostal space between two ribs including: inserting a needle into one of the ITV through the intercostal space; and advancing a sheath into the intercostal space and into the ITV; and wherein the step of inserting the lead comprises advancing the distal end of the lead through the sheath and intro the ITV.

Additionally or alternatively a seventh non-limiting example takes the form of a method as in the sixth non-limiting example, wherein the step of advancing the distal end of the lead through the sheath and into the ITV comprises advancing the distal end of the lead in an inferior direction into the ITV.

Additionally or alternatively an eighth non-limiting example takes the form of a method as in the sixth non-limiting example, wherein the step of advancing the distal end of the lead through the sheath and into the ITV comprises advancing the distal end of the lead in a superior direction.

Additionally or alternatively a ninth non-limiting example takes the form of a method as in the eighth non-limiting example, further comprising tunneling from the left axilla to the intercostal space, attaching an implantable pulse generator to the lead and implanting the pulse generator at the left axilla.

Additionally or alternatively a tenth non-limiting example takes the form of a method as in the first non-limiting example, further comprising establishing access to the superior epigastric vein at a location inferior to the lower rib margin and introducing the lead through the epigastric vein and superiorly into the ITV.

Additionally or alternatively an eleventh non-limiting example takes the form of a method as in the tenth non-limiting example, wherein the step of establishing access to the superior epigastric vein comprises: inserting a needle into the superior epigastric vein; and advancing a sheath into the superior epigastric vein; and the step of introducing the lead through the superior epigastric vein comprises advancing the distal end of the lead through the sheath and into the ITV.

Additionally or alternatively a twelfth non-limiting example takes the form of a method as in either the tenth or eleventh non-limiting examples, further comprising tunneling from the left axilla to the location where the ITV is accessed and a proximal portion of the lead in the tunnel, wherein the method further comprises attaching an implantable pulse generator to the lead and implanting the pulse generator at the left axilla.

Additionally or alternatively a thirteenth non-limiting example takes the form of a method as in any of the first to twelfth non-limiting examples, further comprising anchoring the lead in the ITV using an inflatable balloon.

Additionally or alternatively a fourteenth non-limiting example takes the form of a method as in any of the first to twelfth non-limiting examples, further comprising anchoring the lead in the ITV using an expandable member, the expandable member selected from the group consisting of a lobe, a tine, a hook, or a stent.

Additionally or alternatively a fifteenth non-limiting example takes the form of a method as in any of the first to twelfth non-limiting examples, wherein the lead is configured to have a curvature and the method further comprises anchoring the lead by allowing it to assume the curvature once inserted into the ITV.

Additionally or alternatively a sixteenth non-limiting example takes the form of a method as in any of the first to fifteenth non-limiting examples, further comprising attaching a suture sleeve and suturing the suture sleeve to subcutaneous tissue to the lead to hold the lead in position.

Additionally or alternatively a seventeenth non-limiting example takes the form of a method as in any of the first to sixteenth non-limiting examples, wherein the ITV is the right ITV.

Additionally or alternatively an eighteenth non-limiting example takes the form of a method as in any of the first to sixteenth non-limiting examples, wherein the ITV is the left ITV.

A nineteenth non-limiting example takes the form of a method of implanting a cardiac stimulus system comprising: performing the method of the first non-limiting example to implant a first lead in the right ITV; performing the method of the first non-limiting example to implant a second lead in the left ITV; and coupling the first and second leads to a pulse generator for the cardiac stimulus system.

Additionally or alternatively, a non-limiting example may take the form of an implantation tool set configured for use in a method as in any of the first to nineteenth non-limiting examples.

A twentieth non-limiting example takes the form of a method of treating a patient comprising delivering therapy between a first electrode disposed on a lead which is placed in an ITV and at least a second electrode.

Additionally or alternatively a twenty-first non-limiting example takes the form of a method as in the twentieth non-limiting example wherein the therapy is a defibrillation therapy, and the second electrode is disposed on an implantable pulse generator also placed in the patient.

Additionally or alternatively a twenty-second non-limiting example takes the form of a method as in the twenty-first non-limiting example, wherein the implantable pulse generator is in the left axilla, and the lead and electrode are in the right ITV.

Additionally or alternatively a twenty-third non-limiting example takes the form of a method as in the twenty-first non-limiting example, wherein the implantable pulse generator is in the left axilla, and the lead and electrode are in the left ITV.

Additionally or alternatively a twenty-fourth non-limiting example takes the form of a method as in the twenty-first non-limiting example, wherein the implantable pulse generator is placed in a subclavicular pectoral position on the patient's chest.

Additionally or alternatively a twenty-fifth non-limiting example takes the form of a method as in the twentieth non-limiting example, wherein the therapy is a bradycardia pacing therapy.

Additionally or alternatively a twenty-sixth non-limiting example takes the form of a method as in the twentieth non-limiting example, wherein the therapy is an anti-tachycardia pacing therapy.

Additionally or alternatively a twenty-seventh non-limiting example takes the form of a method as in the twentieth non-limiting example, wherein the therapy is a cardiac resynchronization therapy.

Additionally or alternatively a twenty-eighth non-limiting example takes the form of a method as in any of the twenty-fifth to twenty-seventh non-limiting examples, wherein the second electrode is also disposed in an ITV.

Additionally or alternatively a twenty-ninth non-limiting example takes the form of a method as in the twenty-eighth non-limiting example, wherein both the first and second electrodes are disposed on a single lead in the right ITV.

Additionally or alternatively a thirtieth non-limiting example takes the form of a method as in the twenty-eighth non-limiting example, wherein both the first and second electrodes are disposed on a single lead in the left ITV.

Additionally or alternatively a thirty-first non-limiting example takes the form of a method as in the twenty-eighth non-limiting example, wherein the first electrode is in the right ITV, and the second electrode is in the left ITV.

Additionally or alternatively a thirty-second non-limiting example takes the form of a method as in any of the twenty-fifth to twenty-seventh non-limiting examples, wherein the second electrode is disposed on an internal pulse generator also implanted in the patient.

Additionally or alternatively a thirty-third non-limiting example takes the form of a method as in the thirty-second non-limiting example, wherein the implantable pulse generator is in the left axilla, and the lead and electrode are in the right ITV.

Additionally or alternatively a thirty-fourth non-limiting example takes the form of a method as in the thirty-second non-limiting example, wherein the implantable pulse generator is in the left axilla, and the lead and electrode are in the left ITV.

Additionally or alternatively a thirty-fifth non-limiting example takes the form of a method as in the thirty-second non-limiting example, wherein the implantable pulse generator is placed in a subclavicular pectoral position on the patient's chest.

Additionally or alternatively a thirty-sixth non-limiting example takes the form of a method as in the twentieth non-limiting example, wherein the therapy is a defibrillation therapy and both the first and second electrodes are disposed on a single lead within the same ITV.

Additionally or alternatively a thirty-seventh non-limiting example takes the form of a method as in the twentieth non-limiting example, wherein the therapy is a defibrillation therapy and the second electrode is disposed subcutaneously on a lead in the patient.

Additionally or alternatively a thirty-eighth non-limiting example takes the form of a method as in the twentieth non-limiting example, wherein the therapy is a defibrillation therapy, wherein the first electrode is electrically in common with a third electrode during the therapy delivery.

Additionally or alternatively a thirty-ninth non-limiting example takes the form of a method as in the thirty-eighth non-limiting example, wherein the third electrode is disposed in the same ITV as the first electrode.

Additionally or alternatively a fortieth non-limiting example takes the form of a method as in the thirty-eighth non-limiting example, wherein the third electrode is disposed in an ITV such that one of the first and third electrodes is in the right ITV, and the other of the first and third electrodes is in the left ITV.

Additionally or alternatively a forty-first non-limiting example takes the form of a method as in any of the twentieth to the fortieth non-limiting examples, wherein the first electrode is a composite electrode including at least a first coil electrode electrically in common with a first ring electrode.

Additionally or alternatively a forty-second non-limiting example takes the form of a method as in any of the twentieth to the fortieth non-limiting examples, wherein the first electrode is a composite electrode including at least first and second coil electrodes electrically in common with one another.

A forty-third non-limiting example takes the form of a method of implanting a lead for use in a cardiac stimulus system in a patient, the lead having at least one electrode thereon; the method comprising inserting a distal end of a lead into the ITV, advancing the lead to a desired location relative to the heart of a patient, and securing the lead in place.

Additionally or alternatively, another non-limiting example may take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, according to a method as in any of the twentieth to forty-third non-limiting examples.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4-5 show superior access to and implantation of a lead in the left ITV;

FIG. 8B shows an illustrative lead that may be used in the implantation configuration of FIG. 8A;

FIG. 25 shows an illustrative insertion tool for a pacemaker in accordance with some examples;

FIGS. 26A-26B show affixed and removable leads with illustrative pacemaker housings;

FIGS. 26C-26D show affixed and removable leads with illustrative pacemaker housings;

FIG. 35 shows an illustrative implanted system.

DETAILED DESCRIPTION

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate fast tachycardia, have created interest in alternative defibrillator and/or pacemaker placement techniques. One proposal has included a substernal placement, with a lead extending beneath the sternum from a position inferior to the lower rib margin, such as in U.S. patent application Ser. No. 15/208,682, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The present inventors have identified still a further alternative. In human anatomy, the internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. The inventors have recognized that the ITV may make a suitable location for placement of a cardiac stimulus lead. While much of the following disclosure focuses on the use of the ITV, many of these concepts could also be applied to the internal thoracic arteries, which may sometimes be referenced as the internal mammary arteries.

Figure 1:
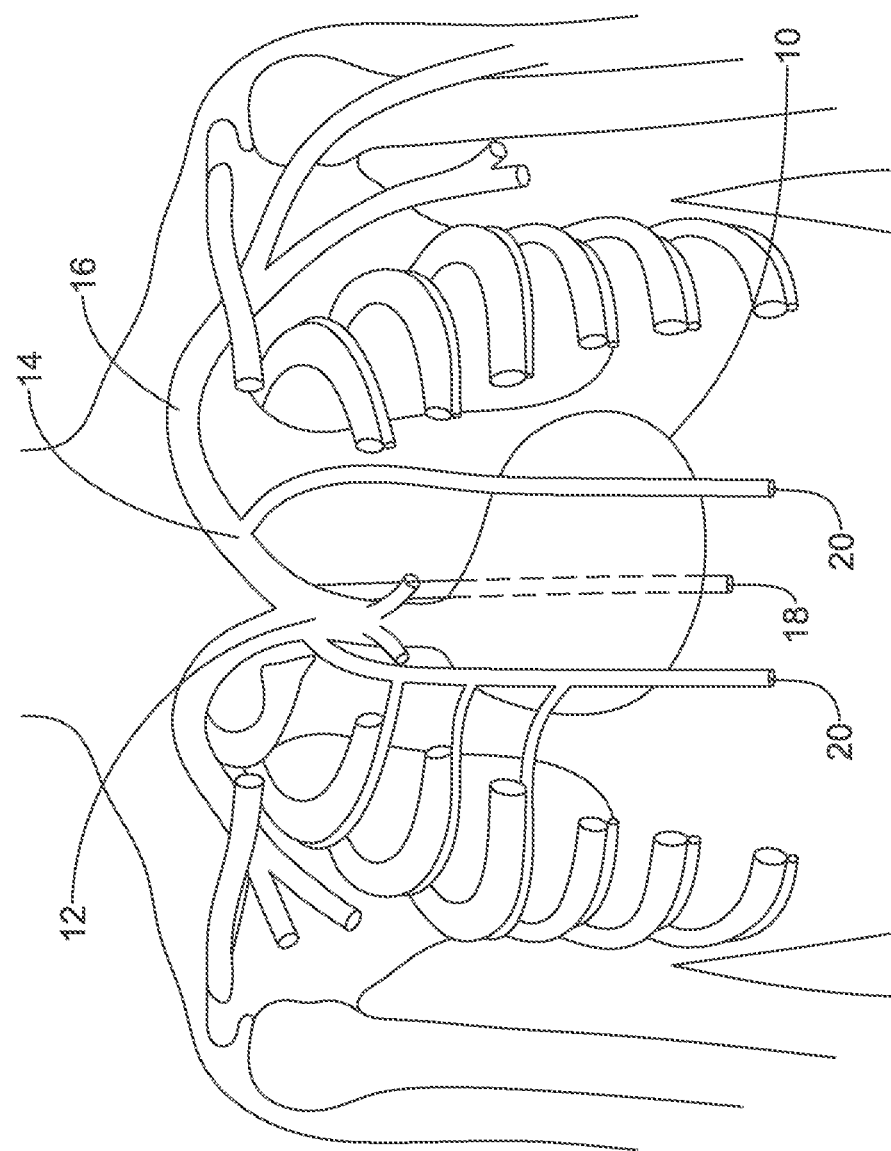
FIG. 1 illustrates the thoracic anatomy including placement of the internal thoracic veins (ITVs)

FIG. 1 illustrates the thoracic anatomy including location of the internal thoracic veins (ITVs). An outline of the heart is shown at 10, with the superior vena cava (SVC) shown at 12. The brachiocephalic veins 14 couple to the SVC and extend past various cephalic branches to the subclavian vein 16. The azygos vein is shown at 18, and the right and left ITV are shown 20.

Certain literature in the field of implantable pacemakers or defibrillators has noted the possibility of the using the azygos vein 18 to implant a lead and electrode to stimulate the vagus nerve (see, for example, U.S. Pat. No. 8,005,543, the disclosure of which is incorporated herein by reference), or as an adjunct to defibrillator function (see Cesario et al., "Azygos vein lead implantation: a novel adjunctive technique for implantable cardioverter defibrillator placement," J. Cardiovasc. Electrophysiol., 2004, 15:780-783). However, such proposals have not found widespread acceptance. However, it does not appear that the ITVs 20 have been proposed.

Figure 2:
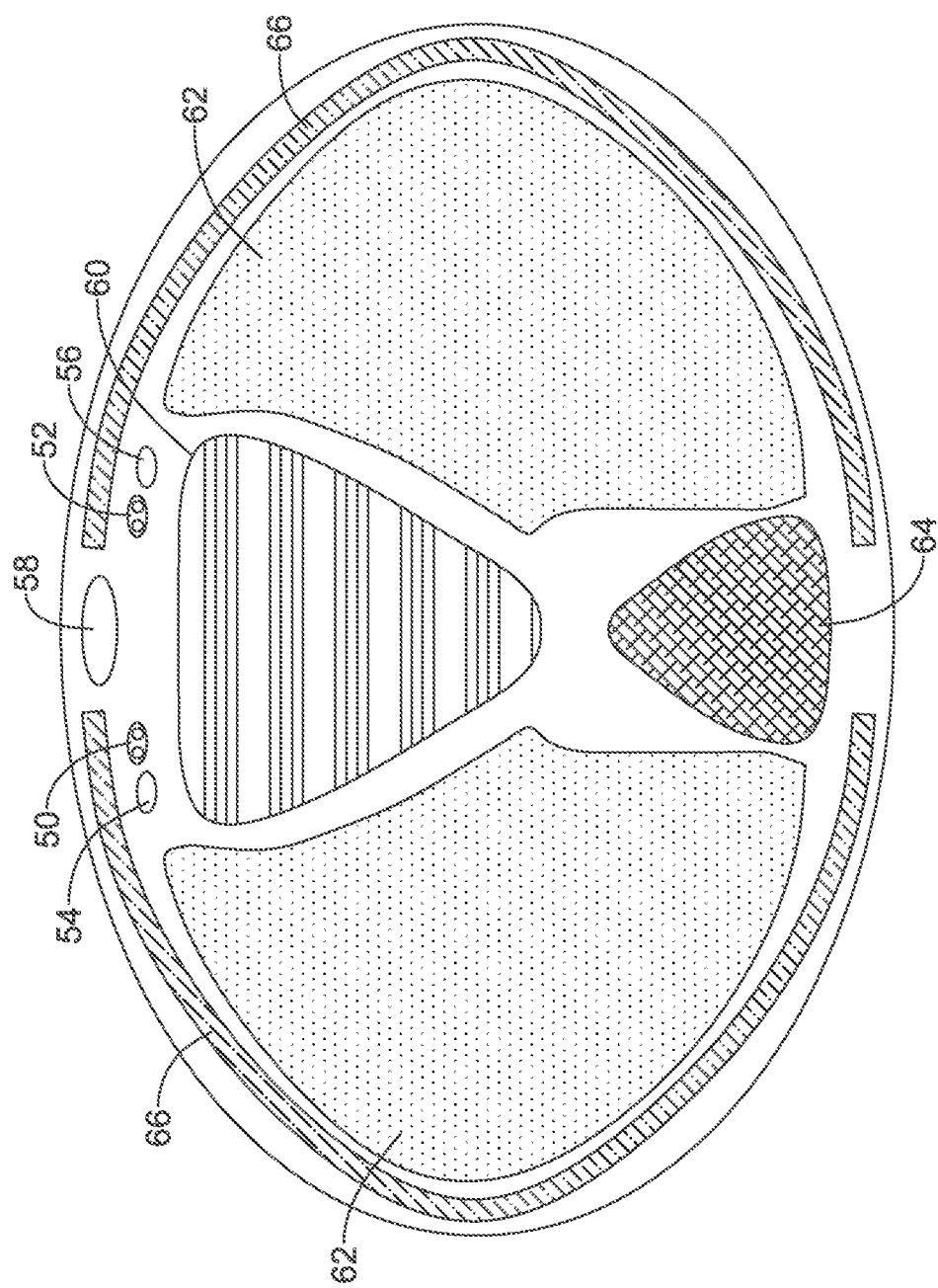
FIG. 2 shows the torso in a section view to highlight the location of the ITVs and arteries.

FIG. 2 shows the torso in a section view to highlight the location of the ITVs and internal thoracic arteries. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs 66 but outside and separate from the pleurae of lungs 62. As used herein, the "ITV" is the name applied for the vein while it runs beneath the chest, that is, superior to the lower margin of the ribs. Inferior to the lower margin of the ribs, the blood vessel continues as the superior epigastric vein.

The relatively superficial position makes the ITV 50, 52 accessible percutaneously inferior to the rib margin at what may be referred to as the paraxiphoid window. Access to the ITV from an access point inferior to the lower rib margin may be described as accessing the ITV via the superior epigastric vein. The ITV 50, 52 may also be accessed in a parasternal position, through intercostal spaces between ribs 66 as further discussed below. Also shown in some examples below are methods to access to the ITV via the superior vasculature, including the brachiocephalic vein.

Figure 3B:
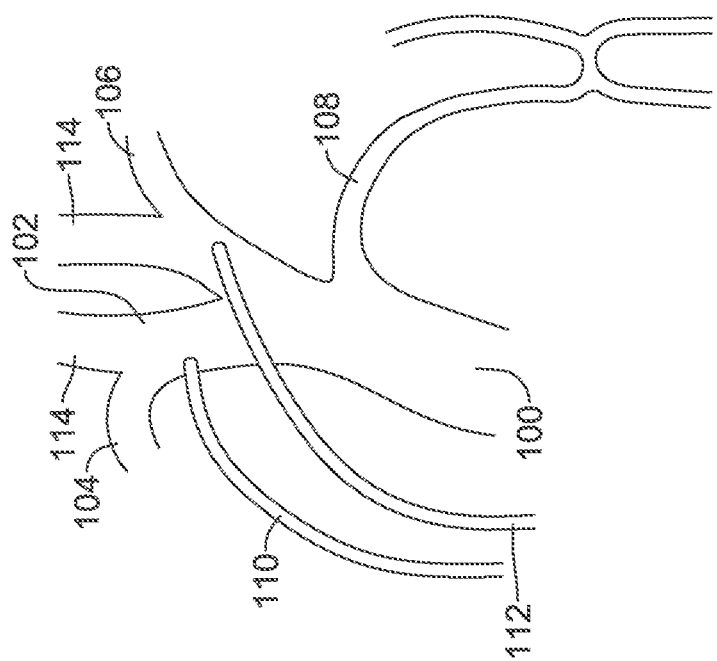
FIGS. 3A-3B show the ITVs and linked vasculature in isolation.
Figure 3A:
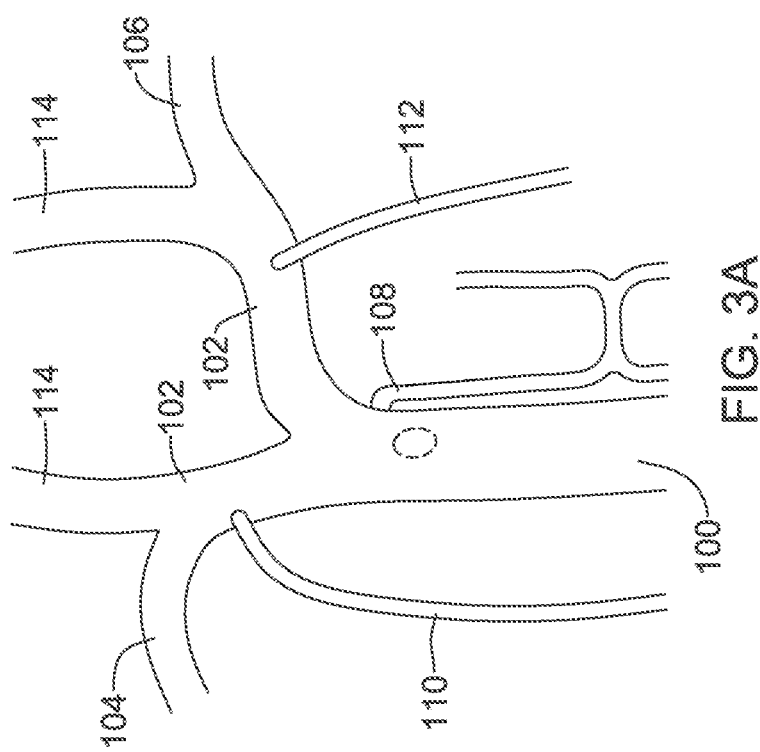

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is include in the illustration at 108, extending off the posterior of the SVC, and runs inferiorly posterior of the heart as can be understood from the lateral view of FIG. 3B. The right and left ITV are shown at 110, 112. These each branch off at a location that is considered part of the brachiocephalic veins 102. The internal jugular veins are also shown at 114.

Figure 4:
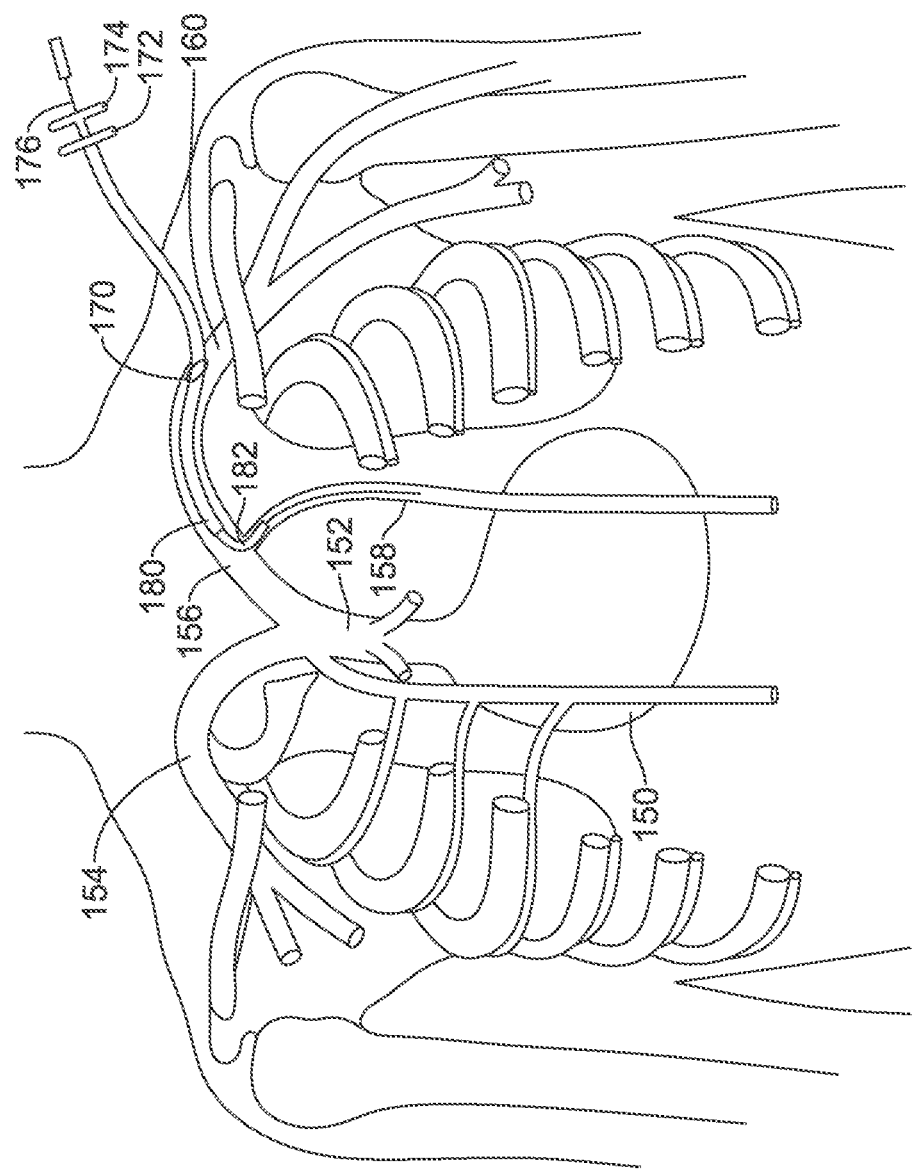

FIGS. 4-5 show superior access to and implantation of a lead in the ITV. Starting with FIG. 4, the heart is shown at 150 with the SVC at 152 and the brachiocephalic vein right branch at 154 and left branch at 156. Access to the subclavian vein 160 is shown at 170 using standard access techniques known in the art for implanting traditional transvenous pacemakers and defibrillators. For example, the Seldinger technique may be used by creating a puncture with a hollow needle or trocar, for example under ultrasound guidance, introducing a guidewire through the needle, removing the needle, and then inserting an introducer sheath 172, which may have a valve at its proximal end, over the guidewire. Other venipuncture or cutdown techniques may be used instead. Other vessels may be accessed instead of the subclavian vein using similar techniques including, for example, the jugular, cephalic, or axillary veins.

Into the access at 170, an introducer sheath 172 is inserted and advanced to a location to place its distal tip 180 near the ostium of the left ITV 158. Contrast injection may be useful to visualize the ITV structures and the ostia of the ITVs. A guide catheter 174 and guidewire 176 are then introduced through the introducer sheath 172. In other examples, a shorter introducer sheath may be used, with the guide catheter 174 used to traverse the distance to the relevant ostium.

The guidewire may be the same as used in gaining initial access 170 (if one is used to gain access 170), or may be a different guidewire. In an example, the guidewire 176 is preloaded in the guide catheter and both are introduced at the same time until the guide catheter 174 is at a desired location relative to the ostium of the selected ITV. The guidewire 176, which may be deflectable or steerable, can then be used to enter the left ITV 158 through the ostium thereof, passing down into the left ITV 158. The guide catheter 174 can then traverse over the guidewire and through the ostium and into the left ITV 158.

A device passing into the ITV from a superior position will need to pass through the valves of the ITV in a direction counter to their natural tendency (the veins prevent blood from flowing inferiorly). For an example where the guidewire passes unsupported by a guide catheter into the ITV from a superior position, the guidewire may preferably be stiff. In some examples, at least two guidewires may be used, a first more flexible and steerable guidewire to obtain initial access via the ostium of the ITV, and a second, stiffer guidewire that is sufficiently pushable to allow passage through the valves in the ITV.

In some examples, the guide catheter 174 is introduced first and the guidewire 176 is introduced next. For example, a steerable or curved guide catheter 174 may traverse the introducer sheath 172 to its distal end 180 and then, using steering of the guide catheter or a precurved structure of the guide catheter, would then turn as shown at 182 to enter the left ITV 158. The guidewire 176 may be introduced through the guide catheter 174. In another example, a guidewire 176 may be omitted.

FIG. 5 shows implantation of an implantable cardiac stimulus system. The system includes an implantable pulse generator 190 which may be placed in the subclavicular location shown (or any other suitable position, as desired). A lead 192 passes into the venous access point 170 into the subclavian vein 160 and to the brachiocephalic vein 156. The lead then enters the left ITV 158. For such an introduction, in one example, the guide catheter 174 (FIG. 4) can be used to direct the lead 192 through the ostium of the chosen ITV, with or without use of a guidewire 176 (FIG. 4).

In some examples, a flexible lead is used having a lumen therein to receive a guidewire or stylet to enhance pushability through the valves of the ITV 158. In another example, a flexible lead may be introduced with the support of the guide catheter 174 during advancement. In this latter example, the guide catheter 174 may receive the lead 192 through a guide catheter lumen that serves to retain a fixation apparatus or shape for the flexible lead, such as a 2-dimensional or 3-dimensional curvature (see FIGS. 10-11), tines (see FIG. 12), an expandable member (see FIG. 15), or hooks or a side-extending engagement structure (see FIG. 16). Anchoring may be provided using a separate apparatus that can be attached to the lead, such as that shown in U.S. Provisional Patent Application Ser. No. 62/237,755, titled FIXATION DEVICE FOR A SUBCUTANEOUS ELECTRODE, the disclosure of which is incorporated herein by reference.

In another alternative, the guide catheter 174 and guidewire 176 may be omitted by providing a lead with a flexible or steerable structure, and/or a lead configured for implantation using a steerable stylet. For example, a lead may be configured to be implanted using a steerable stylet in a lumen thereof, with the initial placement into the ostium of the left ITV 158 (or right ITV 210, if desired) at the distal end of the introducer sheath 172, possibly using contrast visualization, if desired. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device.

In the example, the lead 192 includes a multi-electrode distal structure as shown at 194. The structure includes a proximal coil 196A separate from a distal coil 196B. The coils 196A/B and canister 190 may serve as therapy delivery electrodes. As such there may be multiple therapy vectors such as between coil 196A and coil 196B, between either of coils 196A and 196B and the canister 190, or between a combination of two of the three therapy electrodes 196A, 196B and canister 190, and the third such electrode, such as by linking coils 196A and 196B in common as the anode or cathode relative to the canister 190. Coils may be used for defibrillation therapy and may be omitted if desired, as some examples provide pacing therapy using different electrode structures such as ring or partial ring electrodes.

A plurality of ring electrodes may be provided as shown at 198A, 198B, and 198C. Electrode 198C may also or instead be a tip electrode. Electrodes 198A/B/C may serve as sensing electrodes. The coils 196A, 196B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or U.S. Provisional Patent Application Nos. 62/245,757, 62/245,738, 62/245,762, 62/245,729, the disclosures of which are incorporated herein by reference.

In addition, one or more of the ring or tip electrodes 198A, 198B, 198C may be used for therapy delivery. In an example, defibrillation therapy may use coils 196A, 196B coupled in common as the opposing pole to the canister 190, while pacing therapy may use coils 196A and 198B as opposing electrodes for post-shock pacing therapy, with a still difference combination of electrodes used to provide ventricular pacing therapy for example by pacing between coil 196B and tip electrode 198C.

Line 202 is provided, illustratively, to separate the atria and ventricles. The lead 192 may be placed as shown such that the proximal coil 196A is about level with the atria, and distal coil 196B is about level with the ventricles, if desired. In some examples fewer or different electrodes may be provided on the lead 192 such as by excluding one or the other of the proximal coil 196A or distal coil 196B. Various designs are also shown herein.

Line 204 is provided to indicate the top of the heart, with the apex or bottom of the heart marked at 200. In some examples, one or more electrodes on the lead 192 are provided at or inferior to the apex 200, or at or superior to the top 204 of the heart. In the example shown, on the other hand, the electrodes are located generally between the apex 200 and top 204 of the heart.

The illustration shown in FIG. 5 places the lead on the left side 206 of the patient. In other examples, the right side 208 of the patient may instead or in addition be accessed, including the right ITV 210. Access to the right ITV 210 may be achieved by advancing a guide catheter and/or guidewire from the left subclavian access 170 as shown by arrow 212 across to the ostium of the right ITV 210.

Alternatively, access to the right ITV may be achieved as shown at arrow 214 by entering the right subclavian vein in a mirror image procedure of that shown in FIG. 4. In some examples, each of the left and right ITV 158, 210 may receive a lead 192. The lead 192 may be split (as shown relative to an inferior access route in FIG. 8B), a yoke may be provided near the canister 190 to join two leads together, or a header on the canister 190 may be configured to receive more than one lead 192, if desired, to provide leads in each of the left and right ITV 158, 210. If two leads are provided, use may be similar to that explained relative to FIG. 8A, except insofar as the leads may be implanted from the superior blood vessels as shown in FIG. 5. For example, pacing between right and left side lead placements may be performed to target specific chambers or chamber combinations, or sensing may be performed using one pair of electrodes with therapy delivery using a different pair of electrodes to achieve resynchronization or other desirable effect.

Figure 6A:
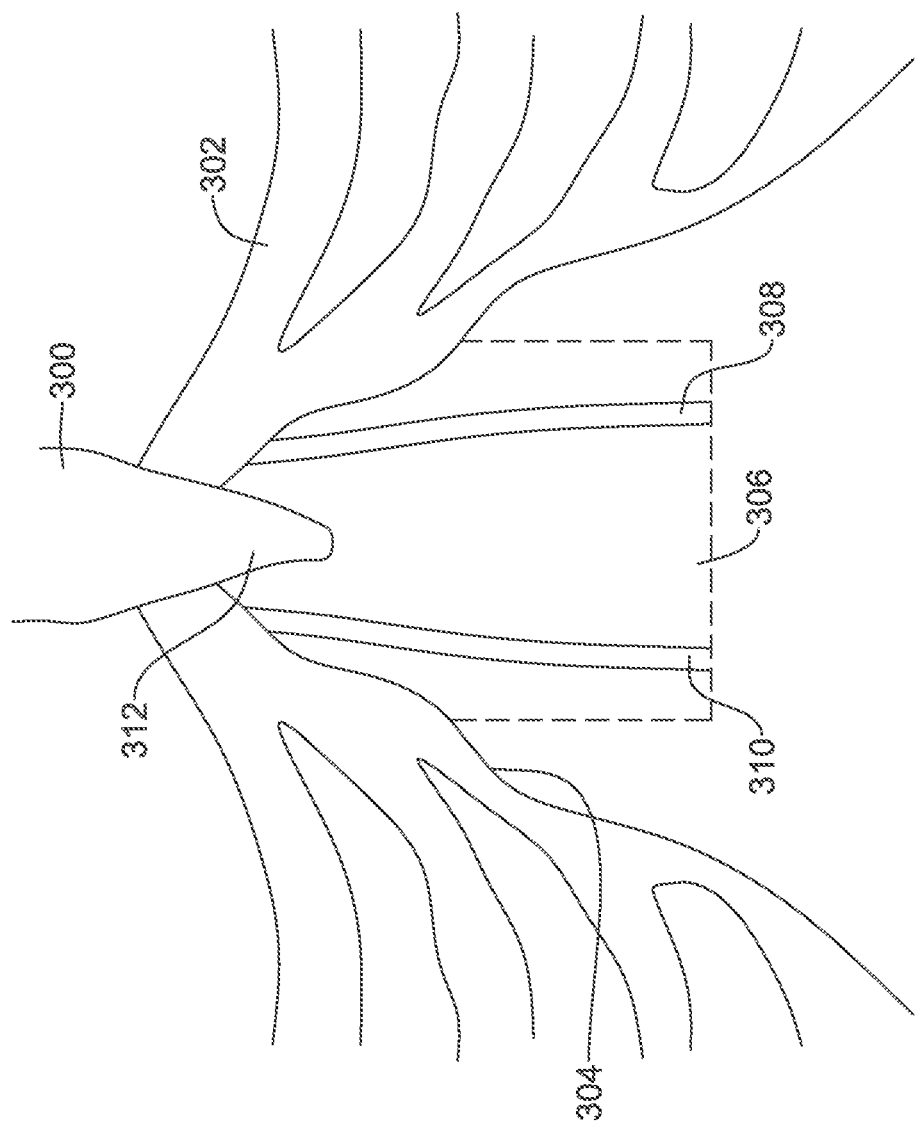
FIG. 6A shows in close view a location inferior to the lower rib margin where the ITV may be accessed inferiorly via the superior epigastric vein.

FIG. 6A shows in close view a location inferior to the lower rib margin where the ITV may be accessed inferiorly. This region may be referred to as the inferior thoracic aperture. The patient anatomy is shown in part including the sternum 300 and ribs 302, with the lower rib margin at 304.

A cutout area is shown at 306 in order to illustrate the approximate location for accessing the right or left ITV using the superior epigastric veins. The left superior epigastric vein is shown at 308, and the right superior epigastric vein is shown at 310. In order to access either vein 308, 310, a physician may palpate for the xiphoid process 312 and then use ultrasound guided access to obtain needle entry into the desired vein 308, 310 on the desired side of the xiphoid 312. This inferior approach preserves the upper thoracic vasculature in the event that the patient later needs a traditional transvenous, intracardiac system, or for use in other procedures. Such access may also reduce the potential for lead fracture such as that caused by subclavian crush. Once access to a selected superior epigastric vein 308, 310 is achieved, the vessel can be traversed in a superior direction to place the lead at a desired level by entering the corresponding ITV.

The access may generally resemble the well-known Seldinger technique, with an initial needle puncture using a hollow needle or trocar. A guidewire is passed through the hollow needle or trocar, which can then be removed. An introducer sheath, typically having a dilator therein and a valve at a proximal end thereof, is then inserted over the guidewire and into the desired blood vessel. The dilator and/or guidewire can then be removed, leaving in place the valved introducer sheath to allow introduction of interventional devices and/or a lead therethrough. At the conclusion of the lead implantation procedure, a sealing device such as a suture sleeve can be placed to seal the puncture site to the implantable lead left therein. The aim may be to access the ITV or superior epigastric vein at or near the $7^{th}$ rib margin in a window adjacent to the xiphoid process that may be described as a paraxiphoid window.

In another example, a cut-down technique may be used to access the desired vein 308, 310 by incision through the skin. Next, possibly after visual confirmation the desired vessel is accessed, incision into the selected vein can be made. In another example, anatomical landmarks such as the rib margin and/or infrasternal angle may be used to facilitate venipuncture into the desired vein 308, 310.

In animal testing the present inventors have determined that access to the ITV can be achieved with little difficulty to facilitate lead placement by accessing the superior epigastric vein in the region adjacent and inferior to the lower rib margin. However it is recognized that the human anatomy will be different from that of the tested animal (porcine model), and may further vary with the particular body characteristics of a given patient including, for example, any venous abnormality, scarring in the area (such as related to any prior sternotomy or the like) as well as the body habitus (overweight or underweight patients).

The musculophrenic vein (not shown) runs along the lower rib margin 308 and may instead, or also, be accessed in a manner that will be termed, for purposes herein, as an inferior access location as it would be inferior to the lowest rib. The musculophrenic vein and superior epigastric vein come together at the lowest end of the internal thoracic vein. Use of the musculophrenic vein may occur using similar methods as for the superior epigastric vein, if desired, including an ultrasound guided Seldinger technique. Due to its adjacency to a bony structure (the costal margin at 308), the musculophrenic vein may be useful as its access may be simpler than that of the superior epigastric vein (as the position can be readily ascertained) or the internal thoracic vein (as access would not require going through an intercostal).

Figure 6B:
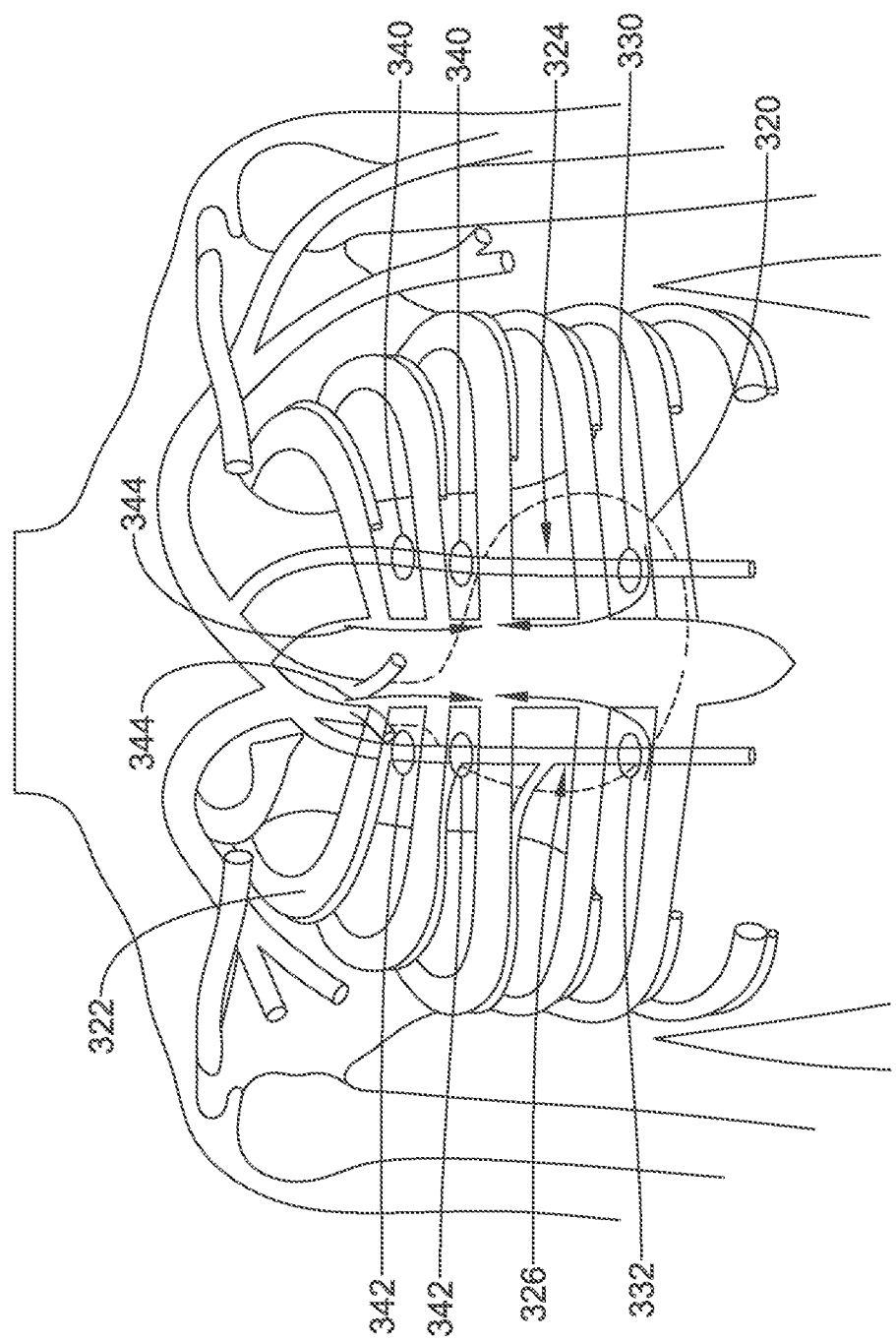
FIG. 6B illustrates intercostal access locations usable for superior or inferior access.

FIG. 6B illustrates some intercostal access locations usable for superior or inferior access. Such an access position may be labeled a parasternal access position. The Figure shows the heart at 320 beneath the ribcage 322. The right and left ITV are shown at 324 and 326. Any intercostal space overlying either of the right and left ITV may be a suitable point of entry, however, more superior or inferior positions may be preferred to allow passage of the distal end of a lead along a significant region of the ventricles and atria by passing in a single direction.

In the example shown, illustrative intercostal access locations are shown at relatively inferior positions 330, 332, and more superior positions 340, 342. In some examples, the inferior positions 330, 332, may be used with a left or right sided lateral implant canister position, such as using a lead passing through intercostal 330 with a left lateral canister. In some examples, the superior positions 340, 342 may be used with a left or right sided superior, or high pectoral, implant canister position, such as using a lead through one of the intercostals at 340 with a left sided, clavicular canister location. In some examples, tunneling up, down, or across the ribcage may be used to pair, for example, a superior intercostal access position with a more inferior canister location, such as by putting a lead through the left sided superior intercostal 340 and tunneling to/from that lead location for coupling with a left lateral axillary canister. In still other examples, the traditional implant position at the left clavicle may be paired with an intercostal access by tunneling, for example, down/across to one of the intercostals at 330, 332.

For any of these positions, 330, 332, 340, 342, access may be had using ultrasound guided needle insertion. Again, the access method may resemble the Seldinger technique, though in this case the muscle in the intercostal space would first be traversed. A needle may be used to establish puncture using ultrasound guidance, with a guidewire passed therethrough. Once the puncture is made and the guidewire is in the desired blood vessel, the needle is removed, keeping the guidewire in place, and an appropriately sized introducer sheath (optionally including a dilator) is placed over the guidewire.

The alternative in FIG. 6B allows access from either superior or inferior positions while preserving the upper thoracic vasculature. An advantage over the approach of FIG. 6A is that the use of a suture sleeve attachment with FIG. 6B would occur on the fascia over the ribcage near the intercostal access point, making suture sleeve use easier and avoiding movement between the point of venous system entry and the point of fixation. On the other hand, a user may be more comfortable accessing the veins at a location where the ribs and intercostal muscles do not interfere; thus, each of the various approaches herein has advantages and disadvantages relative to one another.

Figure 7:
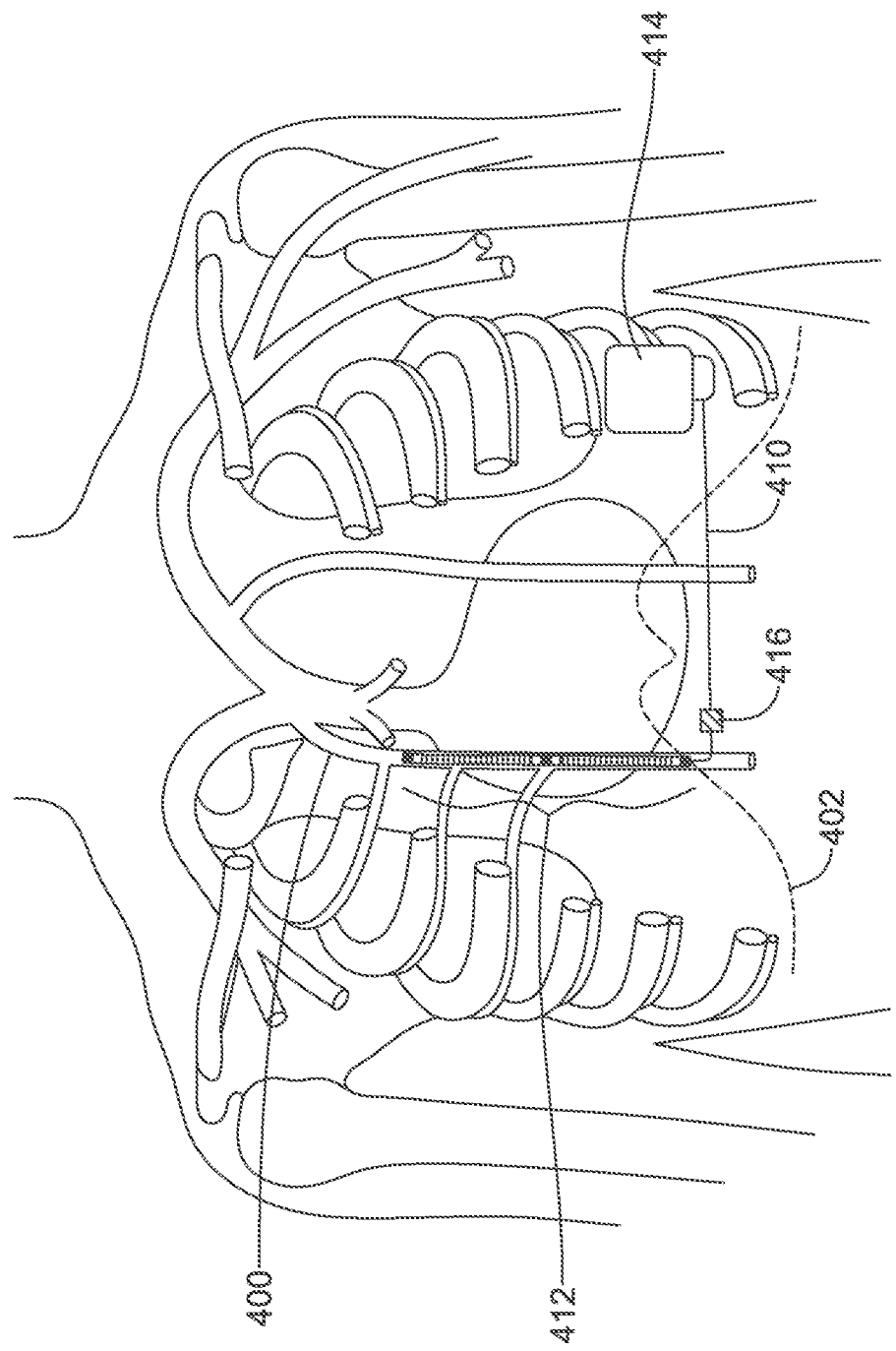
FIG. 7 shows implantation from an inferior position in a right ITV.

FIG. 7 shows implantation from an inferior position in an ITV. In this example, the right ITV 400 has been accessed by introduction through the superior epigastric vein from a location inferior to the rib margin 402. An implantable device has been placed including a lead 410 having a distal electrode structure 412 and a canister 414, with the canister 414 placed at approximately the left axilla. The canister 414 may be placed as desired, for example at the anterior axillary line, the midaxillary line, or in the posterior axillary line.

In the illustration, a suture sleeve is shown at 416 and is used to fixate the lead 410, for example, to the subcutaneous fascia. For placement, the right ITV 400 is accessed as described above, and a tunnel is established between the left axilla and the access location such as along a portion of the inframammary crease. The lead 410 may, in this case, be relatively stiff to assist in keeping it emplaced in the patient as shown, if desired. Various designs are shown herein for the lead as well, including tines, hooks, curvature or bias of the lead, and inflatable or expandable structures. In the example of FIG. 7, a left axillary canister location is shown; a right sided, pectoral or subclavicular left or right position may be used instead, in combination with the right ITV placement 400 or, alternatively a left ITV placement.

Figure 15:
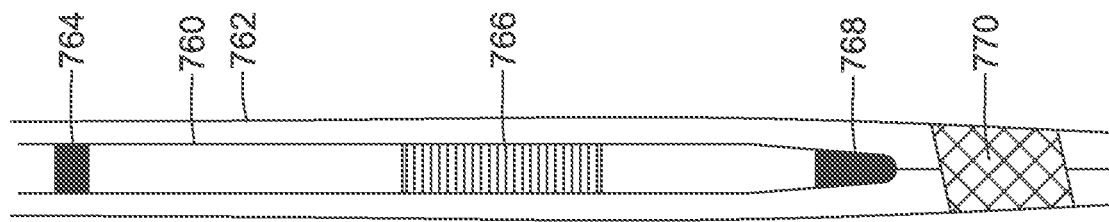
Figure 16:
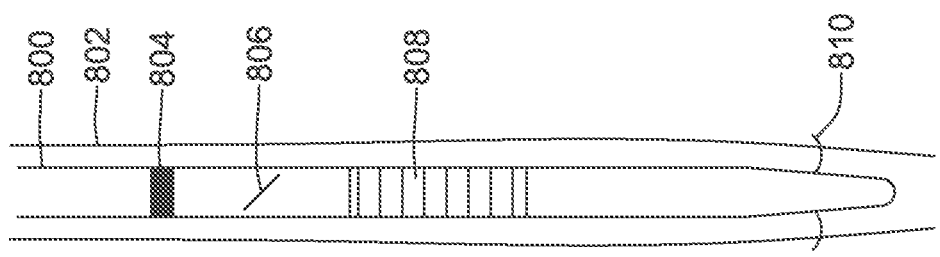

During implantation, a sheath may be provided over the lead 410, or at least a portion thereof, to retain or restrain a fixation apparatus or shape for the flexible lead, such as a 2 or 3 dimensional curvature (see FIGS. 10-11), tines (see FIG. 12), an expandable member (see FIG. 15), or hooks or a side-extending engagement structure (see FIG. 16). A stylet may be placed through the lead 410, or a portion thereof, to retain a straight shape during implantation; upon removal of the stylet, a curvature (see FIGS. 10-11) may then be released for securing the lead 410 in place.

The lead 410 may include additional or different electrodes than those shown. For example, another coil electrode may be placed on a more proximal portion of the lead 410 to reside along the inframammary crease in a location between the canister 414 and the point of access into the superior epigastric vein. The additional coil at this location may be used for defibrillation or other therapy purposes, or for sensing. If desired, second or more leads may also be placed.

Figure 8A:
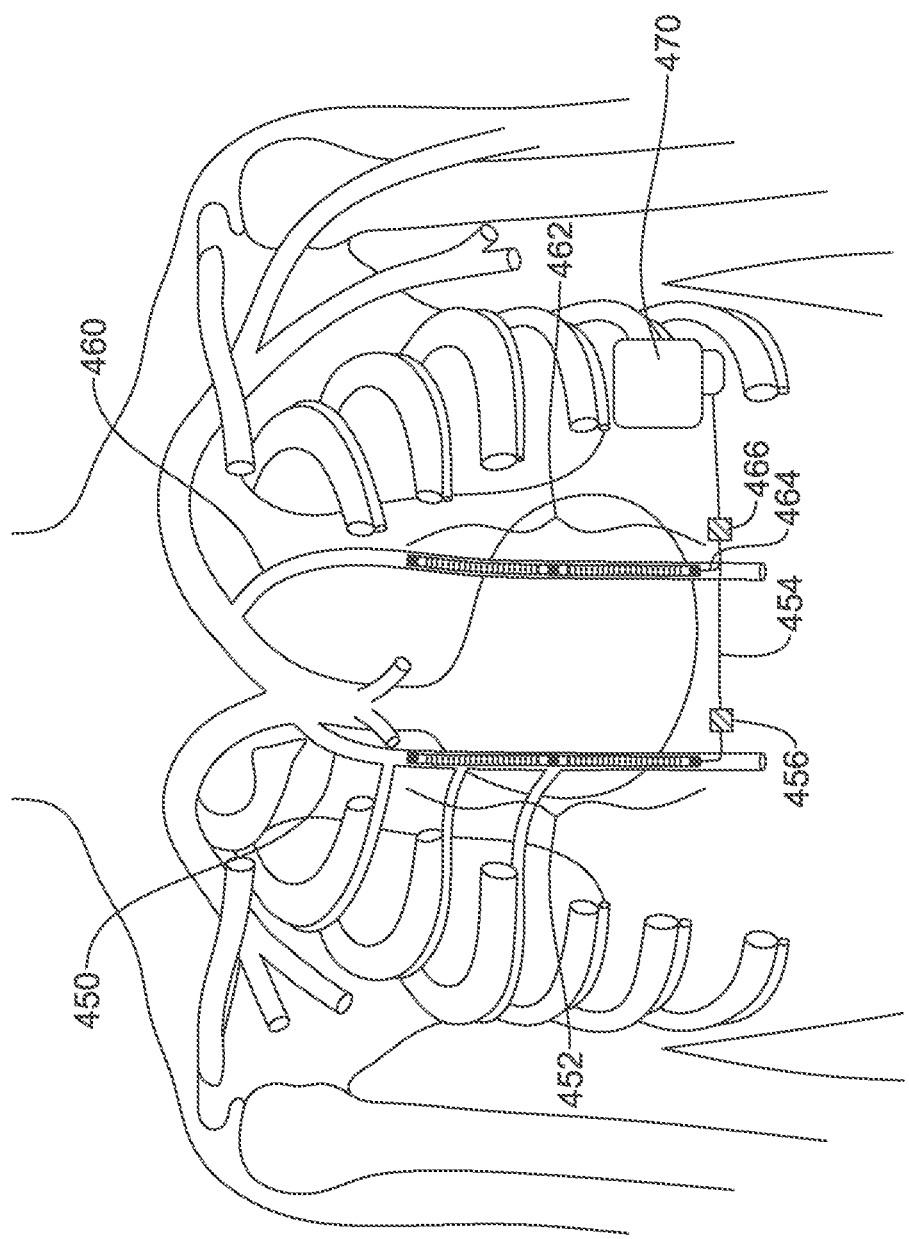
FIG. 8A shows implantation from an inferior position in both ITVs.

FIG. 8A shows implantation from an inferior position in both ITV. In this example, the right ITV 450 is shown with the electrode structure 452 on a distal end of a lead 454 disposed therein. A suture sleeve 456 secures the lead 454. The lead 454 includes a second branch that enters the left ITV 460 with a distal electrode structure 462 disposed therein. A second suture sleeve 466 optionally secures the lead 454 at a second location. A canister for the system is shown implanted in the left axilla. As noted above, the point of access to each of the right and left superior epigastric veins, in order to enter the right and left ITV 450, 460, may be placed close to the xiphoid process at the xiphsternal junction, and/or at or near the infrasternal angle. More inferior access to the superior epigastric veins may be used if desired.

FIG. 8B shows an illustrative lead that may be used in the implantation configuration of FIG. 8A. The illustrative lead 500 includes a proximal plug structure shown at 502, with a split at 510, from which a shorter branch having an electrode structure 504 extends, and a longer branch 508 continuing in the axial direction to another electrode structure 506. The design is illustrative and not intended to be limiting. In another example, two separate leads may be used, rather than one integrated lead.

As shown, each electrode structure 504, 506 includes a coil electrode flanked with two sensing electrodes; other combinations of electrodes may be used. Each electrode may be electrically connected to a single contact on the plug 502 or, if desired, subsets of electrodes may be ganged together relative to a single contact on the plug 502. The distal portion may include a fixation apparatus or shape for the flexible lead, such as a 2 or 3 dimensional curve (see FIGS. 10-11), tines (see FIG. 12), an expandable member (see FIG. 15), or hooks or a side-extending engagement structure (see FIG. 16).

Figure 9:
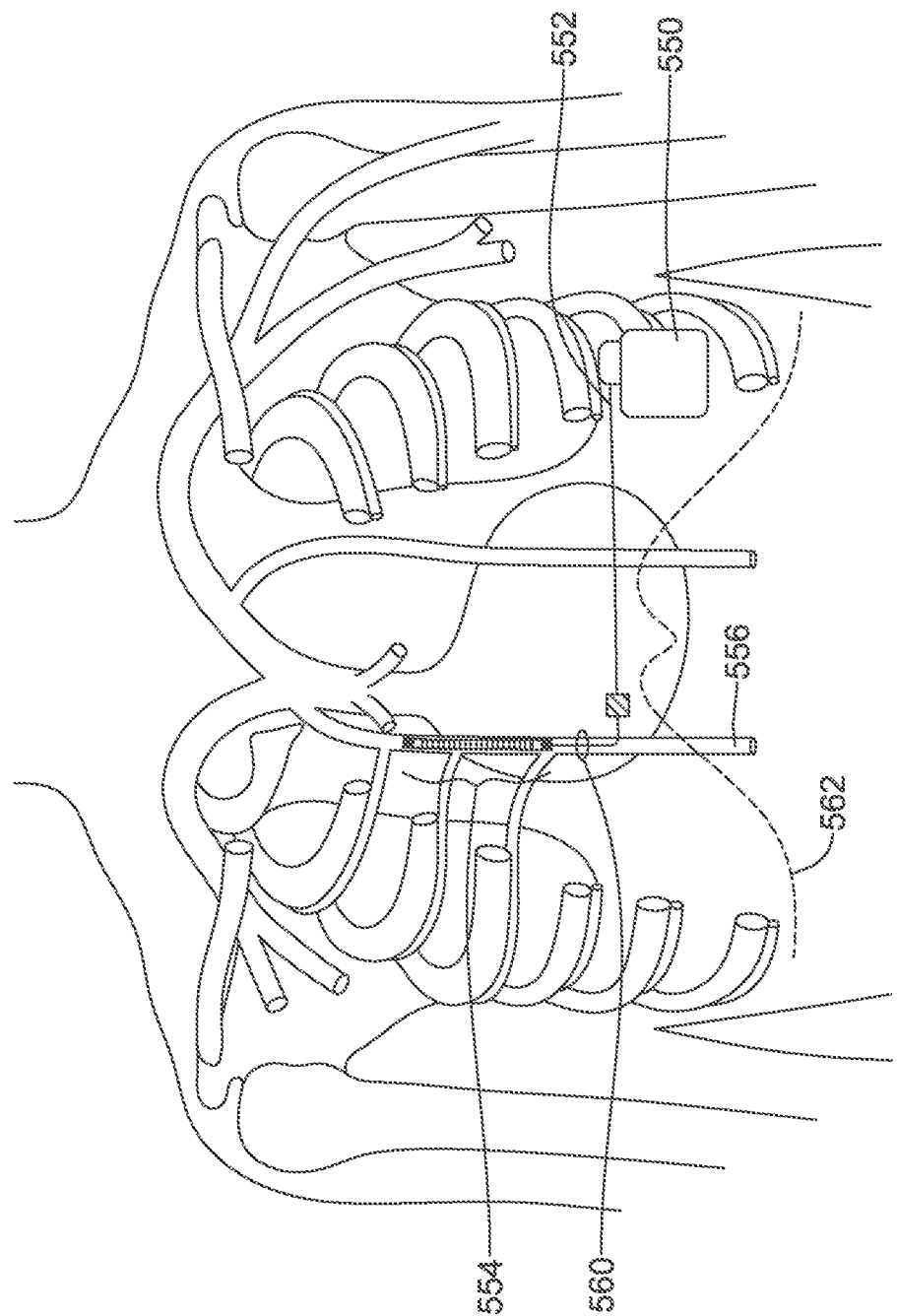
FIG. 9 shows implantation using an intercostal access to the right ITV.

FIG. 9 shows implantation using an intercostal access to an ITV. In this example, an implantable system having an implantable pulse generator 550 and lead 552 with distal electrode structure 554 has been emplaced in a patient. The right ITV 556 is accessed using an intercostal access point at 560.

The intercostal access 560 may be achieved by inserting a needle, preferably under guidance such as by the use of an ultrasound guided needle, into a chosen intercostal space, preferably low on the ribcage and near the sternum, through the muscle of the intercostal space and into the right ITV 556. A guidewire can be passed through the needle and an introducer sheath passed over the guidewire after removal of the needle. Other techniques may be used instead, and other access points may be selected.

In one example, the musculophrenic vein may be used. The musculophrenic vein runs along the lower rib margin and may be accessed in a manner that will be termed, for purposes herein, as an inferior access location as it would be inferior to the lowest rib. The musculophrenic vein and superior epigastric vein come together at the lowest end of the internal thoracic vein. Due to its adjacency to a bony structure (the costal margin), the musculophrenic vein may be useful as its access may be simpler than that of the superior epigastric vein (as the position can be readily ascertained) or the internal thoracic vein (as access would not require going through an intercostal).

A suture sleeve may be used to secure the lead 552 over the ribcage as desired. The lead 552, as with all other implanted leads shown herein, may include a fixation structure such as bends or curves along its distal length, or tines, hooks or expandable members at its distal end to secure its position within the ITV 552.

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

The above examples facilitate a number of therapy options. For example, defibrillation therapy may be delivered in various configurations such as, without limitation:

Between a left ITV electrode or combination of electrodes and a right ITV electrode or combination of electrodes;

Between a left ITV electrode and a device housing placed in the left axilla or left subclavicular location;

Between a right ITV electrode and a device housing placed in the left axilla or left subclavicular location;

Between a left ITV electrode and a device housing placed in the right axilla or right subclavicular location;

Between left and right ITV electrodes electrically in common and a right or left axillary or subclavicular canister.

Between one ITV electrode and a second ITV electrode in common with a device canister in the left or right axilla or subclavicular location Between a first electrode on a lead, and a second electrode on the same lead, where the first and second electrodes are in the same ITV Between a first electrode on a lead, and a second electrode on the same lead, where the first electrode is in an ITV, and the second electrode is in a tunnel leading to access to the ITV, such as in the inframammary crease on lead 410 in FIG. 7

In these examples, a "left ITV electrode" or "right ITV electrode" may include a single coil electrode or a combination of plural coils and/or one or more coils with one or more ring electrodes electrically in common. The above combinations may also be used for delivery of a bradycardia pacing therapy or an anti-tachyarrhythmia pacing therapy.

Further examples may provide a resynchronization therapy by delivering pacing pulses in various configurations, such as, without limitation:

In bipolar fashion within the left ITV to pace the left ventricle, and also in bipolar fashion within the right ITV to pace the right ventricle, with relative timing between the two sets of pacing therapies determined according to analysis of cardiac output or electrical response.

In bipolar fashion within one of the left or right ITV to stimulate a respective left or right ventricle in response to atrial sensed signals sensed with electrodes placed in an ITV at a superior location level with the atria.

In monopolar fashion between a device housing and one or both of left or right ITV electrodes, using for timing information atrial signals sensed using additional electrodes in at least one ITV and/or far-field sensed morphology detected using a device housing.

In an example, a heart failure or resynchronization therapy may be delivered as follows, with reference to FIG. 7. A pacing therapy may be delivered by sensing atrial activity using the distal two ring electrodes shown in the electrode assembly 412 to determine timing for pace therapy delivery using the proximal coil electrode and canister 414. Numerous other combinations may be had as can be seen to those skilled in the art.

FIGS. 10-18 illustrate various lead designs. These leads may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection. Some illustrative lists for such design details follow later in the disclosure.

Figure 10:
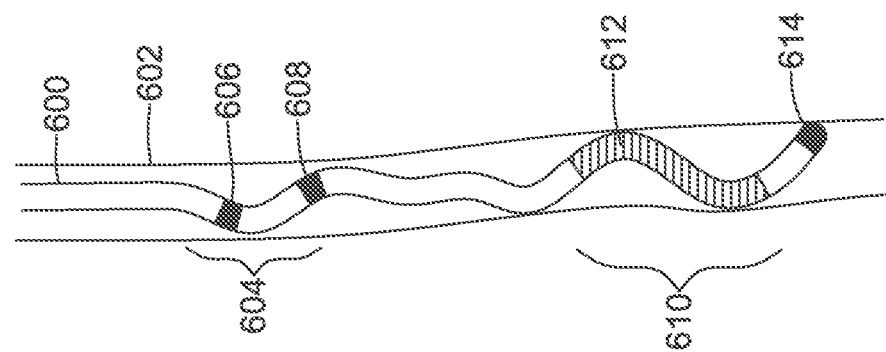

FIG. 10 shows an illustrative lead structure. A lead 600 is shown within a blood vessel 602, which may be an ITV. The lead may include ring electrodes illustrated at 606, 608, and a tip electrode 614, as well as a coil electrode at 612. Regions of curvature area shown at 604, and at 610. A single curvature may be provided instead. The curvature may be two-dimensional or three-dimensional. A two dimensional curvature may take the form, generally, of a zig-zag design, for example. Several embodiments may use a three dimensional curvature such as a pigtail or helix, for example.

In one example, the distal tip 614 is implanted inferior relative to the rest of the lead, such that the coil 612 is adjacent or level with the patient's ventricles. In another example, the distal tip is implanted superior relative to the rest of the lead, such that the coil 612 is adjacent or level with the patient's atria. In another example, the position of coil 612 is switched with the position of ring electrode 608, such that if implanted with the tip 614 superior relative to the rest of the lead, the tip 614 would be at about the level of the atria (or higher), while the coil 612 would be adjacent to or level with the ventricles.

Figure 11:
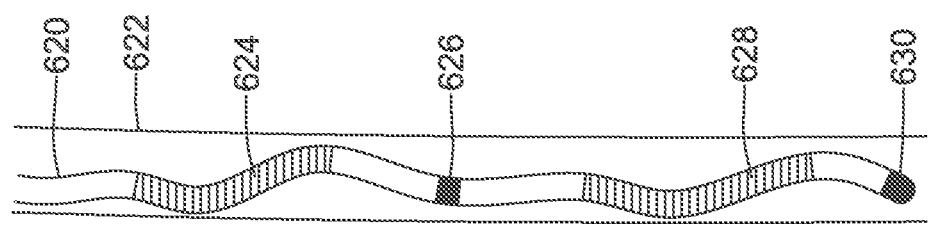

FIG. 11 shows another example. A lead 620 is shown within a blood vessel 622, which may be an ITV. The lead may include ring electrode 626 and a tip electrode 630, as well as coil electrodes 624, 628. An additional ring electrode may be placed proximal of the coil electrode 624, as shown above in FIG. 5, if desired. With this example, the coils 624 may be spaced and positioned such that one is level with the ventricles and the other is level with the atria when implanted with the tip 630 either superior or inferior. As with FIG. 10, FIG. 11 shows that the lead has several areas of curvature.

In FIGS. 10 and 11, the curvature may be assumed by the lead in several ways. In an example, the lead includes a shape memory material and is generally straight and flexible until implanted in the body; after a few minutes to warm up, the shape memory material assumes the shape shown. In another example, a stylet is placed inside the lead during implantation to retain a generally straight shape, and the lead assumes the curved shape shown when the stylet is removed. In another example, an outer sheath is used to retain the lead until it is implanted with removal of the outer sheath allowing the lead to assume a desired shape. Combinations may be used as well; for example, a lead may include a shape memory portion or material or support structure, and may be implanted with the aid of a stylet and outer sheath to retain a low profile for implantation and then, once released by removal of the stylet and sheath, the shape memory material exerts forces to assume the shapes shown. Though not shown, curvature may be used for secure placement of any of the leads shown in FIGS. 12-18, if desired.

Figure 12:
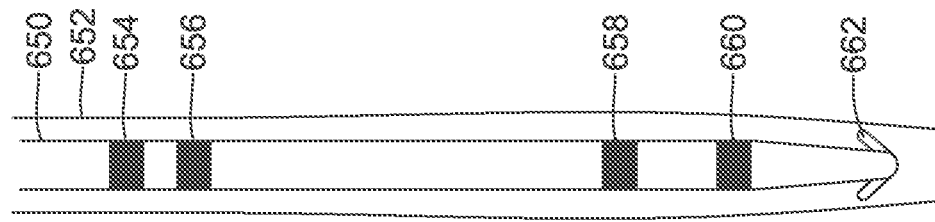
FIGS. 10-18 illustrate various lead designs.

FIG. 12 shows another example. Here, a lead 650 is shown inside a blood vessel 652, which may be the ITV. First and second ring electrodes are shown at 654, 656, and third and fourth ring electrodes are shown at 658, 660. Tines for fixation are shown at 662. The ring electrodes may be placed such that if the tines 662 are superior relative to the rest of the lead, electrodes 658, 660 would be level with the atria, and electrodes 654, 656 would be level with the ventricles. This may facilitate separate atrial and ventricular sensing and/or pacing channels. A coil electrode may also be provided.

In one example, a lead as shown in FIG. 12 is implanted in the left ITV while a separate lead is implanted in the right ITV, with the right ITV comprising a defibrillation coil electrode, with an active canister defibrillator implanted in the left axilla. This approach would allow sensing (and optionally, pacing) directly over the heart using the ring electrodes 654, 656, 658, 660, with defibrillation delivered across the majority of the myocardium between the right-sided coil electrode and the left sided canister.

Figure 13:
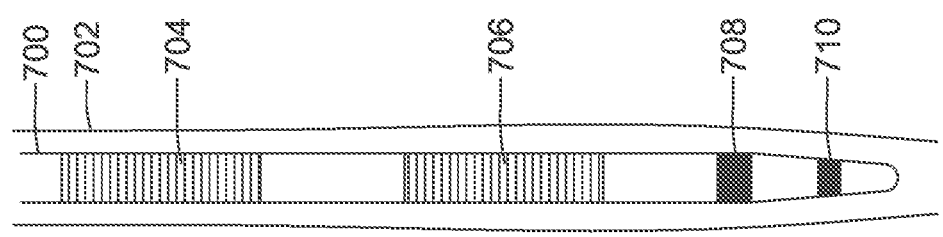

FIG. 13 shows another example. Here a lead 700 is implanted in a blood vessel 702 which may be an ITV. A first coil is shown at 704 and a second coil is shown at 706, with two distally located ring electrodes. If desired, the lead may taper as shown, though a fully cylindrical lead may be used instead. The taper may be useful during implantation to facilitate easier access through venous valves, particularly for insertions from superior to inferior, where the direction of insertion is counter to blood flow and hence valve structure. Curves or tines may be added, as well as other fixation features noted herein.

Figure 14:
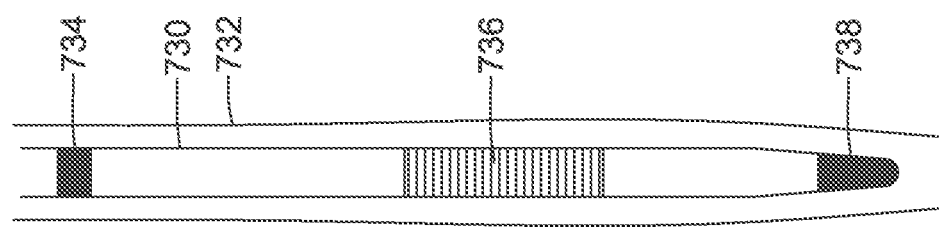

FIG. 14 shows another example. In this example, a lead 730 is shown inside of a blood vessel 732 which may be an ITV. A proximal ring electrode is shown at 734 and a coil at 736, with a distal tip electrode at 738. Curvature or tines may be added, as well as other fixation features noted herein.

FIG. 15 shows another example. Here, the lead is much as in FIG. 14, with lead 760 shown inside a blood vessel 762 which may be a ITV, and with a proximal ring electrode 764, coil electrode 766, and distal tip electrode 768. However, now, an expandable member, such as a stent 770 is shown distal to the distal tip electrode 768. For example, a self-expanding stent 770 may be provided and carried within the distal tip electrode 768 until a desired position is reached for the stent 770. Such positioning may be determined using, for example, fluoroscopy. The proximal end of the lead may include a release mechanism, such as a control wire that can be advanced relative to the lead body, to push the stent 770 beyond the distal tip electrode 768 where it can then release. Self-expanding stents are well known in the art and may include, for example, spring-like structures. The stent 770 may include coatings designed to prevent thrombus from forming thereon and/or to encourage angiogenesis to best engage the venous wall. For removal, the connection to the stent 770 may be cut, for example, to leave the stent 770 in place as the rest of the lead is removed. Optionally the stent may be later removed using, for example, a stent retriever.

FIG. 16 shows another example. Here, a lead 800 is shown in a blood vessel 802 which may be an ITV. A proximal coil electrode is shown at 804. Distal of the proximal coil electrode (though any suitable location, more proximal or more distal, may be chosen), a side-engaging member is shown at 806. For example, engaging member 806 may be an arm, coil, hook, or tine that expands outward when actuated from the proximal end of the lead. Once the lead is in a desired position, engaging member 806 may be actuated to secure the lead in place.

The lead 800 is also shown with a coil electrode at 808. Finally, at the distal tip of the lead, a plurality of hooks are shown for engaging the walls of the blood vessel 802. The engaging member 806 or hooks 810 may be coated as desired for anti-thrombogenic or pro-angiogenic reasons, for example.

Figure 17:
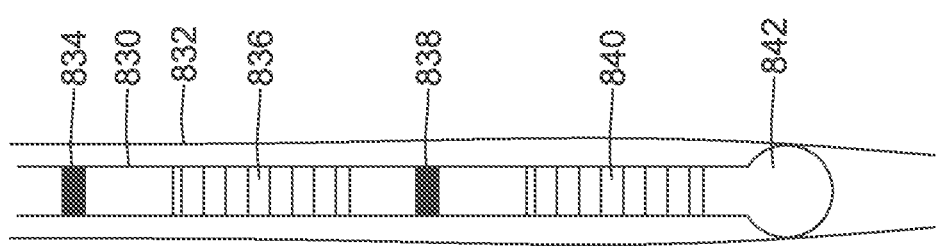

FIG. 17 shows another example. Here, a lead 830 is shown inside of a blood vessel 832 which may be an ITV. A plurality of electrodes are shown including a ring electrode 834, coil electrode 836, ring electrode 838, and coil electrode 840. At the distal end of the lead is an expandable member, such as a balloon, which may be inflated to secure the lead in place. It should be noted that the ITV is a blood vessel which, if occluded, will not necessarily cause harm to the patient as contralateral accommodation occurs readily. The balloon 842 may be expanded using inflation pressure, for example. A compliant or non-complaint material may be used the balloon. Rather than a balloon, an expandable sponge-type member that increases in volume once sufficiently wetted may be used instead.

Figure 18:
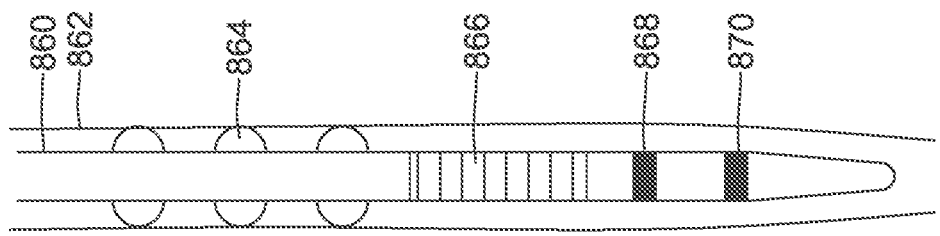

FIG. 18 shows another example. In this example, the lead 860 is shown in a blood vessel 862 which may be an ITV. This example includes a plurality of lobes 864 which hold the lead 860 in place inside the blood vessel 862. For example, the lobes may self-expand on removal of an outer delivery sheath or catheter, or the lobes may be expanded by movement of an outer shell of the lead relative to an inner shell. A coil electrode is shown at 866 and ring electrodes are shown at 868, 870.

The examples of FIGS. 10-18 are merely illustrative. Some examples may omit any fixation on the portion of the lead that extends into the blood vessel, and may instead rely on fixation using a suture sleeve subcutaneously placed as shown in certain of the above examples. In some examples, a relatively stiff lead may be used, as repeated flexion is not necessary when implanted in the ITV in the same manner as is the case inside the heart. A stiff lead is believed to be less likely to migrate.

Figure 19:
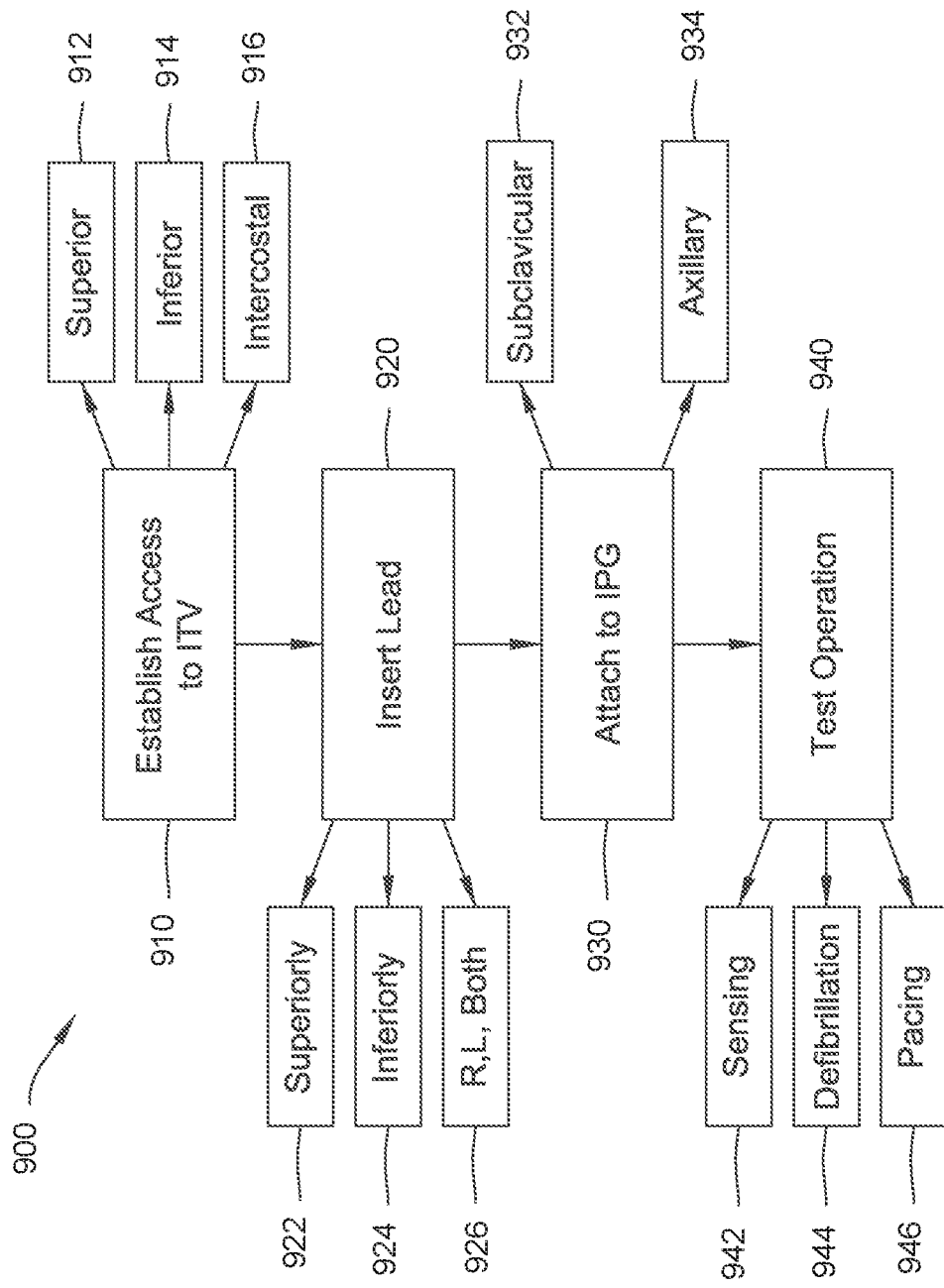
FIG. 19 is a block flow diagram for an illustrative method.

FIG. 19 is a block flow diagram for an illustrative method for providing a cardiac stimulus system to a patient. As shown at 900, the method comprises establishing access to the ITV 910, inserting a lead in the ITV 920, attaching an IPG to the lead 930, and performing test operations 940.

For example, establishing access to the ITV 910 may include accessing from a superior position 912 such as by entering the subclavian vein and passing through the ostium of the ITV in the brachiocephalic vein. In another example, establishing access to the ITV 910 may include accessing from an inferior position 914 such as by entering the superior epigastric vein and passing superiorly therefrom into the ITV. In some examples, access via locations 912, and 914 may include accessing via a second blood vessel such as by accessing superiorly 912 by way of the subclavicular vein and brachiocephalic vein, or accessing inferiorly 914 through the superior epigastric vein. In still another example, establishing access to the ITV may include accessing in an intercostal space 916 such as by penetrating an intercostal space and entering the ITV using a Seldinger technique.

In an example, inserting a lead 920 may include insertion superiorly 922, such as by starting in an inferior position 912 inferior to the lower rib margin or intercostally 916 from an inferior intercostal location, and advancing the lead in a superior direction. For another example, inserting a lead 920 may include insertion inferiorly 924, that is starting at a superior location 914 or at a superior intercostal location 916, and advancing the lead in an inferior direction. In either such example, the right ITV, left ITV, or both ITV vessels may be used, as indicated at 926.

In an example, attaching to an IPG may include attaching to a canister located in a subclavicular location 932, historically a common place to put an implanted canister for a transvenous defibrillator or pacemaker. In another example, attaching to an IPG may include attaching to a canister located in an axillary position 934, such as that used with the S-ICD System. Other IPG locations may be used. Attachment may be directly to the IPG or to a splitter, yoke, or lead extension, if desired.

In an example, test operation 940 may be used to verify one or both of device functionality and efficacy. For example, sensing operations 942 may be tested and configured to check for adequate signal availability, for example, or by setting gain, filtering, or sensing vector selection parameters. Defibrillation operations 944 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 944 may include determining for a given patient an appropriate defibrillation threshold, and setting a parameter for therapy delivery at some safety margin above the defibrillation threshold.

Prior transvenous systems would typically deliver up to 35 Joules of energy, with storage of up to 40 Joules of energy, using peak voltages in the range of up to 1000 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). As is known in the art, the therapy energy level may be selected or adjustable by a physician, or may be preset to a level expected to be sufficient for most patients.

Pacing thresholds may also be closer to those for traditional transvenous systems than the more recent S-ICD System. In an example, pacing testing operation 946 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

Figure 20:
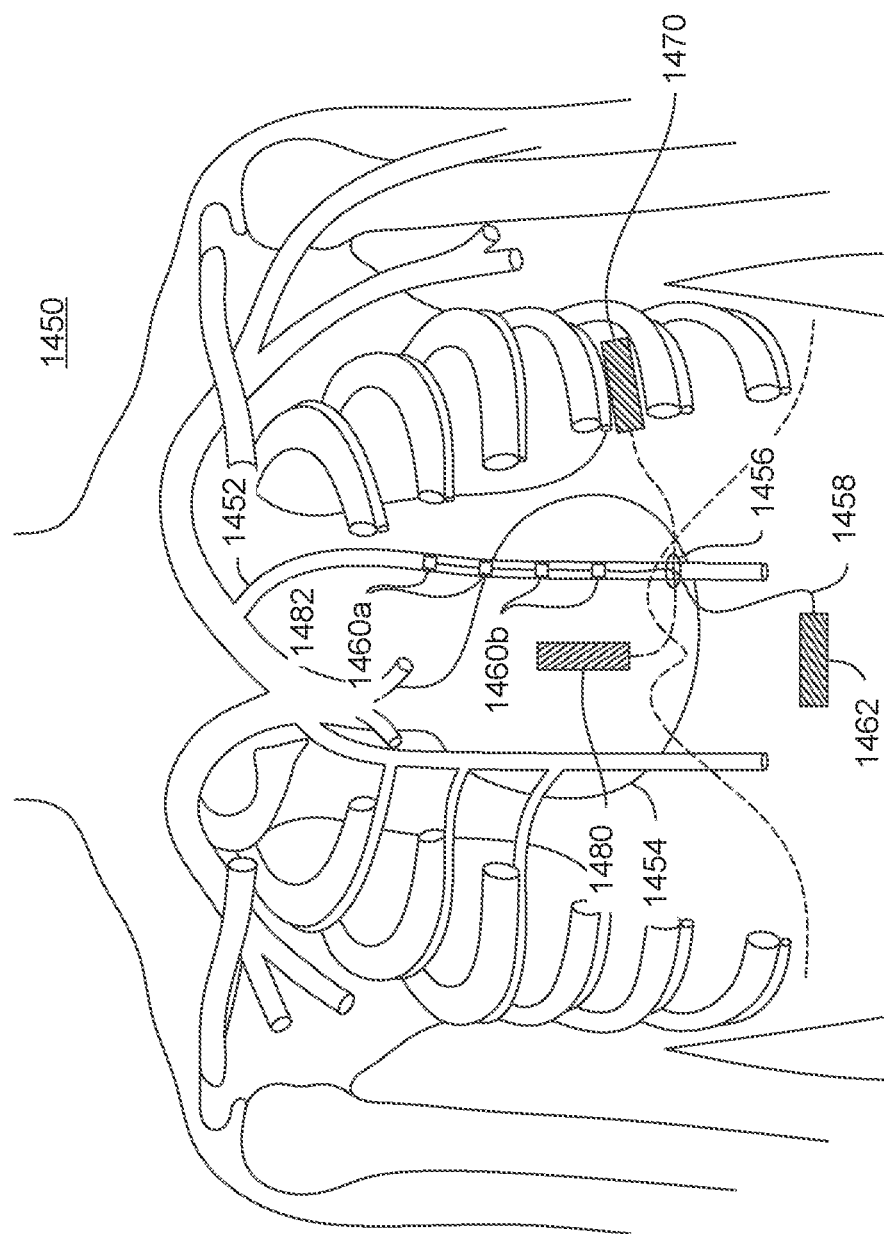
FIG. 20 shows implantation using intercostal access to a left ITV with a plurality of optional locations for a reduced size housing illustrated.

FIG. 20 shows implantation to a left ITV with a plurality of optional locations for a reduced size housing illustrated. In the illustrative example shown, a patient 1450 is shown with the left ITV shown at 1452 and the heart shown in phantom at 1454. The left ITV 1452 has been accessed using methods discussed above, such as by a Seldinger technique using an ultrasound needle, at or inferior to the lower rib margin as shown at 1456 using, for example, the superior epigastric vein (as discussed above) or the musculophrenic vein (similar to FIG. 35, below). A lead 1458 is shown with a distal portion thereof having electrodes 1460A/B that reside in the left ITV 1452 of the patient 1450. The lead 1458 is attached to a housing 1462 that is implanted, in this example, in the abdomen of the patient.

Alternative positions are shown for the housing 1462. In an example, the housing may be placed as shown at 1470, along an intercostal space. In the example shown, the fourth intercostal space has the housing 1470. The third or fifth intercostal spaces may be used instead; in some example, the housing 1470 may be even more inferior and lateral and placed in the sixth intercostal space. The implant position here may be subcutaneous or submuscular, depending on the position relative to the pectoral muscle. If the housing 1470 has an electrode on it that is to be used for therapy delivery, it may be preferable to place the housing 1470 in a submuscular position, where relevant. In some examples, the submuscular placement may be preferred in order to make the presence of the housing 1470 less visible. Alternatively, if the housing 1470 has a rechargeable battery, it may be preferred to provide the housing 1470 more superficial, either at a position where there is little subcutaneous tissue, or in a supra-muscular position.

Another alternative position is shown with the housing 1480 directly over the sternum 1482. This position may be more apparent to the patient, however, it is likely to be highly repeatable across various patient body compositions. In addition, such positioning would be superficial making charging of a rechargeable device easier.

The lead 1458 has a proximal end at the housing 1462 and includes a plurality of electrodes 1460A/B at a distal end thereof. In the example shown, four electrodes 1460A/B are shown. The electrodes 1460A/B may be ring electrodes, half-ring electrodes (or other partial electrodes), cap electrodes, coil electrodes, or other designs. More or fewer electrodes 1460A/B may be provided. In some examples, different electrodes may serve different functions. In FIG. 20, for example, the two more superior/distal electrodes 1460A may be configured as atrial sensing electrodes, while the two more inferior/proximal electrodes 1460B may be used for ventricular pacing. The electrodes 1460A/B may be used in other configurations as desired.

FIGS. 20-27 show several illustrative examples with smaller implantable pulse generator housing that may be adapted for pacing or monitoring cardiac rhythms, without defibrillation circuitry included. In some examples, the implantable medical device 1462, 1470, 1480 may take the form of a pacemaker, having output circuitry for providing one or more of anti-tachycardia pacing (ATP), bradycardia pacing, post-defibrillation asystole pacing, and/or cardiac resynchronization therapy (CRT). This may facilitate a reduced volume for the device housing 1462, 1470, 1480, as high power capacitors and charging circuitry used in an implantable cardioverter defibrillator (ICD) may be omitted, and the batteries used may be smaller and/or lesser in number than in an ICD. Further discussion of size and shape is included below relative to FIGS. 26A-26D. Other examples may further include defibrillation circuitry and capability.

A primary cell, or non-rechargeable battery may be used as is generally the case for conventional implantable pacemakers, or, if desired, a rechargeable battery may be used instead. The provision of a rechargeable battery may call for inclusion of a charging coil to allow inductive charging to be performed, though RF charging maybe used instead if desired. As noted above, positioning may be a consideration for a rechargeable system, as the depth of implant can affect the ability to recharge the implanted device quickly. Select examples related to a rechargeable device approach are discussed further below. Rechargeable devices may include, for example, zero volt recharge protection, recharge control and inductive coil circuitry, and may be used in association with wearable or other chargers; some illustrative examples are shown and discussed in U.S. Pat. Nos. 8,543,216, 8,386,048, 7,962,222, 7,818,068.

The lead design may be sized in the range of about four to about ten French, with it being envisioned that a lead in the range of about six to about eight French is likely to work in many patients. The ITV, generally speaking, is in the range of about three mm diameter (nine French) at about the 5th rib, getting larger in the superior direction. The pacing electrode on the lead may be sized in accordance with conventional pacing electrode sizes, or may have other dimensions as further described below. Plural pacing electrodes may be placed on a lead to allow bipolar pacing (pacing between two electrodes on a lead), or, if desired, monopolar pacing (pacing between one electrode on a lead or a plurality of electrically linked lead electrodes and a device housing) may be used. Pace therapy may be monophasic, biphasic, or other multi-phasic.

Illustrative pacing therapy may be current controlled with currents in the range of about 10 to about 50 milliamps for a first example. In another example, a current controlled output of about 15 to about 40 mA may be provided or available. In other examples, pacing therapy may be voltage controlled, with output voltages in the range of about 2 to about 40 volts in one example, or about 10 to about 30 volts in another example.

Bradycardia pacing systems may include a pace threshold test function to ensure adequate capture without undue energy usage, so a range of current or voltage levels may be available in a given device to account for various patient possibilities. For example, at intervals or in response to request or event, a device may test a variety of pacing output amplitudes or energies, varying, for example, current or voltage level/peak, delivered energy, and/or pulse width, while monitoring for evoked response of the heart to determine a pacing threshold of the patient. Once a pacing threshold is known, the device can then set its therapy output using the measured threshold and, typically, a safety margin.

Figure 21:
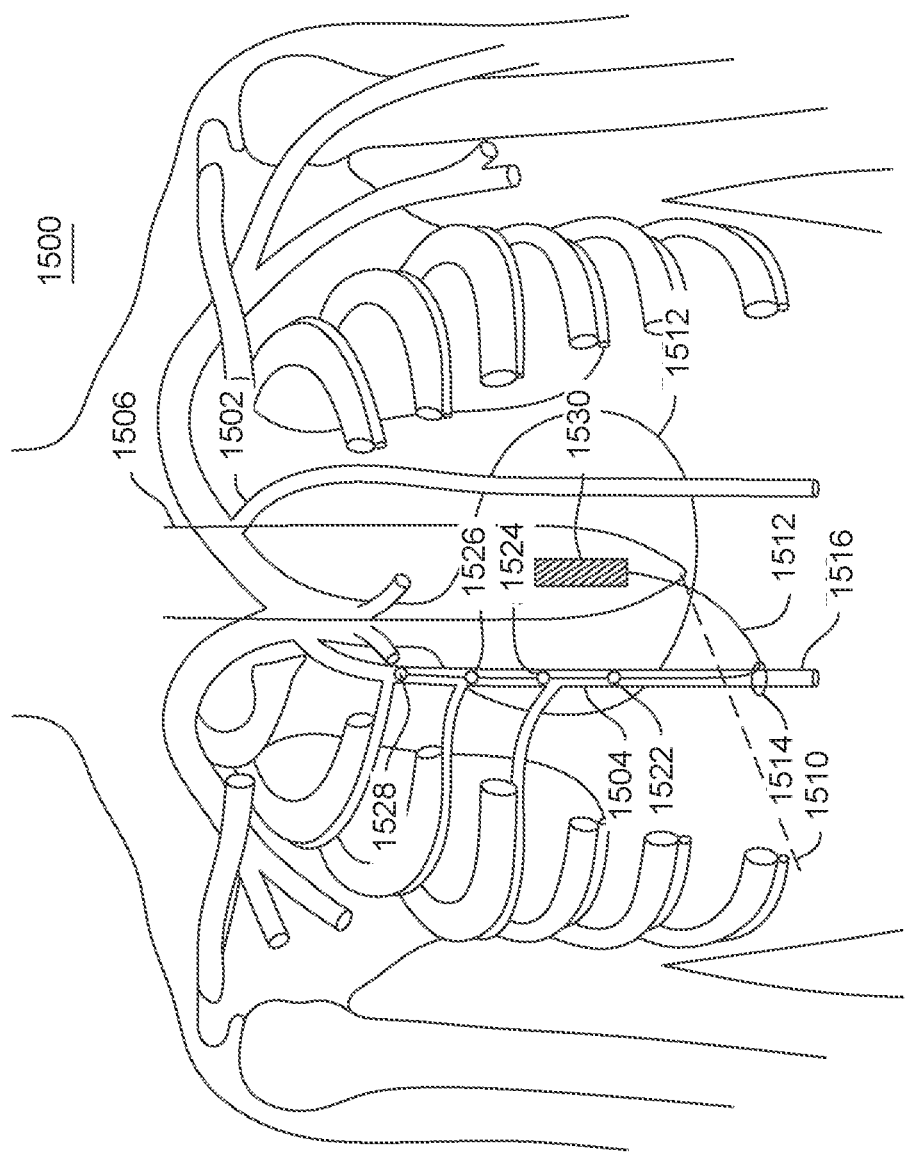
FIG. 21 shows implantation using a sternal housing location with an inferior access to the right ITV.

FIG. 21 shows implantation using a sternal housing location with an inferior access to the right ITV. In this example, the patient 1510 has a left ITV at 1502 and right ITV at 1504. The sternum is shown at 1506, with the inferior rib margin illustrated at 1510 and the heart at 1512.

In this example, the right ITV has been accessed at 1514, in the superior portion of the superior epigastric vein 1516, inferior to the rib margin 1510. A lead 1520 has a proximal end attached to a housing 1530 which has been placed over the sternum 1506. The sternal placement provides a readily repeatable position landmark for placement of the housing 1530. A suture sleeve may be used at the access point 1514 to hold the lead 1520 in position relative to the right ITV 1504.

The lead 1520 includes four electrodes 1522, 1524, 1526, 1528 in this example. Again, the inclusion of four electrodes is optional. In some examples, the electrodes 1524, 1526 may be replaced by a single electrode instead. In some examples, atrial sensing may be provided by the more distal electrodes 1526, 1528, which are more superior relative to the heart 1512, with therapy in the form of ventricular pacing provided by the more proximal electrodes at 1522, 1524.

Pacing electrodes may be similar in size and design to conventional pacemaker electrodes used in transvenous lead systems. For example, the electrode surface area may be in the range of about 4 to about 10 mm2. In an alternative example, however, the electrode surface area may be significantly larger, to reduce interface impedance, as the ITV location may make space constraints on the electrodes less of an issue than would be the case in an intracardiac lead position. For example, pacing electrode surface areas may be in the range of above 10 mm2. For example, ring or segmented pacing electrodes may have a surface area, individually or in common (linked together) in the range of about 4 to about 60 mm2. In an example, ring or segmented pacing electrodes may have a surface area (actual) of about 15 to about 30 mm2, and may further include a fractal or other surface features and/or coating to increase effective surface area even more and lower tissue interface impedance. In still other examples, a coil electrode may be used with a surface area in the range of up to about 450 mm2 or more, including up to about 720 mm2. An electrode may be reused for each of pacing, defibrillation, and sensing, if desired.

The resulting output requirements for a pacemaker may therefore be reduced to allow easier electrical design and efficient or lower energy operation. For example, assuming a system designed for up to 1200 ohm impedance, and a maximum 50 mA output, the device would need capability for up to 60 volts output. Increasing surface area to reduce the maximum needed impedance capability to a lower level of, for example, 400 ohms would allow the maximum voltage requirement to be reduced to 20 volts.

Figure 22:
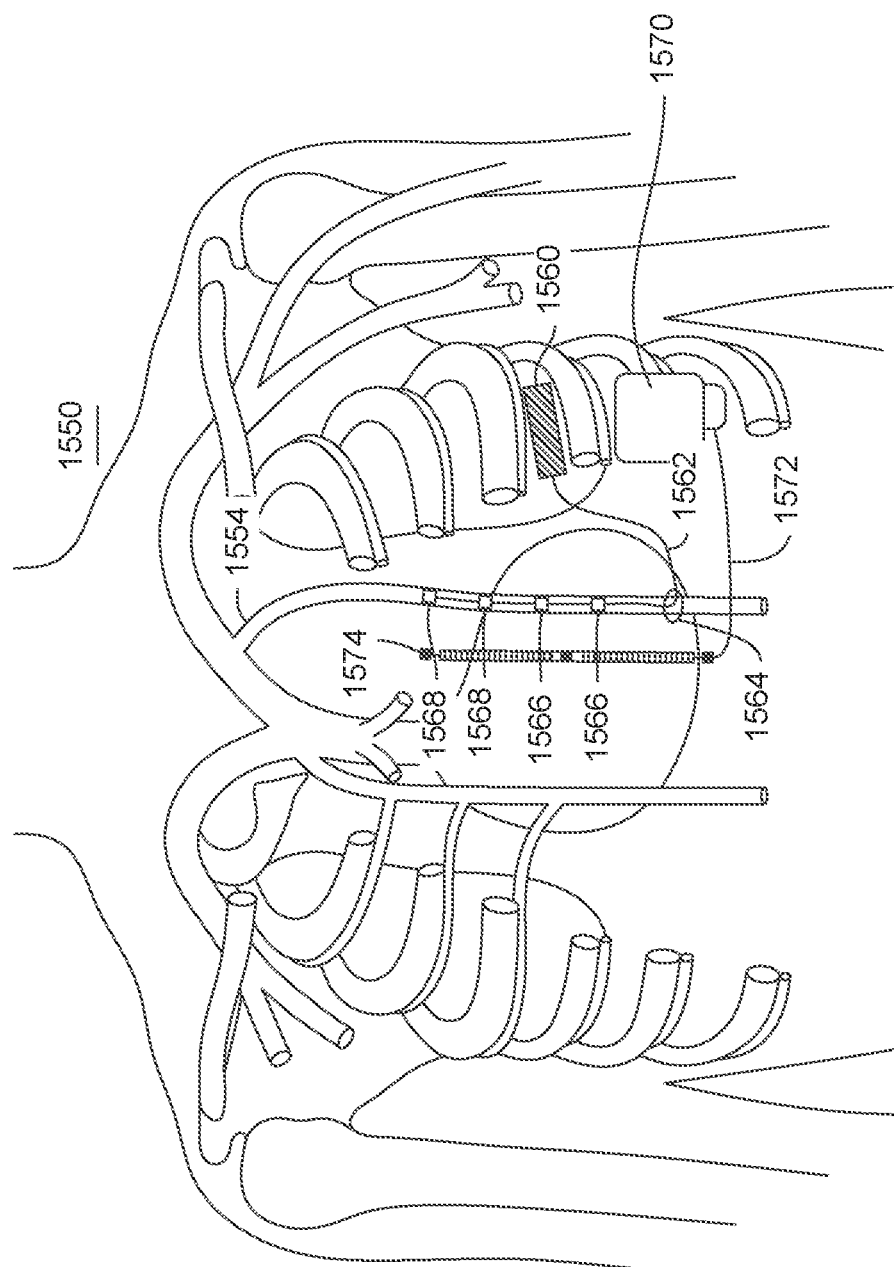
FIG. 22 shows concomitant subcutaneous defibrillator and extracardiac pacemaker with left ITV lead position using an intercostal access.

FIG. 22 shows concomitant subcutaneous defibrillator and extracardiac pacemaker with left ITV lead position using an intercostal access. In this example, the patient 1550 is illustrated having a heart 1552 and left ITV at 1554. An extracardiac pacemaker is implanted in the patient including a housing at 1560 coupled to a lead 1562 that enter the left ITV through an intercostal access at 1564 and includes proximal electrodes that are about level with the ventricles at 1566, and distal electrodes more in line with the atria at 1568. Other numbers and placements for electrodes on the lead 1562 may be used. The housing 1560 is in the fourth intercostal space, while the access location 1564 is in the fifth intercostal space. In other examples, a more superior access location may be used, with two leads going superior and inferior in the ITV included instead of one, or a single lead having a bifurcation such that portions go inferior and superior in the selected ITV.

A subcutaneous defibrillator is also implanted in the patient 1550 in FIG. 22. The subcutaneous defibrillator includes a housing 1570 implanted at about the left axilla, with a lead 1572 extending generally along or inferior to the inframammary crease toward the sternum and/or xiphoid of the patient, and thence superiorly parallel to the sternum and 1-2 cm to the left of the sternum. Coil and sense electrodes 1574 are provided on a distal portion of lead 1572. Generally speaking, the implantation of the subcutaneous defibrillator may be performed as described in U.S. Pat. Nos. 7,655,014 and 7,149,575, the disclosures of which are incorporated herein by reference, and/or as described in the labelling of the S-ICD System™ as approved by the US FDA under PMA P110042.

In some examples, the extracardiac pacemaker 5160/1562 may be generally used instead of a leadless cardiac pacemaker in a concomitant system as described for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference.

In this example, the left sided placement of the housing 1560 may be preferred insofar as the leads 1562, 1572 do not overlie one another, meaning that there is no need to tunnel one lead over or under the other. In another example, an abdominal placement using an inferior access into the ITV via the superior epigastric vein, as shown below in FIG. 11, may be used instead.

The combined system may have several cooperative configurations:

In an example, the subcutaneous defibrillator system is configured to sense and detect cardiac arrhythmias. If a monomorphic ventricular tachycardia is detected, the subcutaneous defibrillator can indicate to the extracardiac pacemaker using RF or inductive telemetry, or using conducted communication, a request or command for anti-tachycardia pacing. The subcutaneous defibrillator may also sense and treat deadly arrhythmias such as ventricular fibrillation with defibrillation shocks, with (or alternatively without) advance warning to the extracardiac pacemaker that a high voltage shock is coming. The extracardiac pacemaker may be configured for backup bradycardia pacing, either always on or solely following defibrillation therapy delivery. The extracardiac pacemaker may additionally be configured to provide CRT and/or rate adaptive permanent pacing, if desired.

In another example, the extracardiac pacemaker may sense for high rate rhythms and may indicate presence of high rate to the subcutaneous device, which may respond by activating analysis for identifying and characterizing arrhythmias, with therapy options similar to the prior example.

In another example, the extracardiac pacemaker may provide CRT therapy, with the subcutaneous defibrillator using its sensing and detection capability to assess whether CRT is providing desirable results, as discussed in U.S. Provisional Patent Application Ser. No. 62/378,866, titled CARDIAC RESYNCHRONIZATION USING FUSION PROMOTION FOR TIMING MANAGEMENT, the disclosure of which is incorporated by reference. In another example, a subcutaneous defibrillator provides timing or other triggers to the extracardiac pacemaker to facilitate the CRT as discussed in U.S. Provisional Patent Application Ser. No. 62/355,121, titled CARDIAC THERAPY SYSTEM USING SUBCUTANEOUSLY SENSED P-WAVES FOR RESYNCHRONIZATION PACING MANAGEMENT. Other cooperative CRT pacing examples that may be used may be found in U.S. Provisional Patent Application Ser. Nos. 62/378,880, and 62/397,635, the disclosures of which are incorporated herein by reference.

In another example, the subcutaneous defibrillator uses a non-rechargeable battery and is configured to provide backup pacing if needed, while the extracardiac pacemaker uses a rechargeable battery and provides chronic pacing (and, optionally, other pacing therapy such as ATP and/or CRT, if desired). The subcutaneous defibrillator can be configured to monitor battery status of the extracardiac pacemaker, using 2-way communication if desired or simply by monitoring the pacing output of the extracardiac pacemaker, which may include markers of battery status using known techniques (modifications to pulse width or rate, for example). When the extracardiac pacemaker indicates its battery is low, it may use ordinary means, such as a buzzer, beeper, or communication to a bedside monitor or other patient communication apparatus (such as low energy Bluetooth communication to a cellphone) to indicate it needs a recharge. If the extracardiac pacemaker battery gets too low, or becomes non-functional due to the patient failing to charge when requested, the subcutaneous defibrillator takes over the pacing responsibility. It is very likely that the patient will find pacing by the subcutaneous defibrillator uncomfortable immediately and will then remember to charge the extracardiac pacemaker.

An alternative may be as in the preceding example, but now the extracardiac pacemaker may omit any buzzer or beeper, and instead relies on the subcutaneous defibrillator to provide such annunciation. Omission of the buzzer or beeper may reduce the size and/or weight of the extracardiac pacemaker.

In another example, any of the above examples may be configured such that the extracardiac pacemaker omits any communication circuitry other than having output circuitry configured for conducted communication to the subcutaneous defibrillator, again to reduce device size.

This list is not intended to be exhaustive, and other cooperative or paired operation may be used.

Figure 23:
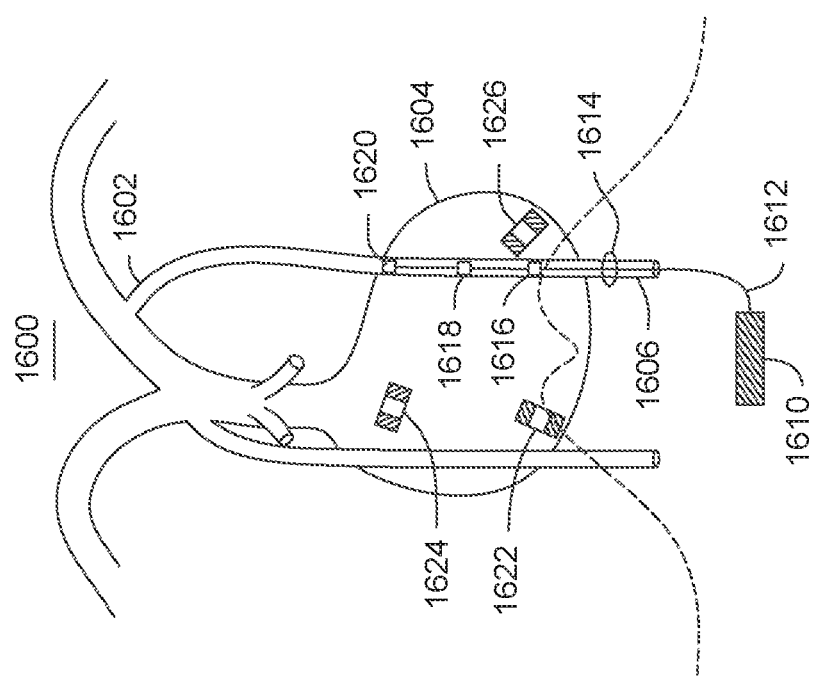
FIG. 23 shows more than one LCP used with an ITV located device.

FIG. 23 shows concomitant leadless cardiac pacemakers and extracardiac pacemaker with a left ITV lead position using inferior access and an abdominally located housing. In this example, the patient 1600 is shown with the left ITV at 1602 and heart at 1604, with the superior epigastric vein at 1606. An extracardiac pacemaker has a housing 1610 that has been placed abdominally, with a lead 1612 entering the superior epigastric vein 1606 at a location 1614 inferior to the lower rib margin. The lead 1612 includes three electrodes 1616, 1618, 1620 in this example, with one electrode 1616 over approximately the apex of the left ventricle, a next electrode 1618 generally still over the left ventricle though more superior than electrode 1616, and one electrode 1620 about level with the left atrium.

The patient 1600 may also have one or more of the leadless cardiac pacemakers (LCPs) that are shown at 1622, 1624, and 1626. Illustrative details of an LCP are discussed below relative to FIG. 28. Three LCP device are shown; in other examples, only one or two LCPs may be provided, or a fourth device may be provided in a chamber or associated with a blood vessel on the heart (such as the coronary sinus as disclosed in US PG Pat. Pub. No. 20160228712). A four chamber solution may allow for various advances; for example, atrial activity can be synchronized between the two atria, a chamber-to-chamber sequence of events may be defined such that stimulus can be provided in a sequential fashion to achieve optimized synchronization, and/or chamber to chamber electrical signaling may be observed, including timing, to develop models for arrhythmia and/or chamber synchronization from which diagnosis and optimized treatment may be developed.

In addition, various combinations and cooperative operations are made available:

The LCP devices may be used to generate specific therapies, such as CRT, using data sensed and/or analyzed by the extracardiac pacemaker. For example, the extracardiac pacemaker may assess whether CRT delivered by the LCP devices is providing desirable results, as discussed in copending U.S. Provisional Patent Application Ser. No. 62/378,866, titled CARDIAC RESYNCHRONIZATION USING FUSION PROMOTION FOR TIMING MANAGEMENT, the disclosure of which is incorporated by reference. In another example, an extracardaic pacemaker provides timing or other triggers to the LCP to facilitate the CRT as discussed in copending U.S. Provisional Patent Application Ser. No. 62/355,121, titled CARDIAC THERAPY SYSTEM USING SUBCUTANEOUSLY SENSED P-WAVES FOR RESYNCHRONIZATION PACING MANAGEMENT, the disclosure of which is incorporated herein by reference. Other cooperative CRT pacing examples may be found in U.S. Provisional Patent Application Ser. Nos. 62/378,880, and 62/397,635, the disclosures of which are incorporated herein by reference.

In another example, the extracardiac pacemaker may be provided to coordinate system operation and/or as a backup for the LCP devices in the event of failure. For example, the LCP devices may be of a size and communication capacity that makes home monitoring difficult without the use of a wand. The extracardiac pacemaker may facilitate communication from an external home monitor to LCP devices by use of conducted communication to the LCP devices and an RF communication (Medradio in the 401-406 MHz band, or Bluetooth, for example) to a home monitoring device.

In still another example, rather than an abdominal housing placement with reduced size, the canister 610 may be replaced with a canister as shown above in FIG. 7, at the left axilla, with full defibrillator function. For this example, the communication between the implanted defibrillator and the LCP devices may be to coordinate subcutaneous defibrillator operation with an LCP, including management of ATP, post-shock pacing, and data capture to determine whether a treatable arrhythmia is taking place.

An extracardiac device as illustrated in FIG. 11 may be used with a coronary sinus device as in US PG Pub. No. 20160228712 as well as one or more LCP devices, with the extracardiac device capturing far field cardiac signals to determine efficacy and/or aid with adjustments/timing/amplitudes used in a resynchronization therapy protocol implemented on the LCP and coronary sinus devices. For example, the extracardiac device may sense a change in impedance or blood pressure to determine whether the LCP pacing output has captured the patient's heart, thus using a non-electrical signal, or the extracardiac device may capture the patient's cardiac electrical signal to determine whether an R-wave matching a "capture" template is issued in response to the LCP output.

Other cooperative combinations may be used instead.

As noted above, an extracardiac pacemaker may facilitate CRT using an LCP by triggering therapy delivery and/or by analyzing therapy results to encourage fusion beats in the CRT regimen. Fusion beats occur when multiple signals arrive at the same chamber at the same time to enhance contraction strength and/or efficiency. In some examples, the extracardiac pacemaker may further assist in observing CRT need by monitoring heart failure status. For example, impedance measurements across a portion of the patient's chest may be used to determine fluid status of the patient; more fluid means poorer heart failure status and vice versa. With worsening heart failure status, the duty cycle for CRT may be increased if, for example, CRT pacing is delivered cyclically. Warnings or alerts related to heart failure status may also be issued.

It may be noted for purposes of these various combinations that ATP can be delivered for selected arrhythmias. For example, ATP typically does not convert (return to normal rhythm) arrhythmias that are polymorphic and highly disorganized, such as polymorphic ventricular tachycardia or ventricular fibrillation. ATP also will have no affect on atrial arrhythmias such as atrial fibrillation or flutter. Thus, ATP generally may be delivered for monomorphic ventricular tachyarrhythmia (MVT). One approach to ATP is to set a rate zone within which ATP may be declared, and to analyze cardiac signals to determine that a patient's heart is displaying a rate in the ATP rate zone with a monomorphic shape by comparing cardiac cycles to one another; when the shape matches from one cycle to the next, the underlying condition may be deemed monomorphic, and given a rate in the ATP zone, after some persistence (such as a user defined set of 8 to 20 beats, or more or less), an MVT can be declared and ATP delivered. The extracardiac pacemaker may be useful to analyze or distinguish MVT from polymorphic arrhythmias, and can communicate commands or data to an LCP or other device to trigger, inhibit, or assist with analysis regarding whether to deliver ATP.

In some examples, an extracardiac pacemaker may be used in conjunction with an LCP to deliver and manage bradycardia pacing. For example, an LCP may deliver a rate adaptive pacing therapy, and the extracardiac pacemaker may assist by monitoring indications of the patient's metabolic demand. For example, the extracardiac pacemaker may include an accelerometer to detect patient activity; as more activity is detected, the extracardiac pacemaker may request the LCP increase its rate or, as the patient returns to rest, the extracardia pacemaker may request the LCP decrease its rate. In an example, the extracardaic pacemaker may be configured to monitor for respiration such as by tracking one or more of depth and rate of respiration to determine whether the patient has an increased metabolic need. Respiration monitoring may rely on chest motion or may instead rely on sensing diaphragm originating muscle signals, for example. In another example, the extracardaic pacemaker may include a sensor to monitor oxygenation on a portion of the lead of the extracardiac pacemaker disposed in the blood stream; low oxygenation suggests demand exceeding supply, and thus the LCP may receive a communication suggesting rate increase; oxygenation above a threshold may cause the extracardiac pacemaker to remove its request for increased rate from the LCP. The LCP may also include a sensor for use in rate adaptive pacing, such as a temperature sensor or accelerometer, if desired; if so, then the extracardiac pacemaker may serve as an adjunct or double check the LCP rate adaptive processes.

Figure 24A:
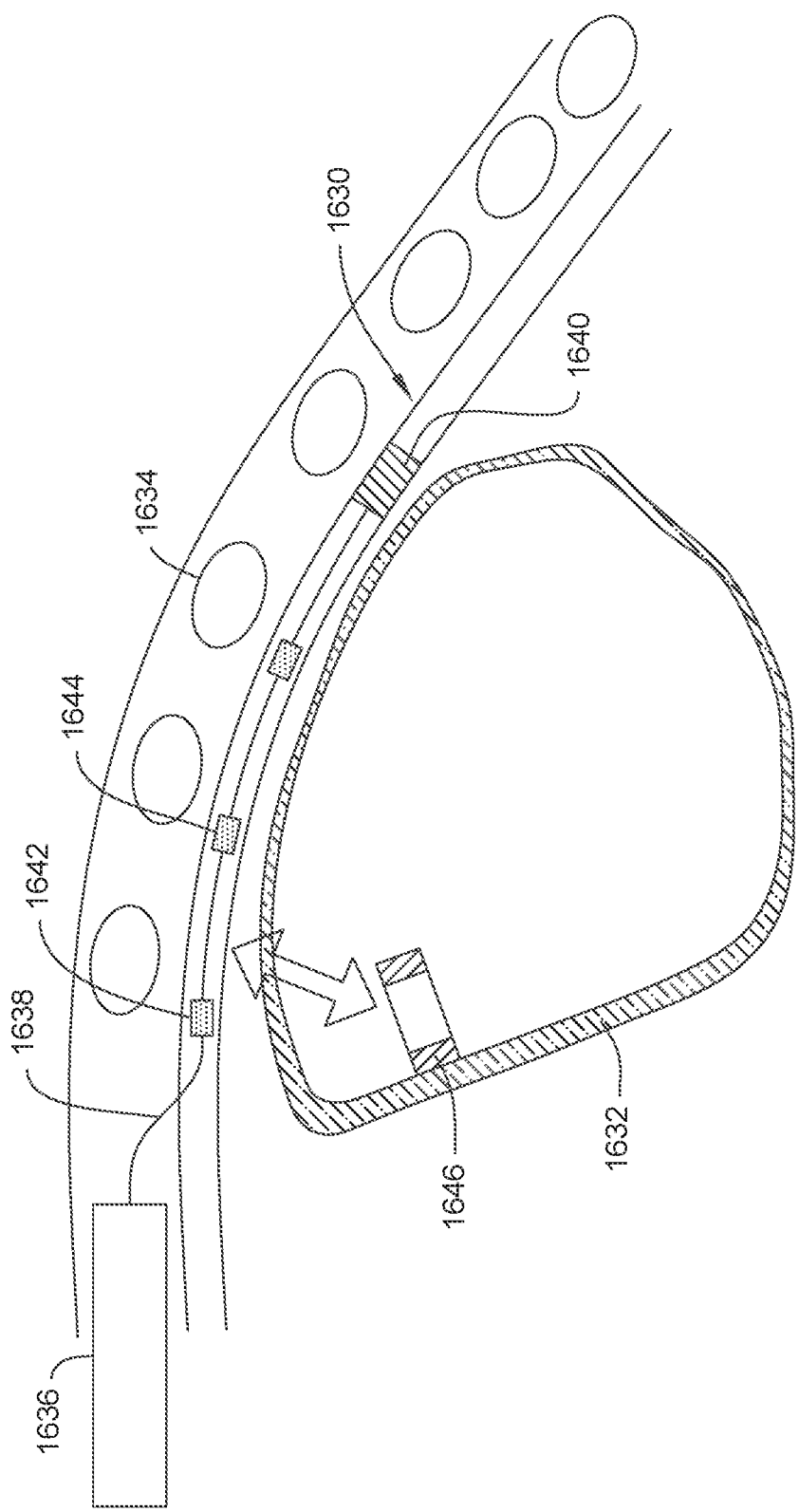
FIGS. 24A-24B are lateral views of devices using the ITV and an LCP.
Figure 24B:
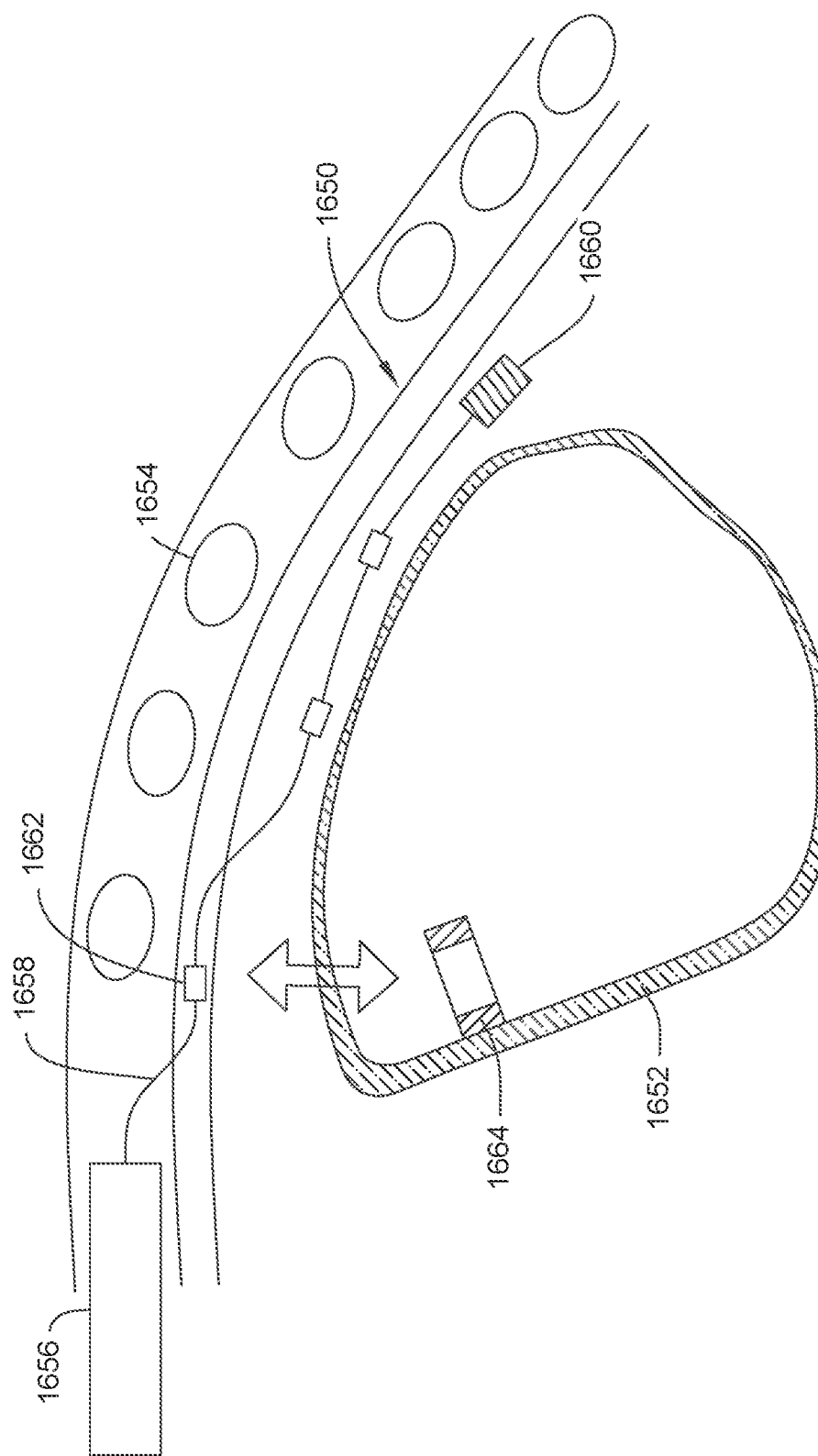

FIGS. 24A-24B are lateral views of devices using the ITV concomitant with an LCP. Referring now to FIG. 24A, in this example, a patient is shown in a lateral view with relevant elements shown in isolation for clarity purposes. The ITV is shown at 1630 (item 1630 may be the left ITV for example), passing generally over the heart 1632 and beneath the ribs 1634. An implantable device 1636 is implanted generally in the abdomen, with a lead 1638 that enters the superior epigastric vein and/or the musculophrenic vein and passes then into the ITV 630. The lead 1638 is shown having a distal fixation device at 1640, shown as an expanded stent type apparatus in this example, with a plurality of electrodes including those at 1642, 1644. An LCP is shown in a ventricle at 1646. The LCP can communicate with the ITV pacing system using, for example conducted communication with a pair of the lead electrodes 1642, 1644, or, if desired, a different combination of electrical contacts such as a conductive element or portion of the housing of the device 1636 paired with one of the electrodes 1642, 1644 and/or the distal fixation tip 1640, which may be conductive if desired.

FIG. 24B shows an alternative placement. In this example, the ITV is shown at 1650 relative to the heart 1652 and ribs 1654. A device housing is shown at 1656 and couples to a lead 1658 which enters the superior epigastric vein and then passes first into the ITV 1650 and then, more superiorly, again exits the ITV into the mediastinal space. Such an exit from the ITV 1650 may be accomplished by advancing a guidewire through a side port, for example, of a catheter and through the vein wall, and then passing a dilator/guide catheter over the guidewire and through the vessel wall, with the lead then being introduced through the guide catheter that has passed through the vessel wall, after removing the guidewire. This allows the distal portion of lead 1658 to reside in the mediastinum and somewhat closer to the heart 1652.

FIG. 25 shows an illustrative insertion tool for a pacemaker in accordance with some examples. The tool is shown generally at 1680 and includes a handle 1682 with a dissecting shaft 1684 having a pointed but blunt tip 1686 for dissecting subcutaneous tissue, preferably to separate tissue planes. The pacemaker 1690 is contained as shown in the handle for purposes of initiating the procedure, with the lead 1692 optionally attached (if detachable) to the pacemaker 1690. For implantation, an incision is made through the skin to access a subcutaneous space, and the tip 1686 and dissecting shaft 1684 are inserted through the incision in a desired direction to create a pocket for receiving the pacemaker 1690. A pusher 1696 is then inserted via loading slot 1694 to push the pacemaker 1690 out alongside the dissecting shaft 1648 and into the subcutaneous pocket. The lead 1692 can be tunneled in a different direction to its desired implant position.

In other methods of implantation the lead 1692 may first be positioned and the housing 1690 placed after manual dissection of a pocket or after dissection using a simple dissection tool such as a blunt dissector.

FIGS. 26A-26D show affixed and removable leads with illustrative pacemaker housings. In the example of FIG. 26A, the system is shown at 1700 with a rectangular housing at 1710 having a conductive electrode 1712. The electrode 1712 may make up most of the housing surface 1710 or may, as shown, be a smaller portion thereof. An electrode 1712 may instead be omitted if desired. The housing 1710 may include a header 1714, if desired, that may optionally be separate from the conductive surface and/or electrode 1712. A lead 1720 is, in this example, permanently attached to the header 1714, with a plurality of electrodes 1722 thereon and a distal tip 1724 shown in this example having tines for attachment to tissue to hold the position of the lead once implanted. Such tines may have any suitable structure and may be restrained during insertion using, for example, a dissolvable coating or a removable jacket or sheath.

In the example of FIG. 26B, a system is shown at 1750 including a housing 1760 having again an electrode 1762 (similar to the example of FIG. 26A), and a header 1764. The header 1764 includes a bore 1766. The lead 1770 includes a proximal end having a plug 1772 for insertion into and attachment at the bore 1766 using, for example, suture, a set screw, or mechanical attachment/snap/spring loading to hold the lead 1770 in place. The plug 1772 and/or bore 1766 may include one or more seals if desired, to control fluid ingress. The lead 1770 is shown again with a plurality of electrodes 1774 and a distal tip 1776 which may also be conductive or serve as an electrode. In this example, the distal tip 1776 is shown having a helical anchoring feature, which may again be restrained during insertion if desired.

FIG. 26C shows another example. Here the system 1800 includes a cylindrical housing 1802. A large portion of the cylindrical housing 1802 is a conductive electrode 1804. Other examples may be different insofar as the size and design of the conductive electrode 1804. The housing 1802 includes a header that attaches to a lead 1810. In this case, the lead 1810 may omit a specific anchoring structure and, instead, includes a predetermined curvature that is sized and dimensioned, in two or three dimensions, to anchor the lead 1810 in the ITV after implantation. For example, a stylet may be used to straighten the lead 1810 for implantation, with the stylet being removable through a side port of the lead 1810 and/or through a portion of header 1806. In another example, the lead 1810 may include a support structure such as a stiffening coil or core wire having a shape memory metal adapted to assume a crooked shape after it warms to body temperature during and after implantation.

FIG. 26D illustrates yet another example. Here, the system 1820 includes a cylindrical housing 1822 including a conductive surface electrode 1824 and having a header 1826. The header 1826 includes a bore for receiving a proximal plug of the lead 1830. Again, the lead 1830 has plural electrodes and is configured to assume a wavy or otherwise 2 or 3 dimensional crooked shape after implantation. A straightening stylet or guidewire may be used to facilitate implantation of the lead 1830, and/or the lead 1830 may rely on a shape memory metal to adopt the wavy or crooked shape.

In an example as shown in FIG. 26A/B, a device volume may be in the range of about 3 to about 12 cubic centimeters with a length in the range of about 40 to about 80 mm, a width in the range of about 10 to about 30 mm, and a thickness in the range of about 5 to about 10 mm. A cylindrical design as shown in FIGS. 26C/D may have a volume in the range of about 3 to about 12 cubic centimeters, with a length in the range of about 40 to about 80 mm, and a diameter in the range of about 8 to about 20 mm.

Other examples may use different dimensions and shapes; some example may use a rounded rectangular format and/or an oval cross section. For example, with added length, width or thickness, the volume may go up to as much as about 20 cubic centimeters. Some examples may go lower in volume to a range of about 2 cubic centimeters. One example may have a length of about 50 mm, width of about 20 mm, and a thickness of about 10 mm, with rounded edges all around, for a total volume of about 9 cubic centimeters. The entire device housing, or a portion or portions thereof, may serve as an electrode or as a plurality of separately addressable electrodes such as shown, for example, in U.S. Pat. No. 5,331,966, and/or U.S. Pat. No. 6,647,292, the disclosures of which are incorporated herein by reference.

The designs shown in FIGS. 26A-26D may be used as shown above in FIG. 20 in the abdominal position 1462, the intercostal position 1470, or the sternal position 1480. In other examples, the designs in FIGS. 26A-26D may instead be used for the subclavicular implant position shown above in FIG. 5, and in any of the canister or housing positions shown below in FIG. 29 at A-E.

Figure 27:
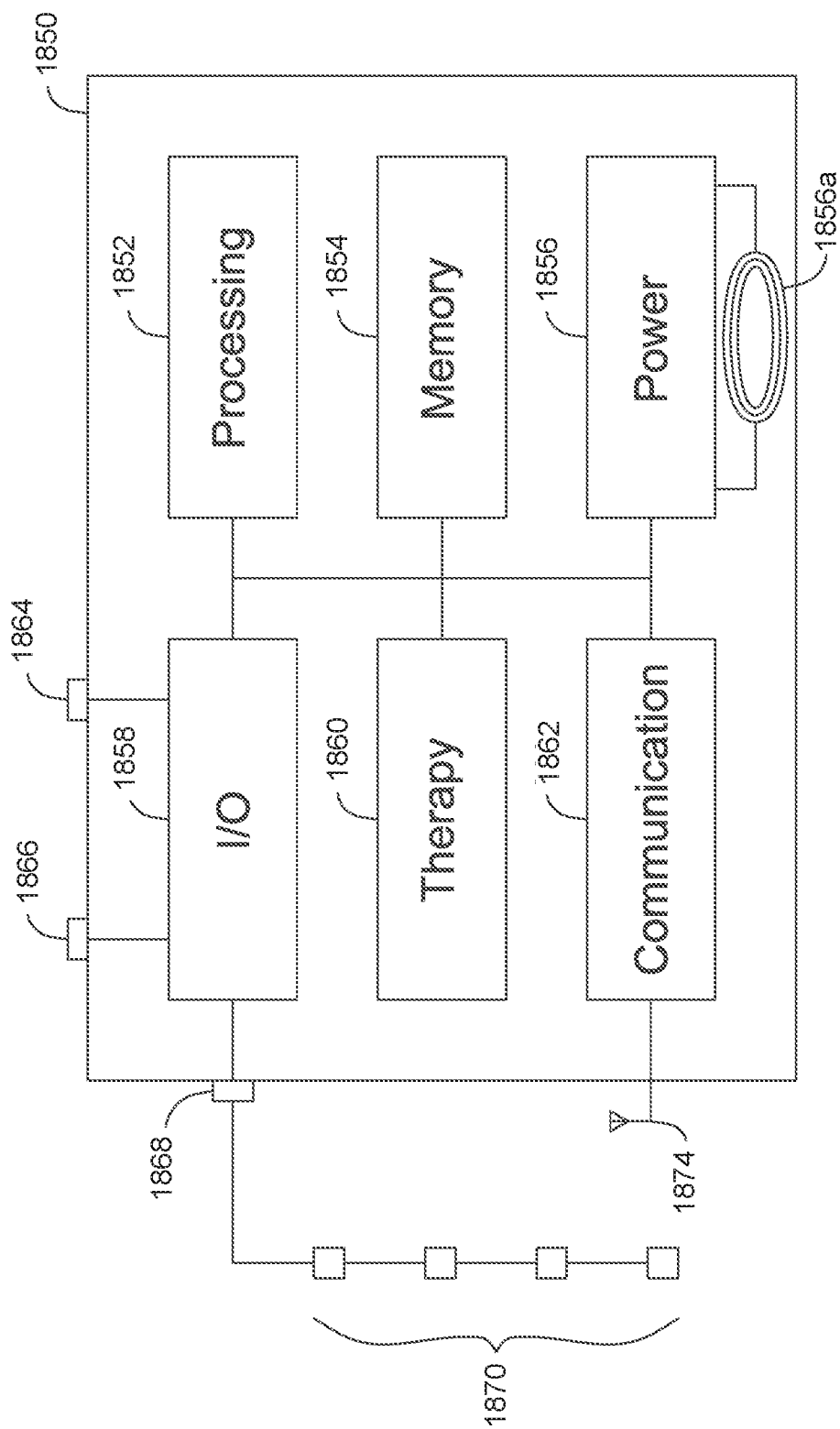
FIG. 27 shows illustrative operational circuitry and design for implantable medical devices in accordance with certain embodiments.

FIG. 27 shows illustrative operational circuitry and design for implantable medical devices in accordance with certain embodiments. The device 1850 may include operational circuitry including a processing block 1852, which may include a state machine, an application specific integrated circuit, a microcontroller and/or a microprocessor, as well as suitable logic and analog-to-digital, or digital-to-analog, conversion circuits, for example. The processing block 1852 is coupled to memory 1854 that can store device parameters, history data, instruction sets for performing therapy, communication, diagnostic and other functions, and any other suitable data and/or instructions. A power block is indicated at 1856 and may include a rechargeable or non-rechargeable battery cell and associated power, voltage generating, and regulating circuits. If a rechargeable device is used, a charger coil 1856a may be included to receive RF or inductive energy for charging. A rechargeable capacitor or supercapacitor may be used if desired; both rechargeable and non-rechargeable power sources may be included in one device.

Input/output circuitry is illustrated at 1858 and may be coupled to the canister electrodes 1864, 1866 and/or to a lead having lead electrodes 1870 via one or more ports 1868. For example, a header may be provided to couple to one or more leads via ports 1868. A header may be, for example, a plastic element that is attached to a canister that houses the remaining circuitry, where a feedthrough is provided to couple one or more electrical contacts within the canister to a bore/port in the header that contains contacts adapted to couple to a proximal end (or plug) of a lead or leads. Multiple bores may be provided. As is known in the art the header may further include space to accommodate a telemetry antenna or a recharging coil used to receive inductively generated energy.

The input/output circuitry 1858 may be used to manage incoming and outgoing signals for sensing, detection, therapy and communication using, if desired, separate channels and subsets of coupled electrodes 1864, 1866, 1870. A circuit is illustrated for therapy purposes at 1860. In some examples, the voltage output by the power block 1856 may not be sufficiently high to allow efficacious therapy, and so the therapy block may include a boost converter, for example, to step up voltages for therapy outputs. In some examples the therapy block includes digital to analog circuitry, current mirrors, and other suitable circuits to manage the output therapy magnitude and determine whether current or voltage controlled outputs will be used. Therapy outputs may be square waves, exponentially decaying outputs, or other shapes, as desired.

In some examples the therapy block 1860 may be adapted for pacing therapy output only, and so may include a charge pump or other architecture to attain suitable voltage/power levels for such use by, for example, allowing storage of up to 20, 50, or 100 volts (or some intermediate level, as needed) to serve as a compliance voltage for a constant current output, or to serve as the voltage source for a voltage output pacing circuit. In other examples the therapy block may be adapted to deliver higher power defibrillation stimulus in the range of 5 to 100 Joules, such as in the range of 10-60 Joules, or other ranges noted above. In the case of defibrillation, high power circuitry such as a transformer and associated high power capacitors configured as a charger/storage circuit, and an output circuit such as an H-bridge having high power switches may also be provided for delivering the higher power therapy. As is known to those skilled in the art, such charging/storage/delivery circuits may draw from one to four batteries (or more if desired) over the course of a few to tens of seconds in order to store energy on a capacitor or capacitor bank for therapy delivery, where, for example, ten seconds of charging at several amperes average current can be used to deliver a waveform of, for example, ten to fifteen milliseconds duration.

A communication block is indicated at 1862 and may include mixers, modulators and/or demodulators, or other circuitry such as a transceiver to generate output communication signals to be issued via electrodes 1864, 1866, 1870 and/or antenna 1874, as well as receiving and converting into useful data incoming communications in conducted communication, RF, inductive telemetry or other form. Optical or sonic signals may be used if desired.

Figure 28:
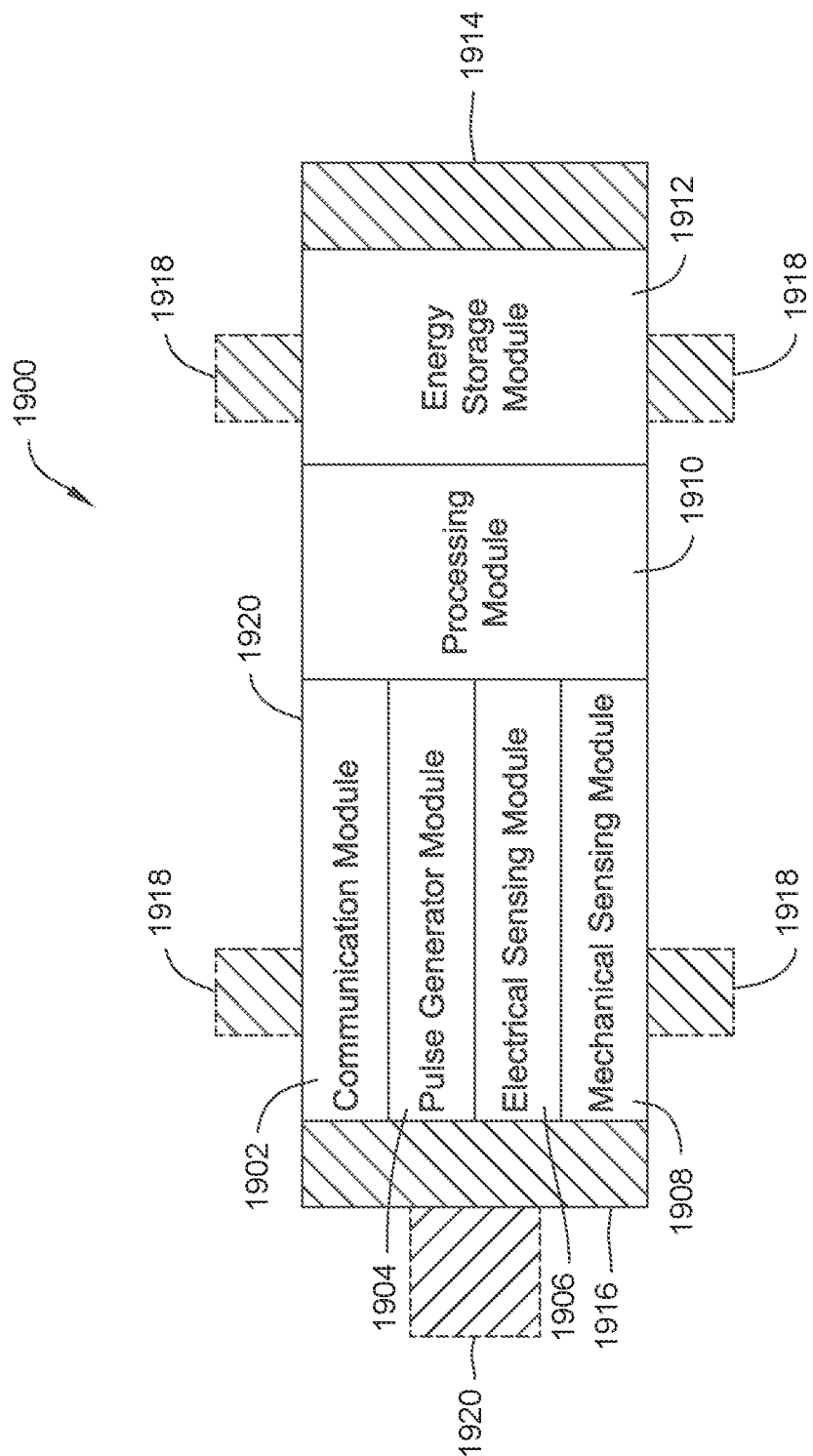
FIG. 28 shows illustrative operational circuitry and design for an example LCP.

FIG. 28 shows illustrative operational circuitry and design for an illustrative leadless cardiac pacemaker. The LCP 1900 is shown as including several functional blocks including a communications module 1902, a pulse generator module 1904, an electrical sensing module 1906, and a mechanical sensing module 1908. A processing module 1910 may receive data from and generate commands for outputs by the other modules 1902, 1904, 1906, 1908. An energy storage module is highlighted at 1912 and may take the form of a rechargeable or non-rechargeable battery, or a supercapacitor, or any other suitable element.

Various details of the internal circuitry for device 1900, which may include a microcontroller, microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 1914 and a second end electrode at 1916. A number of tines 1918 may extend from the device in several directions. The tines 1918 maybe used to secure the device in place within a heart chamber. Another attachment structure is shown at 1920 and may take the form of a helical screw, if desired. In some examples, tines 1918 are used as the only attachment features. Tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Fixation and retrieval structures may instead resemble that of the Micra™ (Medtronic) or Nanostim™ (St. Jude Medical) leadless pacemakers.

Figure 29:
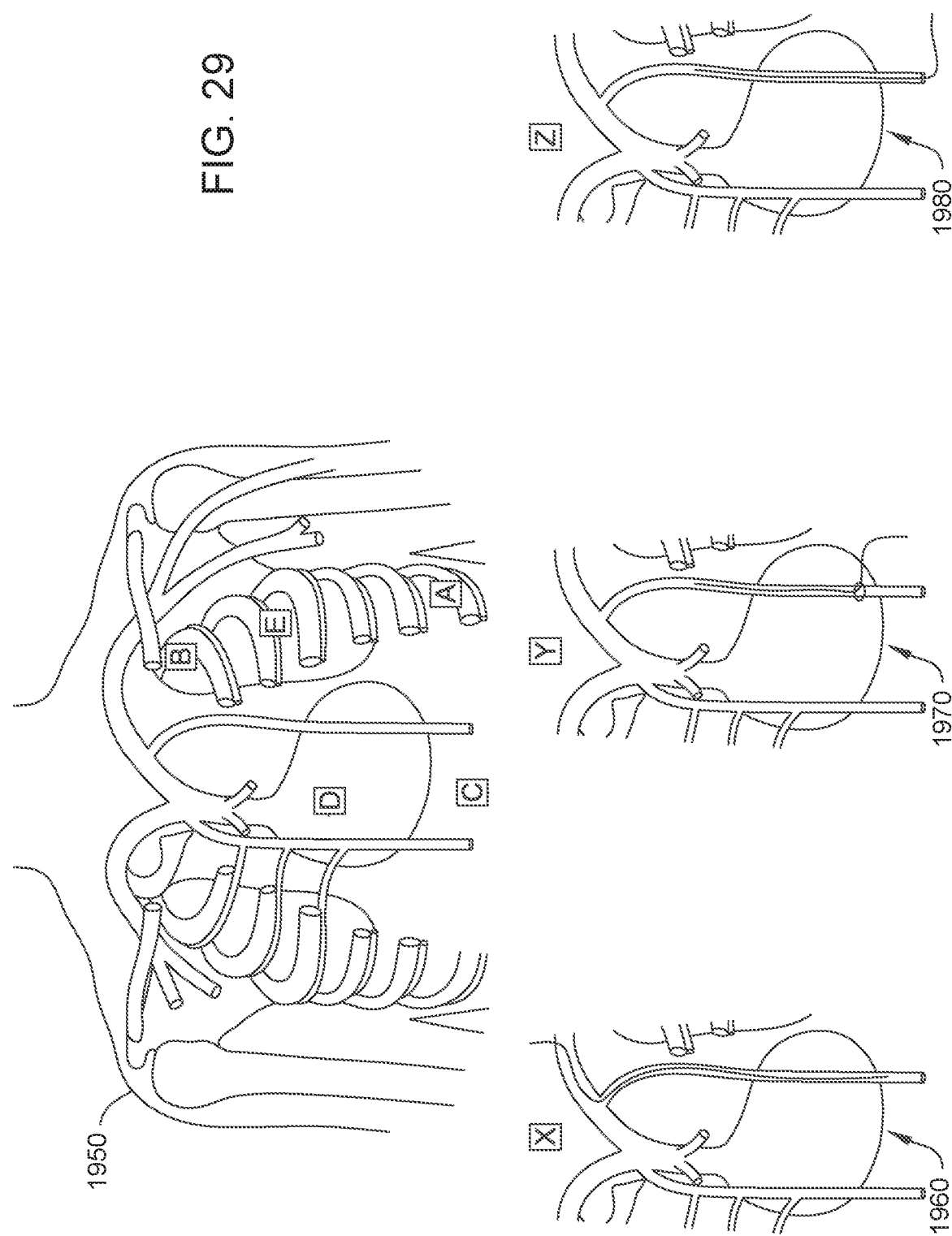
FIG. 29 shows several illustrative implant positions and combinations.

FIG. 29 illustrates a number of implantable positions and combinations. In the upper portion of the figure, a patient torso is shown at 1950. Illustrative positions for an implantable canister are shown at A, the left axilla, B, a left clavicular position, C, an abdominal position, D, a suprasternal position, and E, a costal position. Illustrative placements for a left ITV lead are showing including X, access through the brachiocephalic vessel as shown a 1960, Y, parasternal access through an intercostal location as shown at 1970, and Z, access in the paraxiphoid window as shown at 1980 which may use the superior epigastric vein or the musculophrenic vein.

Right sided positions A', B', and E' (not shown) may be used instead for the various canister locations A, B and E. Right sided positions X', Y', and Z' (not shown), may be used instead for the ITV leads X, Y and Z, and/or there may be leads in both right and left ITVs. A further example relative to position X may include having the access to the brachiocephalic vein cross the midline from right to left or left to right, such that, for example, a subclavicular vein access and entry to the braciocephalic vein from the left side could allow placement of a lead in the right ITV or both right and left ITV. Any of the ITV lead positions may include variants in which the lead then passes into the mediastinum after entry to the ITV, or may include passage from the ITV into an intercostal vein, or passage into the ITV from an intercostal vein.

Thus combinations may be, for example:
  Any one of canisters A, A', B, B', C, D, E, or E' with any one of leads X, X', Y, Y', Z, Z'.
  Any one of canisters A, A', B, B', C, D, E, or E' with any one of leads X, Y, or Z and any one of X', Y', or Z'.
More particularly, the following are thought to be quite practical implementations:
  A or A' with Y, Y', Z, Z', Y and Y', or Z and Z.
  B or B' with X, X', or X and X', including wherein an access for X or X' crosses the patient's midline to provide right ITV lead implant from left side access or left ITV lead implant from right side access.
  C with Y, Y', Z, Z', Y and Y', or Z and Z'.
  D with Y, Y', or Y and Y'.
  E with X, Y, or Z or, alternatively, a modified X crossing the midline to place in the right ITV from a left side access point, standing alone or in combination with either Y or Z.

E' with X', Y', or X', or, alternatively, a modified X crossing the midline to place in the left ITV from a right side access point, standing alone or in combination with either Y' or Z'.

Other positions may be used for the canister, such as, for example, looping the canister around to the posterior ribcage of the patient. It should also be noted that concomitant systems, such as an LCP or SICD may be placed as well, and that additional leads including additional subcutaneous, epicardial, transvenous, mediastinal/substernal, and/or intracardiac leads and electrodes may be included.

In various examples, either or both of the left or right ITV may be used for any of atrial pacing, ATP, and/or bradycardia pacing. For some patients, the right ITV may be more suited to atrial pacing as needed, though this may vary with anatomy and some systems will be capable of atrial pacing from the left ITV. Either ITV may be used as well for sensing atrial and/or ventricular activity. For many patients the right ITV may be preferable for P-wave sensing, though depending on anatomy, signal strength and system capability the left ITV may be used as well. It should be noted that statement regarding right and left ITV usage for various functions may not apply to patient with unusual physiological makeups, such as those patients having a more right sided heart. For example, a patient having hypertophic cardiomyopathy may have the right ventricle more in contact with the left ITV than in other patients, adjusting the capability for chamber specific therapy by making the left ITV less "chamber-specific" to the left side of the heart than might otherwise be the case.

Pacing therapy may be delivered between two electrodes on one lead in a single ITV. Additionally or alternatively, pacing therapy may be delivered between electrodes on a first lead disposed in one of the left or right ITV, and a second lead disposed in the other ITV. Additionally or alternatively, pacing therapy may be delivered between an electrode in an ITV and an electrode disposed on a system housing/canister or on another lead disposed outside of the ITV such as subcutaneously, mediastinally, epicardially, in another blood vessel, or within the heart of a patient.

Chamber specific pacing may be possible as well. For example, in some patients the right ITV may be used to provide pacing therapy to the atria and/or right ventricle and the left ITV may be used to provide pacing therapy to the left ventricle. Again such usage may vary with patient anatomy. Chamber specific pacing may be delivered by using two electrodes in a single ITV and/or by steering therapy output to a particular chamber by selection of an electrode on one lead in an ITV and an electrode on a second lead, in the ITV and/or elsewhere such as on a housing or canister, subcutaneously, mediastinally, epicardially, in another blood vessel, or in the heart, for example.

Figure 30:
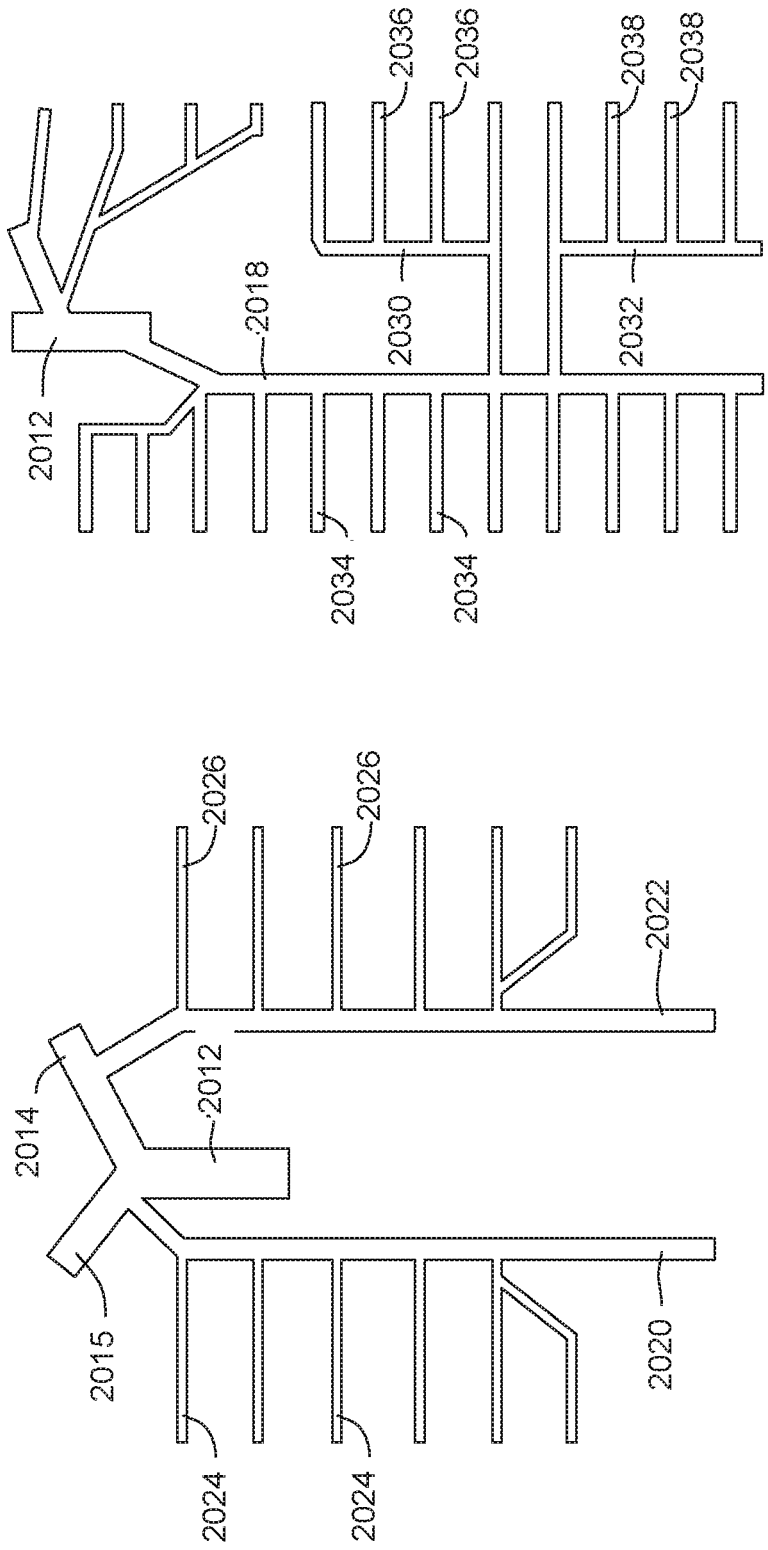
FIG. 30 shows in isolation anterior and posterior thoracic venous structure.

FIG. 30 shows in isolation anterior and posterior thoracic venous structure. The left side of the figure shows the anterior vessels. The left brachiocephalic vein is shown at 2014, and the right brachiocephalic vein is shown at 2015. The right ITV 2020 has an ostium to the right brachiocephalic vein 2015 and travels inferiorly beneath the ribs, with the several right-sided anterior intercostal veins 2024 extending laterally therefrom. The left ITV 2022 has an ostium to the left brachiocephalic vein 2014 and travels inferiorly beneath the ribs, with the several left sided anterior intercostal veins 2026 extending laterally therefrom.

In the posterior mediastinum, the azygos vein 2018 connects to the SVC 2012 and extends to the back, adjacent the right side of the spine, descending therealong. Several tributary vessels branch out laterally from the azygos vein as the right sided posterior intercostal veins 2034. The accessory hemiazygos vein 2030 arches off from the azygos vein 2018 to the left of midline at about T7-T8, and turns to ascend therefrom along the left side of the spine. Several tributary vessels extend laterally from the accessory hemiazygos vein 2030 as the more superior, posterior left sided intercostal veins 2036. The hemiazygos vein 2032 likewise arches off from the azygos vein 2018 to cross the midline and descends therefrom along the left side of the spine. The more inferior posterior left sided intercostal veins 2038 arch off from the hemiazygos vein 2032. The hemiazygos vein 2032 connects as well to the left lumbar vein (not called out in the drawing). The azygos vein 2018 connects inferiorly to the right lumbar vein.

Each of the anterior intercostal veins 2024, 2026 travels on the inferior margin of a rib and extends around the thorax to meet one of the posterior intercostal veins 2034, 2036; separate reference numbers are used for convenience in the figure, but it should be understood that the "anterior" and "posterior" intercostal veins connect. Not all of the branches and veins are shown in FIG. 2. It is conceived that any of the vessels shown may be useful for implantation of a lead or sensor as described below.

Figure 31:
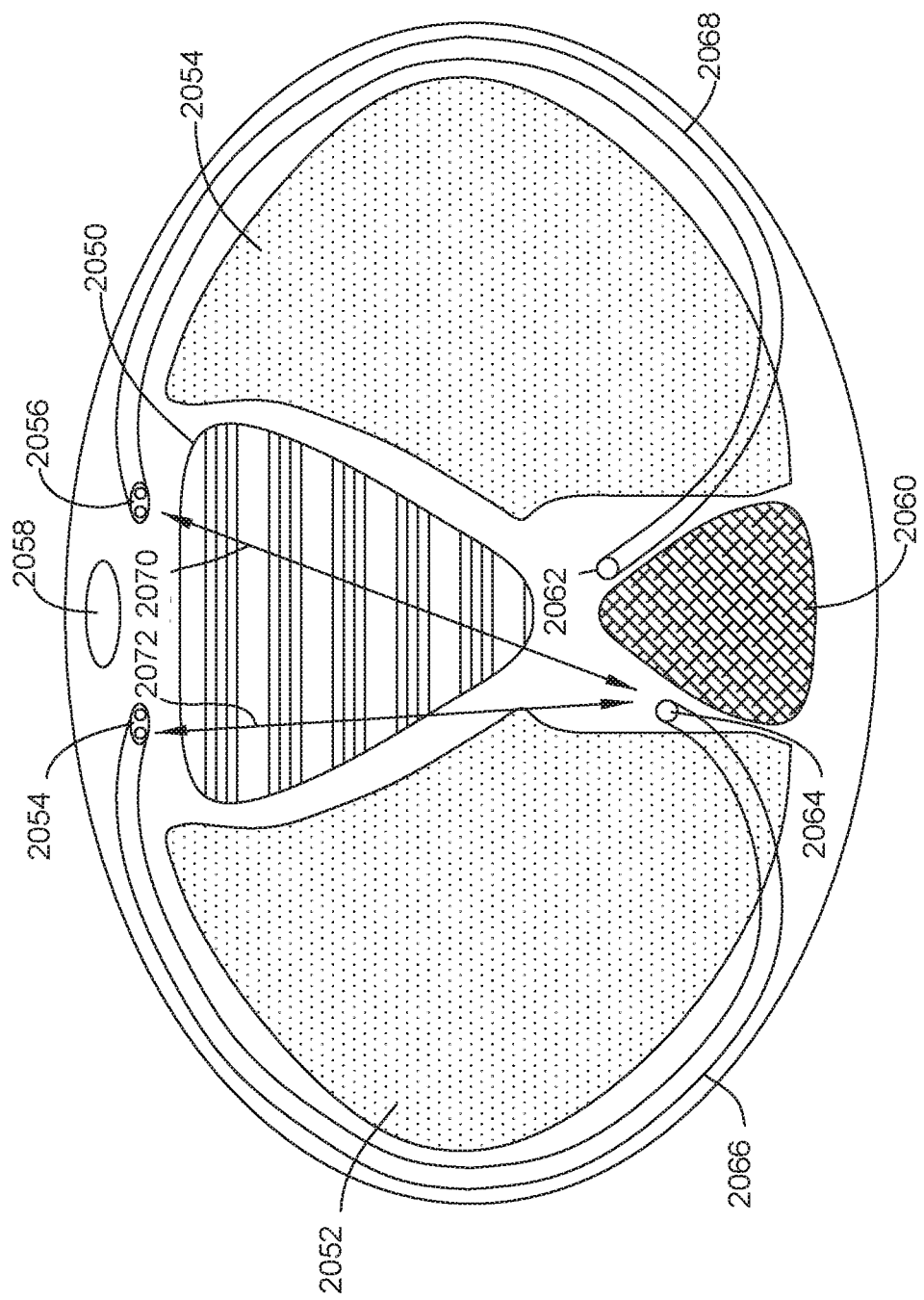
FIG. 31 shows a thorax in sectional view with illustrative therapy electrode locations highlighted.

FIG. 31 shows a thorax in sectional view with illustrative therapy electrode locations highlighted. The heart is shown illustratively at 2050 in a very medial position, with the lungs at 2052, 2054. Therapy vectors which avoid passing through the lungs 2052, 2054 may be preferred as lung tissue—and air in particular, is generally of higher impedance than muscle and fat tissue.

The left ITV is shown at 2054, and the right ITV at 2056, on either side of the sternum 2058. The azygos vein is shown at 2062 and, depending on the superior/inferior position selected, the vein at 2064 may be either the hemiazygos vein (anatomically more inferior) or the accessory hemiazygos vein (anatomically more superior), with these posterior veins on either side of the spinal column 2060. As can be seen, a left side intercostal vein 2066 connects the left ITV 2054 and vein 2064, while a right side intercostal vein 2068 connects the right ITV 2056 to the azygos vein 2062. It should be noted that such connections may not occur on a single transverse plane as shown in FIG. 3; the Figure is intended to be schematic in nature and exact anatomical accuracy is not the aim.

The present inventors have recognized that a vector 2070 from a right ITV 56 to the vein 2064 (whether hemiazygos vein or accessory hemiazygos vein) may be useful to enable pacing or defibrillation therapy focused on the heart. Bone and lung may be avoided using a therapy vector at about the level of T8 to T10. More superior or inferior positions may be used, if desired.

For some patients, the heart 2050 may reside somewhat more on the left side, and thus a vector from the azygos vein 2062 to the left ITV 2054 may be preferred in some examples, rather than that shown. Pre-implant visualization may be useful to plan which of the blood vessel combinations is best suited for a given patient. In still other examples, a shock vector 2072 may be from the vein 2064 (whether hemiazygos vein or accessory hemiazygos vein) to the left ITV 2054, to accommodate a more left sided position may be used instead. Such a vector may be achieved in various ways as set forth below.

Figure 32:
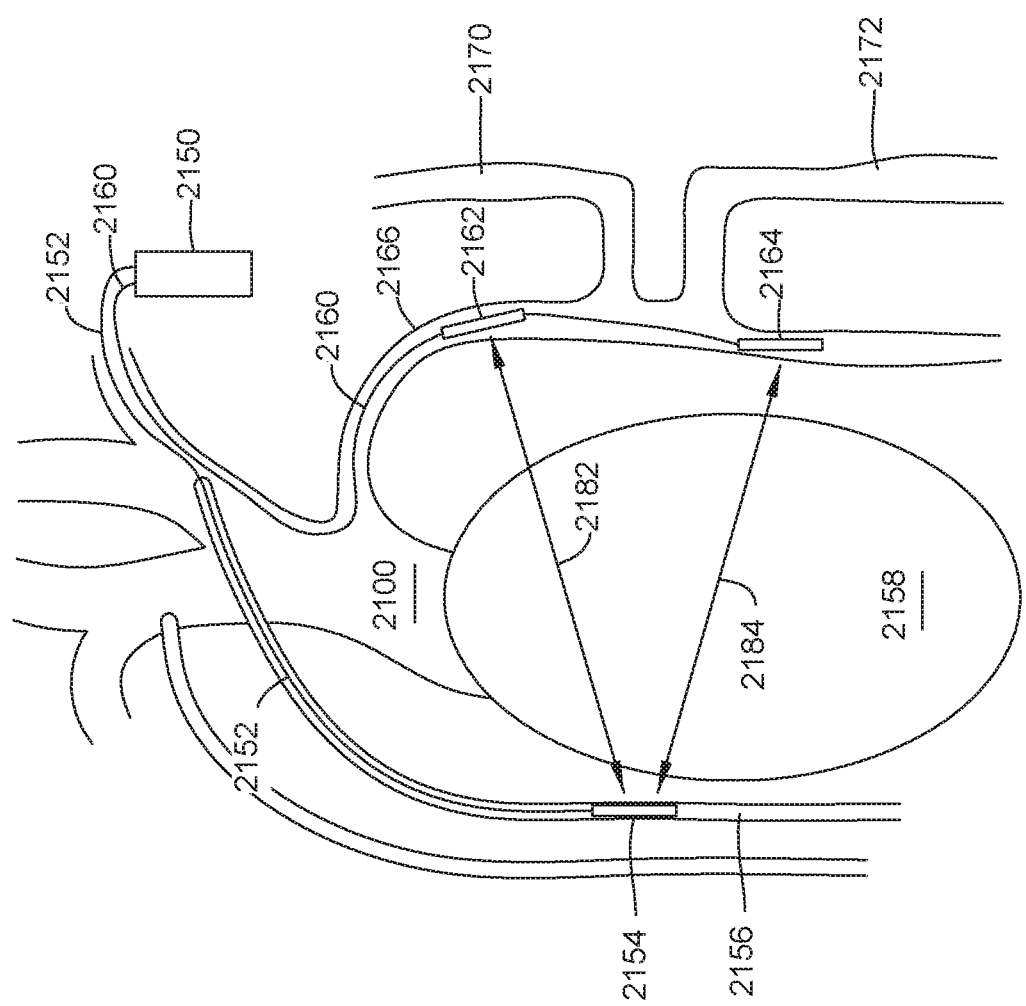
FIGS. 32-33 show illustrative anterior/posterior implant devices.
Figure 33:
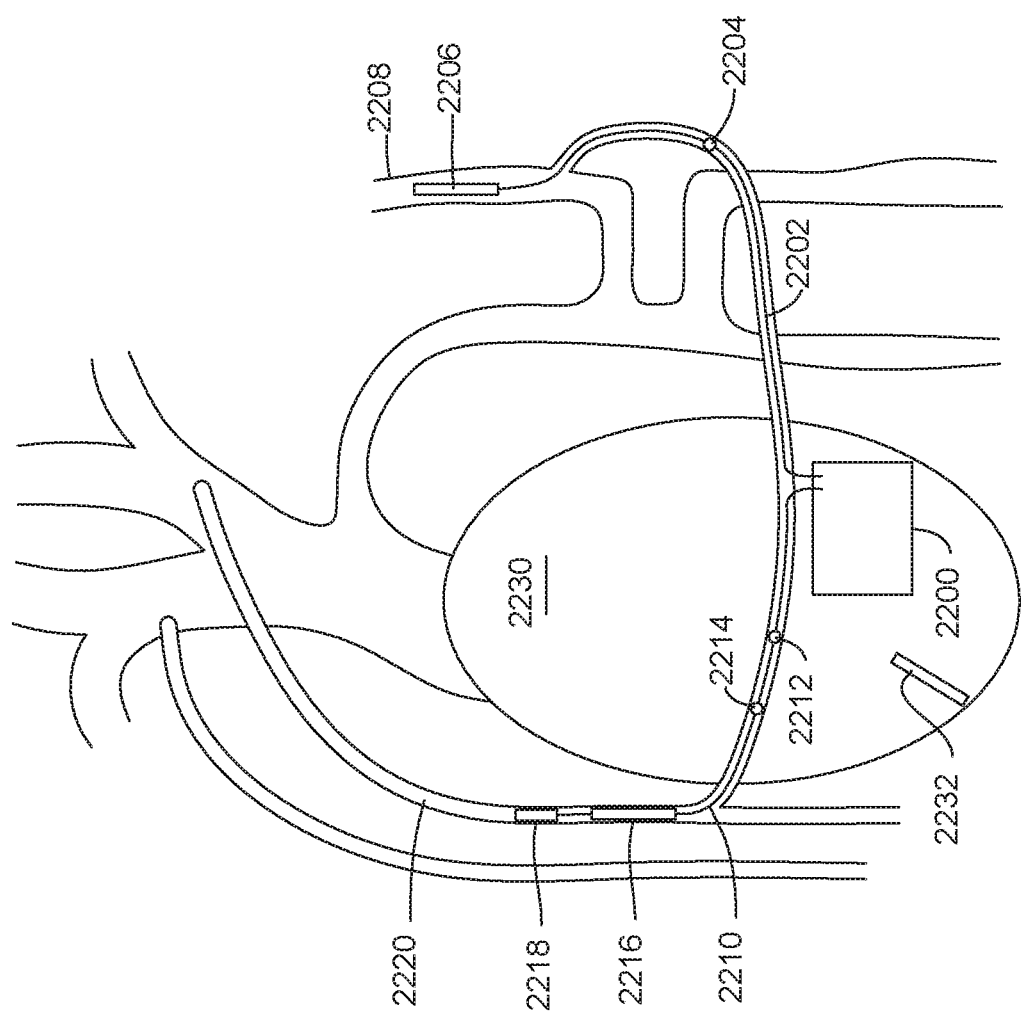

FIGS. 32-33 show illustrative anterior/posterior implant systems. A device canister is shown at 2150 and contains the operational circuitry for a cardiac therapy system. Such operational circuitry is known in the art and may include, for example, output circuitry for high and/or low power therapy (defibrillation, cardioversion, pacing, for example), input circuitry for receiving, filtering, and amplifying received signals (such as the cardiac electrical signal) and converting such signals to digital form for analysis by logic and/or processing circuits to identify cardiac cycles, count such cycles, and determine whether various cardiac rhythms and arrhythmias are present. Sensors and communication circuits may be included as well as power supplies such as batteries of various known chemistries. A device may include a microcontroller or microprocessor with associated logic circuits and readable and/or read-writeable memory containing stored instructions executable to perform sensing and other functions as needed and appropriate and well known in the art. Dedicated circuitry, such as one or more application specific integrated circuits, or other analog or digital circuitry, may be included for filtering, analog-to-digital conversion, cardiac cycle detection, signal shape (morphology) analysis, communication, and other purposes without necessarily invoking the use of a controller or processor continuously. State machines and other architectures may be incorporated as well.

The canister 2150 will typically include a hermetically sealed housing which may double as or include therapy and/or sensing electrode(s) and an associated header and feedthrough structure to couple to leads 2152, 2160. The canister 2150 implant location shown may be that typically used for transvenous implantable systems, near the left clavicle.

Lead 2152 is shown as extending via the brachiocephalic vein into the left ITV 2156, with a therapy delivery or other electrode(s) shown schematically at 2154. A number of sensing, pacing, coil or other electrodes may be included on lead 2152. This position places an electrode 2154 anterior to the heart. A more superior or inferior position relative to the heart 2158 may be used as desired.

Lead 2160 extends through the brachiocephalic vein and into the SVC and then into the azygos vein 2166 and includes at least one therapy electrode. In the example of FIG. 5, the lead 2160 includes a first therapy electrode shown at 2162 and a second therapy electrode shown at 2164. Either or both of electrodes 2162, 2164 may be included as desired. Such an implantation creates therapy vectors shown at 2182, 2184. Therapy may be delivered between electrode 2154 and either or both of electrodes 2162, 2164. Sensing may be accomplished similarly, or may use separate sensing electrodes.

In an example, both of electrodes 2162, 2164 may be used for ventricular defibrillation purposes as a single electrical node with both of 2162, 2164 electrically common as one pole relative to the ITV electrode at 2154. Vector 2184 may be used for lower voltage ventricular pacing, if desired, while vector 2182 may be used for cardioversion to attempt to terminate atrial fibrillation if needed. Alternatively, vector 2184 may serve as a ventricular defibrillation vector without the use of electrode 2162.

For purposes herein, a therapy may be delivered between a first electrode and a second electrode with the first electrode serving as anode and the second electrode as cathode, or vice versa. Moreover, therapy may be monophasic or multiphasic such that the use of anode and cathode during a first phase is reversed in a later phase. Waveforms may be current controlled or voltage controlled. Wave shapes may include square waves or ascending or descending amplitudes (ramped or decaying, for example), sinusoidal forms, or any desired shape.

In the example shown the accessory hemiazygos vein 2170 is not traversed or used; likewise the hemiazygos vein 2172 is not used. In other examples, lead 2160 may be advanced into one of veins 2170, 2172, or both veins may be used if lead 2160 is bifurcated or if two azygos/hemiazygos leads are used.

The lead placements shown may be achieved by the use of a guidewire advanced to a desired position, with the leads placed over the guidewire. In other examples, a steerable lead may be used, or a lead may be placed by advancement using a steerable stylet. Fluoroscopy or other visualization may be used as desired or needed.

In some examples, devices and leads may be specially adapted for placement and/or use in a particular location. For example, the devices may comprise anchors adapted to interact with a venous wall, or sized for a particular location in a patient's vasculature. In an example, a stent, coil or other expandable member may be sized to securely interact with the walls of a blood vessel or valve within a blood vessel by the use of a size that approximates or is slightly smaller or larger than a target vessel. For example, an ITV located device may have an outer diameter of 3 to 10 French, with smaller diameters for placement more inferior in the blood vessel. In another example, a device for placement in an intercostal vein may be sized in the range of about 2 to about 6 French, for example. The azygos vein is typically larger, with diameter in the range of up to 1 cm, and so a portion of a lead that is to be implanted using the azygos vein may include a part thereof adapted for placement in a lesser diameter vein, such as an intercostal, for anchoring purposes. A stent-type placement, including that shown in FIGS. 20C and 21C, for example, may be used, though the other placements shown may also serve in the azygos vein. Larger or smaller sizes may be used as desired.

FIG. 33 shows another example. Here, a left axillary canister position is used to place the canister 2200 at a position similar to that used for the Emblem S-ICD System™ from Boston Scientific. From the left axilla, an intercostal vein 2202 can be accessed and used for advancement of a lead 2204 posteriorly to the accessory hemiazygos vein 2208, placing a therapy or other electrode as shown at 2206. In other examples the more inferior hemiazygos vein may be used instead. A second lead 2210 is advanced in an anterior and medial direction to the left ITV 2220, to place a therapy electrode as shown at 2216. Additional sensing or pacing electrodes may be included on lead 2210 as shown at 2212, 2214, and 2218; rather than electrodes, other sensors (such as accelerometers or heart sound sensors) may be placed. This implantation places the heart 2230 squarely between the therapy delivery electrodes 2206, 2216.

Therapy for defibrillation, cardioversion, and/or pacing purposes may be delivered between anterior electrode 2216 and posterior electrode 2206. The canister 2200 may be used as an additional electrode in electrical common with either of 2206 or 2216, and/or may serve as an indifferent electrode, or may be omitted from therapy delivery as desired. If desired, one or more additional devices such as a leadless cardiac pacemaker (LCP) 2232 may be placed in or on the heart 2230 to provide additional pacing options or other functional inputs such as serving to provide cardiac rate information.

In other examples, lead 2202 may be advanced across the midline to the azygos vein after entering the hemiazygos vein or accessory hemiazygos vein, as desired.

Referring to both of FIGS. 32 and 33, a number of pacing, defibrillation, and/or sensing vectors may be defined. For example, pacing vectors may include:
  Between the right or left internal thoracic vein and the azygos vein;

Between the right or left internal thoracic vein and the hemiazygos vein;

Between the right or left internal thoracic vein and the accessory hemiazygos vein;

Between two electrodes within the same vein, such as between two electrodes in the right or left ITV or in one of the azygos, hemiazygos, or accessory hemiazygos veins;

Between an electrode on a pulse generator canister and an electrode or plural electrodes in one or more of the azygos, hemiazygos, or accessory hemiazygos veins or the right or left ITV;

Any of these combinations may be further adjusted by using an intercostal vein, if desired, to direct current/field in a more lateral direction.

Within such vectors, a selection of superior or inferior positioning within the selected veins may be adjusted to obtain a pacing vector preferentially intersecting a selected atrial or ventricular chamber. For example, pacing between the right internal thoracic vein and the azygos vein at a relatively superior position, level with the atria, may target the right atrium. Pacing therapy delivered between the left internal thoracic vein and the hemiazygos vein may direct the therapy generally to the left ventricle. It may be noted that the left internal thoracic vein may overlie the interventricular septum, allowing pacing of both chambers at once. In some examples, a sensing vector using an electrode in the right or left internal thoracic vein may be used to detect P-waves to support cardiac resynchronization using, for example, a pacing output electrode directed to a ventricular location such as a pacing therapy delivered using an intracardiac pacemaker or a pacemaker electrode in an internal thoracic vein, an azygos, hemiazygos, or accessory hemiazygos vein, or an intercostal vein. Subcutaneous, transvenous, and/or epicardial electrodes may be used in further combinations.

Defibrillation therapy may likewise be delivered using several such combinations:

Between the right or left internal thoracic vein and the azygos vein;

Between the right or left internal thoracic vein and the hemiazygos vein;

Between the right or left internal thoracic vein and the accessory hemiazygos vein;

Any of these combinations may be further adjusted by using an intercostal vein, if desired, to direct current/field in a more lateral direction.

For defibrillation, one consideration may be whether a sufficient mass of cardiac tissue is stimulated in a given configuration. The shock vector may in some examples be different from that of pacing by, for example, delivering diagonally across the torso between the left internal thoracic vein and the azygos vein for defibrillation with pacing delivered between the right internal thoracic vein and the azygos vein. Therapy may be delivered using a combination of three or more electrodes such as:

With defibrillation coil electrodes in each of the right and left internal thoracic veins and the azygos vein, the hemiazygos vein, or the accessory hemiazygos vein, where the coils in the internal thoracic veins are held electrically in common;

With defibrillation coil electrodes in the azygos vein and one (or both) of the hemiazygos vein and/or accessory hemiazygos vein in common, as an opposing pole to a defibrillation electrode in either the right or left internal thoracic vein; and In a four electrode system, a first pole may use defibrillation electrodes in each of the right and left internal thoracic veins electrically in common, electrically opposed to defibrillation electrodes in each of the azygos vein and one of the hemiazygos or accessory hemiazygos veins.

Where more than two electrodes are used, voltage and/or current control may be used to allocate energy to specific electrodes or to target specific tissue using the concept of current steering.

For example, in FIG. 32, a defibrillation therapy output may be manipulated to deliver a greater quantity of current through electrode 2164 than through electrode 2162 to steer current toward the ventricles. Such steering may use current control (such as a current mirror design), or may use voltage control by coupling a lower peak voltage to electrode 2162 than to electrode 2164, by duty cycling (flipping on and off) one of the therapy vectors to a lower duty cycle than the other, or by terminating therapy delivery through electrode 2162 prior to terminating therapy delivery through electrode 2164.

A similar concept maybe used in FIG. 33 to manage output power through electrodes 2216 and 2218. It should be noted that the heart in each of FIGS. 32 and 33 is shown in a more inferior position than may be used in some examples; for example, the canister 2200 and one or more of the therapy delivery electrodes may be positioned more inferior relative to the apex of the heart. The device canister 2200 may optionally be used as an additional electrode for therapy delivery purposes. In some examples, the concept of steering may be accomplished by determining which of several electrodes to include in therapy delivery, rather than by controlling the voltage or current.

Sensing may be achieved between electrode pairs, for example, similar to the pacing combinations noted above. Sensing may also be performed within any one of the vessels noted as by, for example, having first and second sensing electrodes in one of the internal thoracic veins. Superior and inferior positioning may be used to achieve chamber specific sensing vectors (ventricular or atrial, for example).

In an alternative example, a subcutaneous electrode may take the place of a therapy delivery electrode in the internal thoracic vein. For example, therapy may be delivered between a first electrode disposed in least one of the azygos, hemiazygos, or accessory hemiazygos veins, and a second electrode disposed subcutaneously on the anterior chest of the patient such as in a parasternal position. Pacing and/or sensing electrodes may also be disposed, in this example, in an internal thoracic vein.

In a still further alternative, a subcutaneous electrode may take the place of a therapy delivery electrode in the azygos, hemiazygos, or accessory hemiazygos veins. For example therapy may be delivered between a first electrode disposed in one of the internal thoracic veins and a second electrode disposed subcutaneously on the posterior thorax of the patient over the ribcage.

Figure 34:
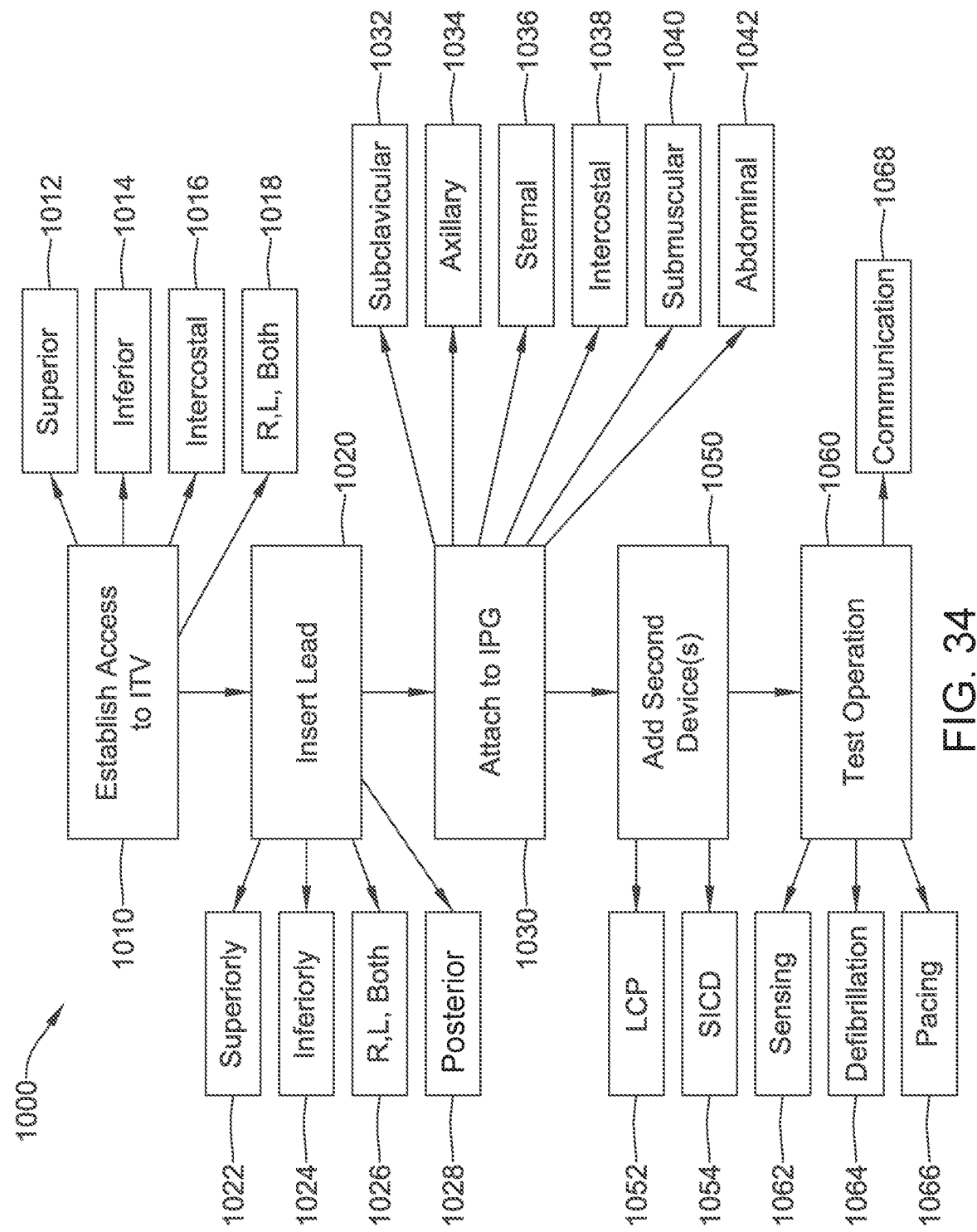
FIG. 34 shows an illustrative implant method in accordance with some examples in a block flow diagram.

FIG. 34 shows an illustrative implant method in accordance with some examples in a block flow diagram. As shown at 1000, the method comprises establishing access to the ITV 1010, inserting a lead in the ITV 1020, attaching an IPG to the lead 1030, (optionally) adding a second device 1050, and performing test operations 1060. For example, establishing access to the ITV 1010 may include accessing from a superior position 1012 such as by entering the subclavian vein and passing through the ostium of the ITV in the brachiocephalic vein. In another example, establishing access to the ITV 1010 may include accessing from an inferior position 1014 such as by entering the superior epigastric vein and passing superiorly therefrom into the ITV. In some examples, access via locations 1012, and 1014 may include accessing via a second blood vessel such as by accessing superiorly 1012 by way of the subclavicular vein and brachiocephalic vein, or accessing inferiorly 1014 through the superior epigastric vein. In still another example, establishing access to the ITV may include accessing in an intercostal space 1016 such as by penetrating an intercostal space and entering the ITV using a Seldinger technique. Some examples using an intercostal space may access a costal vein and passing then into the ITV. The access 1010 may be on the right, left, or both sides of the midline of the patient, as indicated at 1018.

In an example, inserting a lead 1020 may include insertion superiorly 1022, such as by starting in an inferior position 1012 inferior to the lower rib margin or intercostally 1016 from an inferior intercostal location, and advancing the lead in a superior direction. For another example, inserting a lead 1020 may include insertion inferiorly 1024, that is starting at a superior location 1014 or at a superior intercostal location 1016, and advancing the lead in an inferior direction. In either such example, the right ITV, left ITV, or both ITV vessels may be used, as indicated at 1026. In some examples, the insertion of a lead 1020 may further comprise exiting the ITV to enter the mediastinum space, if desired. In some examples, the insertion of a lead may include advancing the lead to a posterior position 1028 as by, for example, wrapping around the patient's torso through an intercostal vein, or by passing down from the brachiocephalic vein into the SVC and then posteriorly to the azygos vein from the SVC, where the lead may be further advanced into a position in the azygos vein, an intercostal vein, the hemiazygos vein, or the accessory hemiazygos vein.

In an example, attaching to an IPG may include attaching to a canister located in a subclavicular location 1032, historically a common place to put an implanted canister for a transvenous defibrillator or pacemaker. In another example, attaching to an IPG may include attaching to a canister located in an axillary position 1034, such as that used with the S-ICD System. Other IPG locations may be used. Attachment may be directly to the IPG or to a splitter, yoke, or lead extension, if desired.

In another example, the IPG may be placed at a sternal location 1036 generally over the sternum. In another example, the IPG may be placed along an intercostal space 1038. In still another example, the IPG may be placed at a submuscular position 1040, such as in a sub-pectoral position and/or at a position between breast tissue and the ribs. In some examples, the IPG may be placed abdominally 1042, inferior to the lower rib margin.

In an example, test operation 1060 may be used to verify one or both of device functionality and efficacy. For example, sensing operations 1062 may be tested and configured to check for adequate signal availability, for example, or by setting gain, filtering, or sensing vector selection parameters. Defibrillation operations 1064 may be tested by inducting an arrhythmia such as a ventricular fibrillation to determine whether the device and a concomitantly implanted defibrillator, such as a subcutaneous defibrillator system, will sense the arrhythmia and, if the arrhythmia is sensed, to ensure efficacious therapy. Defibrillation testing 1064 may include determining for a given patient an appropriate defibrillation threshold, and setting a parameter for therapy delivery by the subcutaneous defibrillator system at some safety margin above the defibrillation threshold.

In an example, pacing testing operation 1066 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided. Pacing testing operation 1066 may include testing of a concomitantly implanted LCP. Pacing testing operation 1066 may also include inter-device testing, to ensure that the presence of two implanted systems (a device using the ITV and configured as a pacemaker plus a subcutaneous defibrillator or an LCP, for example) will not create deleterious interference or interaction therebetween. Pacing testing operation 1066 may also include configuration of integrated, multiple device CRT therapy, if desired, such as suggested in, for example, U.S. Provisional Patent Applications Ser. Nos. 62/355,121, 62/378,880, and 62/397,635, the disclosures of which are incorporated herein by reference.

Communication testing operations 1068 may include selecting vector and timing information for inter-device communication for concomitant systems. For example, communication testing may include elements described in published international patent applications WO 2016/149262 A1 and WO 2016/148928 A1, the disclosures of which are incorporated herein by reference.

FIG. 35 shows another implant position. In this example, a patient 2300 has implanted a pulse generator 2310, which is attached to a lead 2320 having electrodes 2322. For this implant position, the pulse generator 2310 is placed in the left axilla and may be in the anterior position shown, or may instead have a position more lateral or even posterior than that shown. The lead 2320 is tunneled from the pulse generator 2310 to the lower rib margin 2304. At a suitable position 2306, such as up to 10 cm left lateral of the xiphoid, an access is made to the musculophrenic vein 2302. The lead 2320, including the electrodes 2322, is passed through the musculophrenic vein 2302 up to the ITV to a desired position relative to a suitable anatomic landmark, such as to a desired position relative to the heart in general, the cardiac apex, the ventricles, or the atria, for example. At a summary level, FIG. 35 shows an implant location with the pulse generator 2310 at the left axilla and the lead 2310 passing to the lower rib margin and then entering the musculophrenic vein 2302, from which the ITV is accessed for final positioning of at least a portion of the lead 2320, which may include electrodes 2322.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. In at least some embodiments, portions or all of the accessory devices and their related components may be doped with, made of, or otherwise include a radiopaque material. Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

Animal testing has been performed in the porcine model to illustrate feasibility. Such testing made use of selected leads including a prototype lead resembling that shown above in FIG. 10 having a coil electrode 612 with a length of about 4 centimeters, replacing tip electrode 614 with an atraumatic tip, and including two proximal ring electrodes 606, 608 for defibrillation testing between a canister emulator and the 4 cm coil showing at least a thirty-percent reduction in defibrillation threshold relative to a subcutaneous-only defibrillation test in the same animal, using the right ITV to left-sided canister. The prototype lead included a three-dimensional curvature for fixation purposes resembling a spiral.

Additional testing in the same animal made use of an Acuity™ X4 lead (Boston Scientific) for pacing purposes in a unipolar configuration, with the pacing also successful. Still further testing using a now obsolete Perimeter™ CS lead (Boston Scientific), with defibrillation testing also showing a significant reduction in threshold therapy energy. It is estimated that a reduction in defibrillation threshold was in the range of 30-50% for this animal relative to the subcutaneous defibrillation threshold.

A series of non-limiting examples follows. These examples are provided as illustrations of particular embodiments and should not be understand to limit the invention.

A first non-limiting example takes the form of an implantable cardiac therapy system comprising: a first lead configured for placement in an internal thoracic vein (ITV) of a patient, the first lead comprising at least a first electrode thereon for therapy delivery; and an implantable canister for coupling to the first lead, the implantable canister housing operational circuitry configured to deliver output therapy in the form of at least one of bradycardia pacing, anti-tachycardia pacing, cardiac resynchronization therapy, or defibrillation, using at least the first electrode with the first lead in the ITV.

Additionally or alternatively to the first non-limiting example, the operational circuitry may comprise ITV defibrillation means for delivering defibrillation therapy using the first electrode in the ITV having an adjustable output energy in the range of about 10 to about 60 joules. Such ITV defibrillation means may include a circuit block as shown at 1860 and further as described above.

Additionally or alternatively to the first non-limiting example, the operational circuitry may comprise ITV pacing means for delivering pacing therapy by using the first electrode in the ITV by having a pace current output in the range of about 10 to about 50 milliamps. Such ITV pacing means may include a circuit block as shown at 1860 and described above.

Additionally or alternatively to the first non-limiting example, the operational circuitry may comprise ITV pacing means for delivering pacing therapy by using the first electrode in the ITV by having an output voltage in the range of about 10 to about 30 volts. Such ITV pacing means may include a circuit block as shown at 1860 and described above.

Additionally or alternatively to the first non-limiting example, the first electrode on the first lead may be configured to deliver pacing therapy from the ITV by having a surface area in the range of about 15 square millimeters to about 30 square millimeters.

Additionally or alternatively to the first non-limiting example, the first lead may be configured for placement with a first portion in the ITV and with a second portion in an intercostal vein of the patient by having an outer diameter in the range of about 2 to about 6 French.

As a second non-limiting example, and additionally or alternatively to the first non-limiting example, the system may further comprise a second lead having a second electrode for therapy delivery purposes, the second lead adapted to place the second electrode in a selected one of the azygos, hemiazygos, or accessory hemiazygos veins; wherein the operational circuitry is configured to deliver therapy when the first electrode is disposed in the ITV and the second electrode is disposed in the selected one of the azygos, hemiazygos, or accessory hemiazygos veins.

Additionally or alternatively to the second non-limiting example, the implantable canister and first and second leads may be adapted to facilitate placement of the canister in a location near the clavicle such that the first and second leads enter and pass through at least a portion of a brachiocephalic vein.

Additionally or alternatively to the second non-limiting example, the implantable canister and first and second leads may be adapted to facilitate placement of the canister in the left axilla such that the first and second leads enter and pass through one or more intercostal veins.

Additionally or alternatively to the second non-limiting example, the first lead may comprise a third therapy delivery electrode, and the operational circuitry may be configured to shape therapy delivery to target a desired portion of the heart using the first, second and third electrodes.

Additionally or alternatively to the second non-limiting example, the second lead may comprise a third therapy delivery electrode, and the operational circuitry may further be configured to shape therapy delivery to target a desired portion of the heart using the first, second and third electrodes.

A third non-limiting example takes the form of an implantable cardiac therapy system comprising: a first lead configured for placement in an internal thoracic vein (ITV) of a patient, the first lead comprising at least one electrode thereon for sensing a cardiac electrical signal; and an implantable canister for coupling to the first lead, the implantable canister housing operational circuitry configured to sense cardiac electrical activity for analyzing a status of the heart of a patient using the electrode on the first lead, the operational circuitry adapted for sensing with at least one electrode disposed in the ITV.

A fourth non-limiting example takes the form of a pacemaker system comprising: a lead with a proximal end and a distal end and having at least one electrode thereon with a conductor electrically coupling the electrode to the proximal end, the lead adapted for implantation in the internal thoracic vein (ITV) of a patient; and an implantable housing containing operational circuitry including: pacing means for generating therapy output in the form of a pacing output; interface means to couple to the conductor of the lead; and communication means for exchanging data with an external device or a second implantable medical device. The pacing means may be as shown and described above relative to block 1860; the interface means may comprise a header or port as described above relative to 1868; and the communication means may take a form as described above relative to 1862.

Additionally or alternatively to the fourth non-limiting example, the pacing means may be configured to deliver a pacing output effective to pace the heart using at least one electrode on the lead when the lead disposed in an internal thoracic vein (ITV) of a patient. In a sub-example, the pacing means may be configured to deliver pacing therapy as a current controlled output with a current in the range of about 10 mA to about 50 mA. In a sub-example, the pacing means may be configured to deliver pacing therapy as a current controlled output with a current in the range of about 15 mA to about 40 mA. In a sub-example, the pacing means may be configured to deliver pacing therapy as a voltage controlled output with a peak voltage in the range of about 5 Volts to about 40 Volts. In a sub-example, the pacing means may be configured to deliver pacing therapy as a voltage controlled output with a peak voltage in the range of about 10 volts to about 30 volts.

Additionally or alternatively to the fourth non-limiting example, the at least one electrode on the lead may have a surface area in the range of about 15 $mm^2$ to about 30 $mm^2$.

Additionally or alternatively to the fourth non-limiting example, the housing may have a volume in the range of about 2 to about 20 cc.

Additionally or alternatively to the fourth non-limiting example, the housing may have a volume in the range of about 3 to about 12 cc.

Additionally or alternatively to the fourth non-limiting example, the housing may have a length in the range of about 40 to about 80 mm, a width in the range of about 10 to about 30 mm, and a thickness in the range of about 5 to about 10 mm.

Additionally or alternatively to the fourth non-limiting example, the housing may be shaped and sized for implantation beneath the skin and over the sternum of a patient.

Additionally or alternatively to the fourth non-limiting example, the housing may be shaped and sized for implantation beneath the skin and in an intercostal position of a patient.

Additionally or alternatively to the fourth non-limiting example, the pacing means may be configured to deliver anti-tachycardia pacing therapy when the lead is disposed in an ITV of a patient.

Additionally or alternatively to the fourth non-limiting example, the pacing means may be configured to deliver bradycardia pacing therapy when the lead is disposed in an ITV of a patient.

Additionally or alternatively to the fourth non-limiting example, the communication means may be configured to communicate with a leadless cardiac pacemaker (LCP) adapted for positioning in the heart of a patient.

Additionally or alternatively to the fourth non-limiting example, the operational circuitry may comprise sensing means to sense conditions in a patient and the communications circuitry may be configured to cooperate with the LCP to provide to cardiac therapy using information from the sensing circuitry.

Additionally or alternatively to the fourth non-limiting example, the sensing means may be configured to determine whether an output of the LCP produces a desired result by analysis of cardiac electrical signals.

Additionally or alternatively to the fourth non-limiting example, the sensing means may be configured to determine whether an output of the LCP produces a desired result by analysis of sensed non-electrical signals.

Additionally or alternatively to the fourth non-limiting example, the sensing means may be configured to determine whether the patient needs therapy from the LCP.

Additionally or alternatively to the fourth non-limiting example, the communication means may be configured to communicate with a subcutaneously implantable defibrillator, and the operational circuitry may comprise sensing means for sensing cardiac activity using a lead in a patient's ITV to provide data for use by the subcutaneous implantable defibrillator.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various to combinations or permutations. The scope of the invention should be determined with reference to the appended claims, along with the full scope of equivalents to which such claims are entitled.

The claimed invention is:

1. A method of treating a patient using an implantable medical device system including an implantable pulse generator having a conductive housing and a lead having at least one electrode thereon, comprising:
    sensing a condition of the patient's heart necessitating electrical therapy; and
    delivering an electrical therapy between the at least one electrode, while the at least one electrode is disposed in an internal thoracic vein (ITV) of the patient, and the conductive housing of the implantable pulse generator, while the implantable pulse generator is disposed subcutaneously in the patient;
    wherein the lead is positioned along a path from the implantable pulse generator to an intercostal space over the ITV, then through the intercostal space and into the ITV.

2. The method of claim 1 wherein the implantable pulse generator is disposed in the left axilla of the patient.

3. The method of claim 1 wherein the implantable pulse generator is disposed in a subclavicular location.

4. The method of claim 1 wherein the at least one electrode comprises first and second electrodes, the step of delivering an electrical therapy is performed using the first electrode, and the step of sensing a condition necessitating electrical therapy is performed using the second electrode in combination with the conducive housing.

5. The method of claim 1 wherein the at least one electrode comprises first, second and third electrodes, the step of delivering an electrical therapy is performed using the first electrode, and the step of sensing a condition necessitating electrical therapy is performed using the second and third electrodes in combination with one another to sense cardiac electrical activity.

6. The method of claim 1 wherein the electrical therapy is a pacing therapy.

7. The method of claim 6 wherein the step of sensing a condition necessitating electrical therapy comprises sensing an atrial event using an electrode disposed in the ITV, and the step of delivering an electrical therapy is performed by using the sensed atrial event to time delivery of the pacing therapy.

8. The method of claim 7 wherein the pacing therapy is a bradycardia therapy.

9. The method of claim 7 wherein the pacing therapy is a resynchronization therapy.

10. The method of claim 6 wherein the pacing therapy is an anti-tachycardia pacing therapy.

11. The method of claim 1 wherein the electrical therapy is an anti-tachyarrhythmia therapy.

12. The method of claim 1 wherein the electrical therapy is a defibrillation therapy.

* * * * *